US008877706B2

(12) United States Patent
Li et al.

(10) Patent No.: US 8,877,706 B2
(45) Date of Patent: *Nov. 4, 2014

(54) MAYTANSINOID DERIVATIVES

(71) Applicant: Bio-Thera Solutions, Ltd., Co., Guangzhou (CN)

(72) Inventors: Shenfeng Li, Belmont, CA (US); Xiaobin Deng, Guangzhou (CN); Songnuan Tan, Guangzhou (CN); Weijia Tang, Guangzhou (CN); Chao Qin, Guangzhou (CN)

(73) Assignee: Bio-Thera Solutions Ltd., Co., Guangzhou Science (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/838,868

(22) Filed: Mar. 15, 2013

(65) Prior Publication Data
US 2014/0178415 A1 Jun. 26, 2014

(30) Foreign Application Priority Data

Dec. 21, 2012 (CN) .......................... 2012 1 0564166
Mar. 14, 2013 (CN) .......................... 2013 1 0081710

(51) Int. Cl.
A61K 38/00 (2006.01)
A61P 29/00 (2006.01)
A61P 35/00 (2006.01)
C07D 498/08 (2006.01)
C07K 16/30 (2006.01)
A61K 47/48 (2006.01)

(52) U.S. Cl.
CPC .............. C07D 498/08 (2013.01); C07K 16/30 (2013.01); A61K 47/48569 (2013.01)
USPC ........................... 514/1.1; 514/12.2; 514/19.3

(58) Field of Classification Search
CPC ........................ A61K 47/48569; C07K 16/30
See application file for complete search history.

(56) References Cited

U.S. PATENT DOCUMENTS

| 3,896,111 | A | 7/1975 | Kupchan et al. |
| 4,137,230 | A | 1/1979 | Hashimoto et al. |
| 4,256,746 | A | 3/1981 | Miyashita et al. |
| 4,260,608 | A | 4/1981 | Miyashita et al. |
| 5,208,020 | A | 5/1993 | Chari et al. |
| 5,416,064 | A | 5/1995 | Chari et al. |
| 6,333,410 | B1 | 12/2001 | Chari et al. |
| 2006/0167245 | A1 | 7/2006 | Widdison et al. |
| 2007/0116774 | A1* | 5/2007 | Desai et al. ................. 424/489 |
| 2012/0121615 | A1 | 5/2012 | Flygare et al. |

FOREIGN PATENT DOCUMENTS

EP 0021173 A1 1/1981
WO WO 2005/037992 * 4/2005

OTHER PUBLICATIONS

Cassady, John M., et al., Recent Developments in the Maytansinoid Antitumor Agents, Chem. Pharm. Bull., Jan. 2004, pp. 1-26, vol. 52, No. 1, Pharmaceutical Society of Japan.
Desmyter, Aline, et al., Crystal structure of a camel single-domain VH antibody fragment in complex with lysozyme, Nature Structural Biology, Sep. 1996, pp. 803-811, vol. 3, No. 9, Nature Publishing Group, http://www.nature.com/nsmb.
Greenberg, A.S., et al., A new antigen receptor gene family that undergoes rearrangement and extensive somatic diversification in sharks, Nature, Mar. 9, 1995, pp. 168-173, vol. 374.
Greene, T.W., et al., Protecting Groups in Organic Synthesis, 1999, Third Edition, Wiley, New York.
Hudziak, R.M., et al.,p185HER2 Monoclonal Antibody Has Antiproliferative Effects In Vitro and Sensitizes Human Breast Tumor Cells to Tumor Necrosis Factor, Molecular and Cellular Biology, Mar. 1989, pp. 1165-1172, vol. 9, No. 3, American Society for Microbiology.
Ishiyama, Munetaka, et al., A Combined Assay of Cell Viability and in Vitro Cytotoxicity with a Highly Water-Soluble Tetrazolium Salt, Neutral Red and Crystal Violet, Biol. Pharm. Bull. 1996, vol. 19, No. 11, Pharmaceutical Society of Japan.
Issel, B., et al., Maytansine, 5 Cancer Treatment Reviews, 1978, pp. 199-207.
Kawai, Akiyoshi, et al., Chemical Modification of Ansamitocins. III. Synthesis and Biological Effects of 3-Acyl Esters of Maytansinol, Chem. Pharm., Bull., 1984, Chem. Pharm. Bull., pp. 3441-3451, vol. 32, No. 9.
Kupchan, S.M., et al., Maytansine, a novel antileukemic ansa macrolide from *Maytenus ovatus*, J. Am. Chem. Soc., 1972, pp. 1354-1356, vol. 94, No. 4.
Mossner, Ekkehard, et al., Increasing the efficacy of CD290 antibody therapy through the engineering of a new type II anti-CD20 antibody with enhanced direct and immune effector cell-mediated B-cell cytotoxicity, Blood, Jun. 3, 2010, pp. 4393-4402, vol. 115, No. 22.
Nisonoff, A., et al., Separation of Univalent Fragments from the Bivalent Rabbit Antibody Molecule by Reduction of Disulfide Bonds, 1960, pp. 230-244, Archives of Biochemistry and Biophysics 89.
O'Keefe, Donald O., et al., Characterization of a Transferrin-Diphtheria Toxin Conjugate, The Journal of Biological Chemistry, 1985, pp. 932-937, vol. 260, No. 2, American Society of Biological Chemists, Inc.
Parham, Peter, On the Fragmentation of Monoclonal IgG1, IgG2a, and IgG2b from BALB/c Mice, The Journal of Immunology, Dec. 1983, pp. 2895-2902, vol. 131, No. 6, American Association of Immunologists.

(Continued)

Primary Examiner — Marcela M Cordero Garcia
Assistant Examiner — Sergio Coffa
(74) Attorney, Agent, or Firm — Buchanan Ingersoll & Rooney PC

(57) ABSTRACT

Disclosed herein are maytansinoid drug linker derivatives which can be linked to a antigen binding unit (Abu), and maytansinoid drugs linked with an antigen binding unit (Drug-Linker-Antigen binding Unit: D-L-Abu), for targeted delivery to disease tissues. D-L-Abu, D-L-Abu derivatives, and methods relating to the use of such drug conjugates to treat antigen positive cells in cancers and immunological disorders are provided.

46 Claims, 18 Drawing Sheets

(56) References Cited

OTHER PUBLICATIONS

Smith, C.R. Jr., et al., Alkaloids, 1984, ed. Pelletier, S.W., 2, pp. 149-204, Wiley, NY.

Remillard, Stephen et al., Antimitotic Activity of the Potent Tumor Inhibitor Maytansine, Science, Sep. 1975, pp. 1002-1005, vol. 189, Dept. of Biology, University of Virginia.

Spring, Susan B., et al., The Journal of Immunology, Aug. 1974, pp. 470-478, vol. 113, No. 2, The Williams & Wilkins Co.

Stanfield, Robyn L., et al., Crystal Structure of a Shark Single-Domain Antibody V Region in Complex with Lysozyme, *Science*, Sep. 17, 2004, pp. 1770-1773, vol. 305, www.sciencemag.org.

Stewart, Ross, et al., A variant human IgGI-Fc mediates improved ADCC, Protein Engineering, Design & Selection, May 18, 2011, pp. 671-678, vol. 24, No. 9, Oxford University Press, doi:10.1093/protein/gzr015.

Widdison, Wayne C., et al., Semisynthetic Maytansine Analogues for the Targeted Treatment of Cancer, J. Med. Chem., J. Med. Chem., 2006, pp. 4392-4408, vol. 49, American Chemical Society.

Wolpert-Defilippes, Mary K., et al., Initial Studies on Maytansine-Induced Metaphase Arrest in L1210 Murine Leukemia Cells, Biochemical Pharmacology, 1975, pp. 1735-1738, vol. 24, Pergamon Press, Great Britain.

Wood, Clive R., et al., High Level Synthesis of Immunoglobulins in Chinese Hamster Ovary Cells, Journal of Immunology, Nov. 1, 1990, pp. 3011-3016, vol. 145, No. 9, American Assn. of Immunologists.

Yu, Tin-Wein, et al., The biosynthetic gene cluster of the maytansinoid antitumor agent ansamitocin from *Actinosynnema pretiosum*, PNAS, Jun. 11, 2002, pp. 7968-7973, vol. 99, No. 12, www.pnas.org/cgi/doi/10.1073/pnas.092697199.

* cited by examiner

```
  1 GACATCCAGA TGACCCAGTC TCCATCCTCC CTGTCTGCAT CTGTAGGAGA
    D  I  Q  M  T  Q  S  P  S  S  L  S  A  S  V  G  D

51 CAGAGTCACC ATCACTTGCC AGGCGAGTCA GGACATTAGC AACTATTTAA
    R  V  T  I  T  C  Q  A  S  Q  D  I  S  N  Y  L  N

101 ATTGGTATCA ACAGAAACCA GGGAAAGCCC CTAAGCTCCT GATCTACGAT
    W  Y  Q  Q  K  P  G  K  A  P  K  L  L  I  Y  D

151 GCATCCAATT TGGAGACAGG GGTCCCATCC AGGTTCAGTG GAAGTGGATC
    A  S  N  L  E  T  G  V  P  S  R  F  S  G  S  G  S

201 TGGGACAGAT TTTACCTTCA CCATTAGCAG CCTGCAGCCT GAAGATATTG
    G  T  D  F  T  F  T  I  S  S  L  Q  P  E  D  I  A

251 CAACATATTT CTGTCAACAT TTTGATCATC TCCCGCTCGC TTTCGGCGGA
    T  Y  F  C  Q  H  F  D  H  L  P  L  A  F  G  G

301 GGGACCAAGG TGGAGATCAA ACGTACGGTG GCTGCACCAT CTGTCTTCAT
    G  T  K  V  E  I  K  R  T  V  A  A  P  S  V  F  I

351 CTTCCCGCCA TCTGATGAGC AGTTGAAATC TGGAACTGCC TCTGTTGTGT
    F  P  P  S  D  E  Q  L  K  S  G  T  A  S  V  V  C

401 GCCTGCTGAA TAACTTCTAT CCCAGAGAGG CCAAAGTACA GTGGAAGGTG
    L  L  N  N  F  Y  P  R  E  A  K  V  Q  W  K  V

451 GATAACGCCC TCCAATCGGG TAACTCCCAG GAGAGTGTCA CAGAGCAGGA
    D  N  A  L  Q  S  G  N  S  Q  E  S  V  T  E  Q  D

501 CAGCAAGGAC AGCACCTACA GCCTCAGCAG CACCCTGACG CTGAGCAAAG
    S  K  D  S  T  Y  S  L  S  S  T  L  T  L  S  K  A

551 CAGACTACGA GAAACACAAA GTCTACGCCT GCGAAGTCAC CCATCAGGGC
    D  Y  E  K  H  K  V  Y  A  C  E  V  T  H  Q  G

601 CTGAGCTCGC CCGTCACAAA GAGCTTCAAC AGGGGAGAGT GTTGA
    L  S  S  P  V  T  K  S  F  N  R  G  E  C  *
```

Fig. 15A

```
  1 CAGGTGCAGG AGTCGGGCCC AGGACTGGTG AAGCCTTCGG AGACCCTGTC
    Q  V  Q  E  S  G  P  G  L  V  K  P  S  E  T  L  S

51 CCTCACCTGC ACTGTCTCTG GTGGCTCCGT GAGTAGTGGG GACTATTACT
    L  T  C  T  V  S  G  G  S  V  S  S  G  D  Y  Y  W

101 GGACCTGGAT CCGGCAGAGC CCAGGGAAGG GACTGGAGTG GATTGGGCAC
    T  W  I  R  Q  S  P  G  K  G  L  E  W  I  G  H

151 ATCTATTACA GTGGGAACAC CAACTACAAC CCCTCCCTTA AGAGTCGACT
    I  Y  Y  S  G  N  T  N  Y  N  P  S  L  K  S  R  L

201 CACCATATCA ATCGACACGT CCAAGACCCA GTTCTCCCTG AAGCTGAGCT
    T  I  S  I  D  T  S  K  T  Q  F  S  L  K  L  S

251 CTGTGACCGC TGCGGACACG GCCATCTATT ATTGTGTGAG AGATCGAGTG
    V  T  A  A  D  T  A  I  Y  Y  C  V  R  D  R  V

301 ACAGGTGCTT TTGATATCTG GGGCCAAGGT ACCCTGGTTA CCGTTAGCAG
    T  G  A  F  D  I  W  G  Q  G  T  L  V  T  V  S  S
```

```
351 CGCGAGCACC AAAGGCCCGA GCGTGTTTCC GCTGGCCCCG AGCAGCAAAA
     A  S  T   K  G  P  S   V  F  P   L  A  P   S  S  K  S

401 GCACCAGCGG TGGCACCGCA GCGCTGGGTT GCCTGGTGAA AGATTATTTC
     T  S  G   G  T  A   A  L  G  C   L  V  K   D  Y  F

451 CCGGAACCGG TGACGGTGTC GTGGAACTCA GGCGCCCTGA CCAGCGGCGT
     P  E  P   V  T  V  S   W  N  S   G  A  L  T   S  G  V

501 GCACACCTTC CCGGCTGTCC TACAGTCCTC AGGACTCTAC TCCCTCAGCA
     H  T  F   P  A  V  L   Q  S  S   G  L  Y   S  L  S  S

551 GCGTGGTGAC CGTGCCCTCC AGCAGCTTGG GCACCCAGAC CTACATCTGC
     V  V  T   V  P  S   S  S  L  G   T  Q  T   Y  I  C

601 AACGTGAATC ACAAGCCCAG CAACACCAAG GTGGACAAGA AAGTTGAGCC
     N  V  N  H   K  P  S   N  T  K   V  D  K   K  V  E  P

651 CAAATCTTGT GACAAAACTC ACACATGCCC ACCGTGCCCA GCACCTGAAC
     K  S  C   D  K  T  H   T  C  P   P  C  P   A  P  E  L

701 TCCTGGGGGG ACCGTCAGTC TTCCTCTTCC CCCCAAAACC CAAGGACACC
     L  G  G   P  S  V   F  L  F  P   P  K  P   K  D  T

751 CTCATGATCT CCCGGACCCC TGAGGTCACA TGCGTGGTGG TGGACGTGAG
     L  M  I  S   R  T  P   E  V  T   C  V  V  V   D  V  S

801 CCACGAAGAC CCTGAGGTCA AGTTCAACTG GTACGTGGAC GGCGTGGAGG
     H  E  D   P  E  V  K   F  N  W   Y  V  D   G  V  E  V

851 TGCATAATGC CAAGACAAAG CCGCGGGAGG AGCAGTACAA CAGCACGTAC
     H  N  A   K  T  K   P  R  E  E   Q  Y  N   S  T  Y

901 CGTGTGGTCA GCGTCCTCAC CGTCCTGCAC CAGGACTGGC TGAATGGCAA
     R  V  V  S   V  L  T   V  L  H   Q  D  W   L  N  G  K

951 GGAGTACAAG TGCAAGGTCT CCAACAAAGC CCTCCCAGCC CCCATCGAGA
     E  Y  K   C  K  V  S   N  K  A   L  P  A   P  I  E  K

1001 AAACCATCTC CAAAGCCAAA GGGCAGCCCC GAGAGCCACA GGTGTACACC
     T  I  S   K  A  K   G  Q  P  R   E  P  Q   V  Y  T

1051 CTGCCCCCAT CCCGGGATGA GCTGACCAAG AACCAGGTCA GCCTGACCTG
     L  P  P  S   R  D  E   L  T  K   N  Q  V   S  L  T  C

1101 CCTGGTCAAA GGCTTCTATC CCAGCGACAT CGCCGTGGAG TGGGAGAGCA
     L  V  K   G  F  Y  P   S  D  I   A  V  E   W  E  S  N

1151 ATGGGCAGCC GGAGAACAAC TACAAGACCA CGCCTCCCGT GCTGGACTCC
     G  Q  P   E  N  N   Y  K  T  T   P  P  V   L  D  S

1201 GACGGCTCCT TCTTCCTCTA CAGCAAGCTC ACCGTGGACA AGAGCAGGTG
     D  G  S  F   F  L  Y   S  K  L   T  V  D   K  S  R  W

1251 GCAGCAGGGG AACGTCTTCT CATGCTCCGT GATGCATGAG GCTCTGCACA
     Q  Q  G   N  V  F  S   C  S  V   M  H  E   A  L  H  N

1301 ACCACTACAC GCAGAAGAGC CTCTCCCTGT CTCCGGGTAA ATGA
     H  Y  T   Q  K  S   L  S  L  S   P  G  K   *
```

Fig. 15B

```
                        SEQUENCE LISTING

<160> NUMBER OF SEQ ID NOS: 14

<210> SEQ ID NO 1
<211> LENGTH: 214
<212> TYPE: PRT
<213> ORGANISM: Artificial Sequence
<220> FEATURE:
<223> OTHER INFORMATION: Chimeric

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 447
<212> TYPE: PRT
<213> ORGANISM: Artificial Sequence
<220> FEATURE:
<223> OTHER INFORMATION: Mouse human chimera.
```

```
<400> SEQUENCE: 2

Gln Val Gln Glu Ser Gly Pro Gly Leu Val Lys Pro Ser Glu Thr Leu
1               5                   10                  15

Ser Leu Thr Cys Thr Val Ser Gly Gly Ser Val Ser Ser Gly Asp Tyr
            20                  25                  30

Tyr Trp Thr Trp Ile Arg Gln Ser Pro Gly Lys Gly Leu Glu Trp Ile
        35                  40                  45

Gly His Ile Tyr Tyr Ser Gly Asn Thr Asn Tyr Asn Pro Ser Leu Lys
    50                  55                  60

Ser Arg Leu Thr Ile Ser Ile Asp Thr Ser Lys Thr Gln Phe Ser Leu
65                  70                  75                  80

Lys Leu Ser Ser Val Thr Ala Ala Asp Thr Ala Ile Tyr Tyr Cys Val
                85                  90                  95

Arg Asp Arg Val Thr Gly Ala Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

```
                        405                 410                 415
Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 3
<211> LENGTH: 213
<212> TYPE: PRT
<213> ORGANISM: Artificial Sequence
<220> FEATURE:
<223> OTHER INFORMATION: Mouse human chimera.

<400> SEQUENCE: 3

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 4
<211> LENGTH: 452
<212> TYPE: PRT
<213> ORGANISM: Artificial Sequence
<220> FEATURE:
<223> OTHER INFORMATION: Mouse human chimera.

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45
```

-continued

```
Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
450
```

-continued

```
<210> SEQ ID NO 5
<211> LENGTH: 214
<212> TYPE: PRT
<213> ORGANISM: Artificial Sequence
<220> FEATURE:
<223> OTHER INFORMATION: Mouse human chimera.

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 433
<212> TYPE: PRT
<213> ORGANISM: Artificial Sequence
<220> FEATURE:
<223> OTHER INFORMATION: Mouse human chimera.

<400> SEQUENCE: 6

Gln Leu Gln Glu Ser Gly Pro Gly Leu Val Lys Pro Ser Glu Thr Leu
1               5                   10                  15

Ser Leu Thr Cys Thr Val Ser Gly Gly Ser Val Ser Ser Gly Asp Tyr
            20                  25                  30

Tyr Trp Thr Trp Ile Arg Gln Ser Pro Gly Lys Gly Leu Glu Trp Ile
        35                  40                  45

Gly His Ile Tyr Tyr Ser Gly Asn Thr Asn Tyr Asn Pro Ser Leu Lys
50                  55                  60

Ser Arg Leu Thr Ile Ser Ile Asp Thr Ser Lys Thr Gln Phe Ser Leu
65                  70                  75                  80

Lys Leu Ser Ser Val Thr Ala Ala Asp Thr Ala Ile Tyr Tyr Cys Val
                85                  90                  95
```

```
Arg Asp Arg Val Thr Gly Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Glu Arg Lys Cys Cys Val Glu Cys Pro Ala Gly Pro
210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Gln Phe Asn Trp Tyr Val Asp Gly Val Glu Val His Asn
            260                 265                 270

Ala Lys Thr Lys Pro Arg Glu Glu Gln Phe Asn Ser Thr Phe Arg Val
        275                 280                 285

Val Ser Val Leu Thr Val Val His Gln Asp Trp Leu Asn Gly Lys Glu
290                 295                 300

Tyr Lys Cys Lys Val Ser Asn Lys Gly Leu Pro Ala Pro Ile Glu Lys
305                 310                 315                 320

Thr Ile Ser Lys Thr Lys Gly Gln Pro Arg Glu Pro Gln Val Tyr Thr
                325                 330                 335

Leu Pro Pro Ser Arg Glu Glu Met Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Met Leu
370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys

<210> SEQ ID NO 7
<211> LENGTH: 219
<212> TYPE: PRT
<213> ORGANISM: Artificial Sequence
<220> FEATURE:
<223> OTHER INFORMATION: Mouse human chimera.

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
```

```
                    20                  25                  30
Asn Gly Asn Thr Tyr Leu Asp Trp Tyr Gln Gln Thr Pro Gly Lys Ala
                35                  40                  45
Pro Lys Leu Leu Ile Tyr Lys Val Ser Asn Arg Phe Ser Gly Val Pro
 50                  55                  60
Ser Arg Phe Ser Gly Ser Gly Ser Gly Thr Asp Phe Thr Phe Thr Ile
 65                  70                  75                  80
Ser Ser Leu Gln Pro Glu Asp Ile Ala Thr Tyr Tyr Cys Phe Gln Tyr
                85                  90                  95
Ser His Val Pro Trp Thr Phe Gly Gln Gly Thr Lys Leu Gln Ile Thr
                100                 105                 110
Arg Glu Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
                130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Cys
                210                 215

<210> SEQ ID NO 8
<211> LENGTH: 222
<212> TYPE: PRT
<213> ORGANISM: Artificial Sequence
<220> FEATURE:
<223> OTHER INFORMATION: Mouse human chimera.

<400> SEQUENCE: 8

Gln Val Gln Leu Gln Gln Ser Gly Ala Glu Val Lys Lys Pro Gly Ser
 1                   5                  10                  15
Ser Val Lys Val Ser Cys Lys Ala Ser Gly Tyr Thr Phe Thr Asn Tyr
                20                  25                  30
Tyr Ile Tyr Trp Val Arg Gln Ala Pro Gly Gln Gly Leu Glu Trp Ile
                35                  40                  45
Gly Gly Ile Asn Pro Thr Ser Gly Gly Ser Asn Phe Asn Glu Lys Phe
 50                  55                  60
Lys Thr Arg Val Thr Ile Thr Ala Asp Glu Ser Ser Thr Thr Ala Tyr
 65                  70                  75                  80
Met Glu Leu Ser Ser Leu Arg Ser Glu Asp Thr Ala Phe Tyr Phe Cys
                85                  90                  95
Thr Arg Gln Gly Leu Trp Phe Asp Ser Asp Gly Arg Gly Phe Asp Phe
                100                 105                 110
Trp Gly Gln Gly Thr Thr Val Thr Val Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
```

```
                    165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Pro
    210                 215                 220

<210> SEQ ID NO 9
<211> LENGTH: 214
<212> TYPE: PRT
<213> ORGANISM: Artificial Sequence
<220> FEATURE:
<223> OTHER INFORMATION: Mouse human chimera.

<400> SEQUENCE: 9

Gln Val Asp Ile Gln Met Thr Gln Ser Pro Ser Ser Leu Ser Ala Ser
1               5                   10                  15

Val Gly Asp Arg Val Thr Ile Thr Cys Ser Ala Ser Ser Ser Val Thr
            20                  25                  30

Tyr Met Tyr Trp Tyr Gln Gln Lys Pro Gly Lys Ala Pro Lys Leu Leu
        35                  40                  45

Ile Tyr Asp Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser His Ile
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu
    210

<210> SEQ ID NO 10
<211> LENGTH: 223
<212> TYPE: PRT
<213> ORGANISM: Artificial Sequence
<220> FEATURE:
<223> OTHER INFORMATION: Mouse human chimera.

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30
```

Trp Met His Trp Val Arg Gln Ala Pro Gly Gln Gly Leu Glu Trp Ile
            35                  40                  45

Gly Glu Phe Asn Pro Ser Asn Gly Arg Thr Asn Tyr Asn Glu Lys Phe
 50                  55                  60

Lys Ser Lys Ala Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser
            210                 215                 220

<210> SEQ ID NO 11
<211> LENGTH: 214
<212> TYPE: PRT
<213> ORGANISM: Artificial Sequence
<220> FEATURE:
<223> OTHER INFORMATION: Mouse human chimera.

<400> SEQUENCE: 11

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 451
<212> TYPE: PRT
<213> ORGANISM: Artificial Sequence
<220> FEATURE:
<223> OTHER INFORMATION: Mouse human chimera.

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 13
<211> LENGTH: 213
<212> TYPE: PRT
<213> ORGANISM: Artificial Sequence
<220> FEATURE:
<223> OTHER INFORMATION: Mouse human chimera.

<400> SEQUENCE: 13

Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Ser Val Ser Tyr Ile
            20                  25                  30
His Trp Phe Gln Gln Lys Pro Gly Ser Ser Pro Lys Pro Trp Ile Tyr
        35                  40                  45
Ala Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Thr Ser Asn Pro Pro Thr
                85                  90                  95
Phe Gly Gly Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

```
<210> SEQ ID NO 14
<211> LENGTH: 224
<212> TYPE: PRT
<213> ORGANISM: Artificial Sequence
<220> FEATURE:
<223> OTHER INFORMATION: Mouse human chimera.

<400> SEQUENCE: 14

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

MAYTANSINOID DERIVATIVES

CROSS REFERENCE TO RELATED APPLICATIONS

This application claims priority under 35 U.S.C. §119 to CN 201210564166.7, filed on Dec. 21, 2012 and CN 201310081710.7, filed on Mar. 14, 2013, the contents of which is hereby expressly incorporated by reference in their entirety for all purposes and are assigned to the assignee hereof.

The present invention provides maytansinoid derivatives, including maytansinoid derivatives for linking to antigen binding unit and maytansinoid drug linked with antigen binding unit, for targeted delivery to disease cells. Also provided are related compositions and methods for treating diseases, such as cancers and immunological disorders.

BACKGROUND

Maytansinoids are highly cytotoxic compounds which inhibit the formation of microtubule protein polymerization (Remillard, et al., Science 189, 1002-1005 (1975)). Maytansine was first isolated by Kupchan et al. (J. Am. Chem. Sci 94:1354-1356 (1972)) from the east African shrub *Maytenus serrata*. Maytansinoids including maytansinol and C-3 esters of maytansinol were also produced by certain microbes (U.S. Pat. No. 4,151,042). Various analogues of maytansinol with different cytotoxicity have also been prepared by synthetic chemistry (for review see *Chem. Pharm. Bull.* 52(1) 1-26 (2004)). Examples of mytansinoids include maytansine, mertansine (DM1), DM3 and DM4. Maytansine is a strong mitotic inhibitor and shows significant inhibitory activity against multiple tumors including Lewis lung carcinoma and B-16 melanocarcinoma solid murine tumor models. Maytansine was reported to inhibit the human acute lymphoblastic leukemia line C.E.M. at concentrations as low as $10^{-7}$ μg/mL (Wolpert-DeFillippes et al., Biochem. Pharmacol. 1735-1738 (1975)). It also showed to be 100- to 1000-fold more cytotoxic than conventional chemotherapeutic agents like methotrexate, daunorubicin, and vincristine (U.S. Pat. No. 3,896,111).

Ansamitocins, the bacterial maytansinoids, show an activity spectrum and effective dosage range similar to maytansine. They inhibit P388 leukemia at daily doses as low as 0.8 μg/kg. Ansamitocin P3 (AP3) was also shown to be effective against multiple cancer cell lines (for review see Alkaloids, vol. 2, 149-204 (1984); Chem. Pharm. Bull. 52(1) 1-26 (2004)). The maytansinol C-3 esters with N-methyl-L-alanine derivatives are found to be much more cytotoxic than the corresponding esters of simple carboxylic acid and to be 100 times more cytotoxic than their epimers corresponding to N-methyl-D-alanine (U.S. Pat. Nos. 4,137,230; 4,260,608; Kawai, et al., Chem. Pharm. Bull. 32: 3441-3451 (1984); Widdison, et al., J. Med. Chem. 49: 4392-4408 (2006)).

Maytansinoids were expected to have the capacity to treat many different cancers due to their highly toxic nature and the in vitro activities against multiple cancer cell lines. However, the toxicity also made this class of compounds not favorable in human clinical trials as the side effects were intolerable for many patients (Issel et al., Cancer Treat. Rev. 199-207 (1978)). Accordingly, targeted delivery of cytotoxic compounds to cancer cells by conjugating toxic drugs to monoclonal antibodies (ADC for antibody drug conjugate) is proposed in order to reduce the side effects. Certain conjugates of cytotoxic drugs such as maytansinoids, auristatins, anthracyclins, duocarmycins, etc. with antibodies are being evaluated in preclinical or clinical studies in the treatment of diseases.

Antibody drug conjugates (ADCs) are composed of three key elements: antibody, linker, and drug. The selection of a particular antibody and drug will have a great impact on the efficacy and safety depending on the particular disease. Linker stability and the method by which the drug is conjugated to the antibody plays a critical role in the success or failure of the ADC drug development.

The efficacy of an ADC depends in part on combination of a variety of parameters, involving not only the specificity of the antibody and the potency of drugs, but also the linker's stability or sensitivity to cleavage, the cell surface triggered the internalization, trafficking, and subsequent release of the active cytotoxic payload. Thus, ADC comprising different drug linkers or with different antibodies against the same target can vary significantly in their utility.

SUMMARY OF THE INVENTION

The present invention provides maytansinoid drug derivatives which can be linked to a antigen binding unit (Abu), and maytansinoid drug linked with antigen binding unit (Drug-Linker-Antigen binding Unit: D-L-Abu), for targeted delivery to disease cells or tissues. D-L-Abu, D-L-Abu derivatives, and methods relating to the use of such drug conjugates to treat antigen positive cells in cancers and immunological disorders are also provided. The antigen binding unit, Abu, such as an antibody, or other targeting moiety in the D-L-Abu, binds to an antigen in the disease cells or tissues. A drug conjugated to the Abu exerts a cytotoxic, cytostatic, or immunosuppressive effect on the antigen-expressing cells to treat or prevent recurrence of antigen-positive cancers or immunological disorders. The present technology provides drug-linker-antigen binding unit exerting cellular inhibitory or killing effect on the antigen positive cells, while minimizing the undesirable side effects, such as bystander killing effects on antigen negative cells.

In one aspect, provided are maytansinoid derivative compounds capable of conjugation to an antigen binding unit via a linker that is not acid labile, not peptidase cathepsin sensitive, and does not contain a disulfide bond. Such derivatives may also be referred to as "drug-linkers." In some embodiments, the linker modified maytansinoid compounds is a maytansinoid $N_2'$-deacetyl-$N_2'$-(6-maleimido-1-oxo-hexyl) maytansine, or its derivatives, wherein the linker is not acid labile, not peptidase cathepsin sensitive, and does not contain a disulfide bond. Such linkers are contemplated to provide stability to the D-L-Abu prior to endocytosis, such as during circulation, to prevent premature degradation of D-L-Abu and release of the toxic drug, thus minimizes the toxic effect of the drug.

In some embodiments, provided herein is a maytansinoid derivative of Formula I or I-1, formula II or II-1:

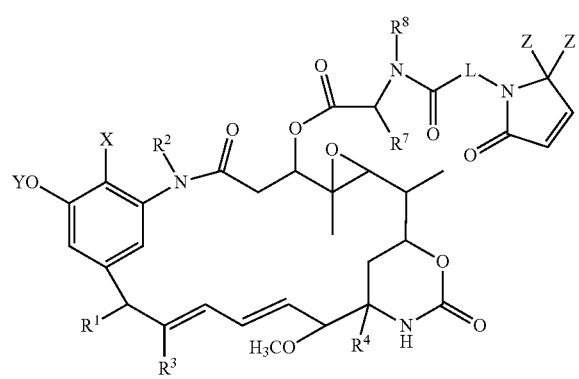

-continued

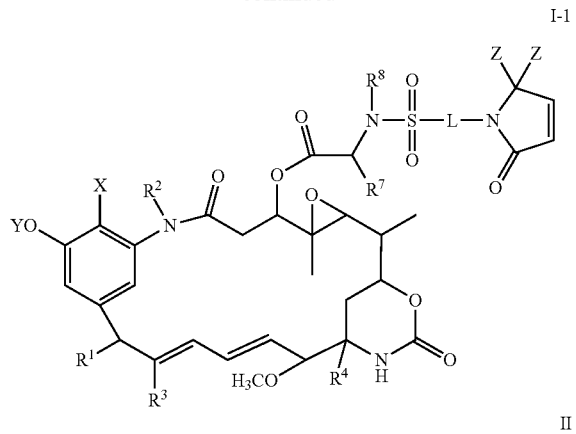
I-1

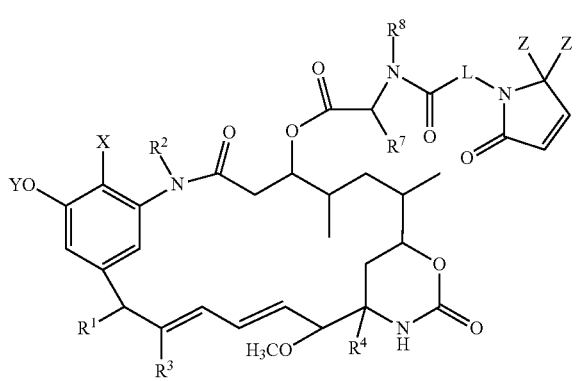
II

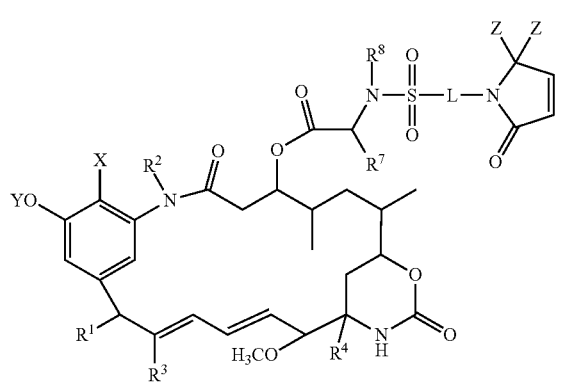
II-1 or a salt thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
each Z is independently hydrogen or $C_1$-$C_4$ alkyl, or the two Z with the carbon atom to which they are attached form a C=O; and
L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —NR$^8$—, —C(O)—, —C(=O)NR$^8$—, —NR$^8$C(=O)—, —SO$_2$NR$^8$—, or —NR$^8$SO$_2$—; preferably L is —(CH$_2$)$_m$—, wherein m is selected from an integer of 1 to 20, preferably 1 to 10, more preferably 5 to 10;

substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo.

In another aspect, provided is a composition comprising the above-described maytansinoid compound and an antigen binding unit capable of being conjugated with each other.

In another aspect, provided is an antigen binding unit conjugated with a maytansinoid compound, wherein the maytansinoid compound is modified, and linked to an antigen binding unit via a linker that is not acid labile, not peptidase cathepsin sensitive, and does not contain a disulfide bond.

In some embodiments, provided herein is a maytansinoid linker antigen binding unit conjugate of Formula Ia, Ia-1, IIa or IIa-1:

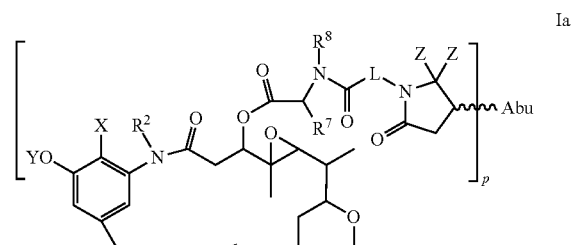
Ia

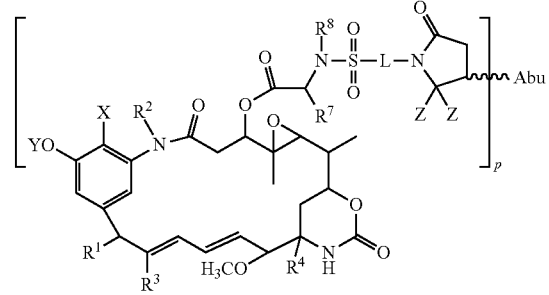
Ia-1

-continued

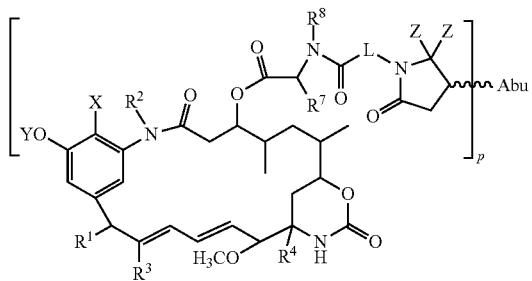

IIa

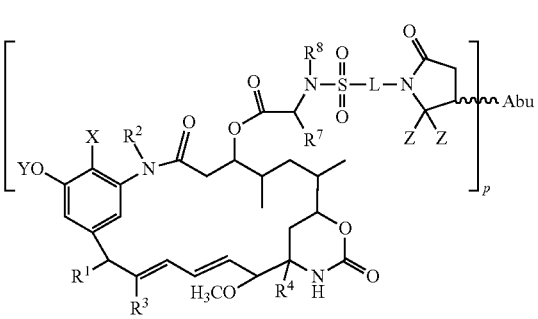

IIa-1 or a pharmaceutically acceptable salt or solvate thereof, wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
p is selected from 1, 2, 3, 4, 5, 6, 7, 8, 9, and 10;
each Z is independently hydrogen or $C_1$-$C_4$ alkyl, or the two Z with the carbon atom to which they are attached form a C=O;
L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —NR—, —C(O)—, —C(=O)NR$^8$—, —NR$^8$C(=O)—, —SO$_2$NR$^8$—, or —NR$^8$SO$_2$—; Preferably L is —(CH$_2$)$_m$—, wherein m is selected from an integer of 1 to 20, preferably 1 to 10, more preferably 5 to 10;
substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and
Abu is an antigen binding unit.

In

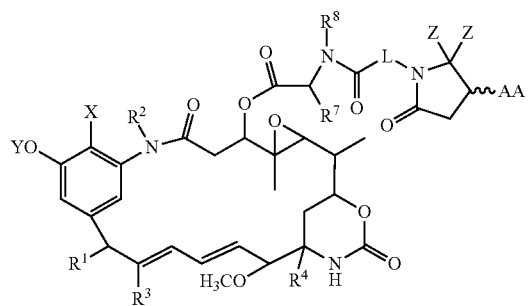

Ib

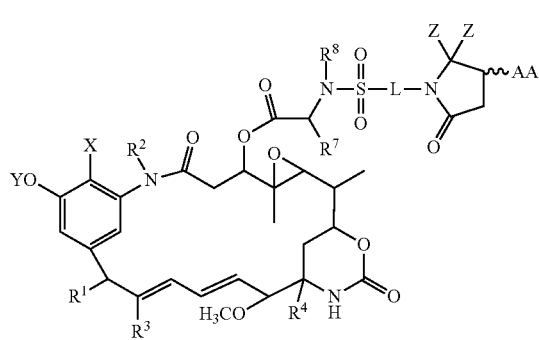

Ib-1

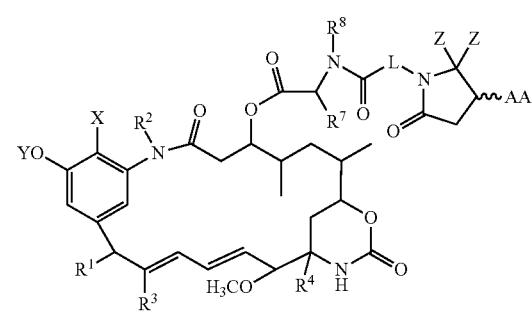

IIb

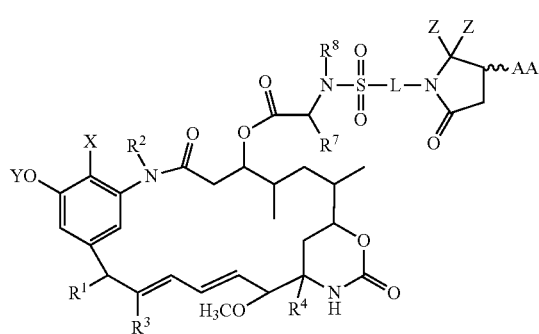

IIb-1 or a salt thereof,
wherein
- X is hydrogen or halo;
- Y is selected from the group consisting of hydrogen, $C_1$-$C_6$ alkyl, $C_3$-$C_6$ cycloalkyl, and —C(=O)$R^5$;
- $R^1$ is selected from the group consisting of hydrogen, —OH, —OC(=O)$R^5$ and —O$R^5$;
- $R^2$ is hydrogen or $C_1$-$C_6$ alkyl;
- $R^3$ is methyl, —$CH_2OH$, or —$CH_2C(=O)R^6$;
- $R^4$ is —OH or —SH;
- $R^5$ is $C_1$-$C_6$ alkyl or benzyl;
- $R^6$ is $C_1$-$C_6$ alkyl, phenyl or benzyl;
- $R^7$ is hydrogen, $C_1$-$C_6$ alkyl or an amino acid side chain;
- $R^8$ is hydrogen or $C_{1-6}$ alkyl;
- each Z is independently hydrogen or $C_1$-$C_4$ alkyl, or the two Z with the carbon atom to which they are attached form a C=O;
- L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8$C(=O)—, —$SO_2NR^8$—, or —$NR^8SO_2$—; preferably L is —$(CH_2)_m$—, wherein m is selected from an integer of 1 to 20, preferably 1 to 10, more preferably 5 to 10;
- substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and
- AA is an amino acid, such as a cysteine or a thiolated amino acid, such as a thiolated lysine.

In some embodiments, provided are compounds of the formula:

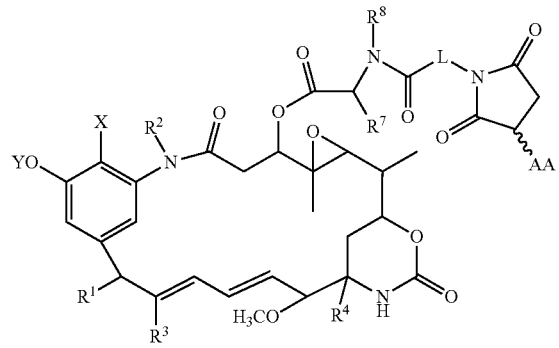

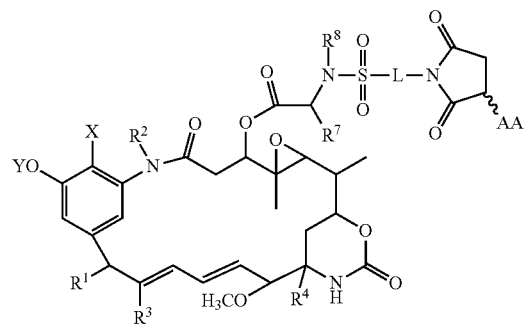

-continued

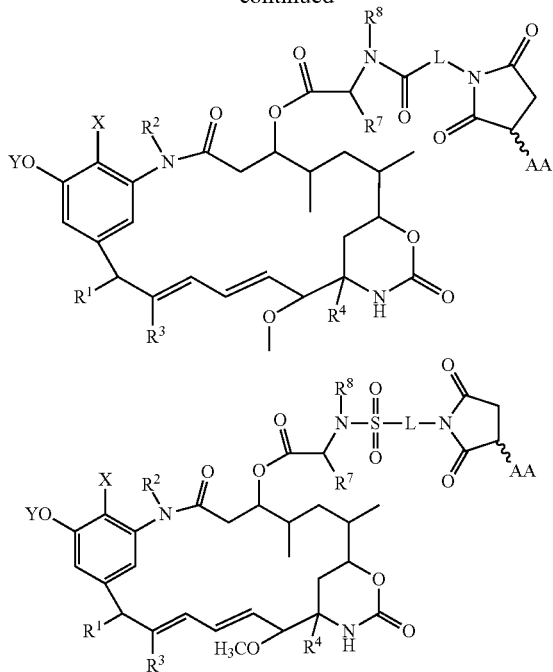

or a pharmaceutically acceptable salt or solvate thereof.

In another aspect, provided is a composition comprising the above-described maytansinoid compound of Formula Ib, Ib-1, IIb or IIb-1.

In another aspect, provided is a method for targeting a maytansinoid to antigen positive cells or tissues with an antigen binding unit conjugated with maytansinoid described herein.

In another aspect, provided is an antigen binding unit, Bat0206 comprising an anti-EGFR light chain having an amino acid sequence of SEQ ID NO: 1 and an anti-EGFR heavy chain having an amino acid sequence of SEQ ID NO: 2.

In another aspect, provided is a maytansinoid linker antigen binding unit conjugate wherein the antigen binding unit is Bat0206.

In another aspect, provided is a method for treatment of proliferative disorders such as tumors, inflammatory or immunologic diseases such as graft rejections, and other diseases that can be treated by targeted therapy in a subject in need of the treatment, wherein the disease is characterized by cells comprising an antigen that binds to an antigen binding unit, said method comprising administering to the subject an effective amount of the antigen binding unit conjugated with one or more maytansinoid compound described herein.

BRIEF DESCRIPTION OF THE DRAWINGS

FIGS. 15A and 15B show the amino acid sequences of anti-EGFR antibody.

DETAILED DESCRIPTION OF THE INVENTION

Definitions

Figure 1:
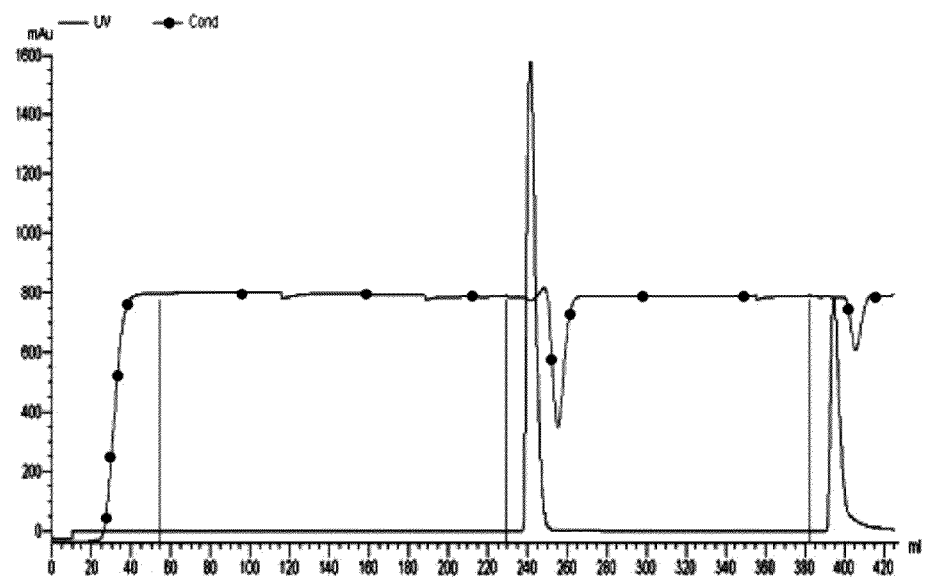
FIG. 1 shows Sephadex G25(M) chromatograph of purification of Batansine-0206.
Figure 2:
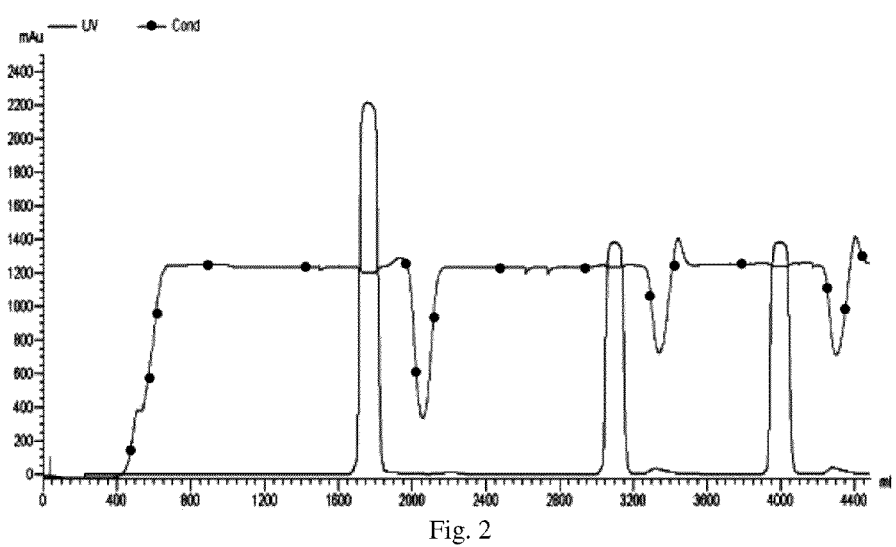
FIG. 2 shows Sephadex G25(M) chromatograph of purification of Batansine-1206.
Figure 3:
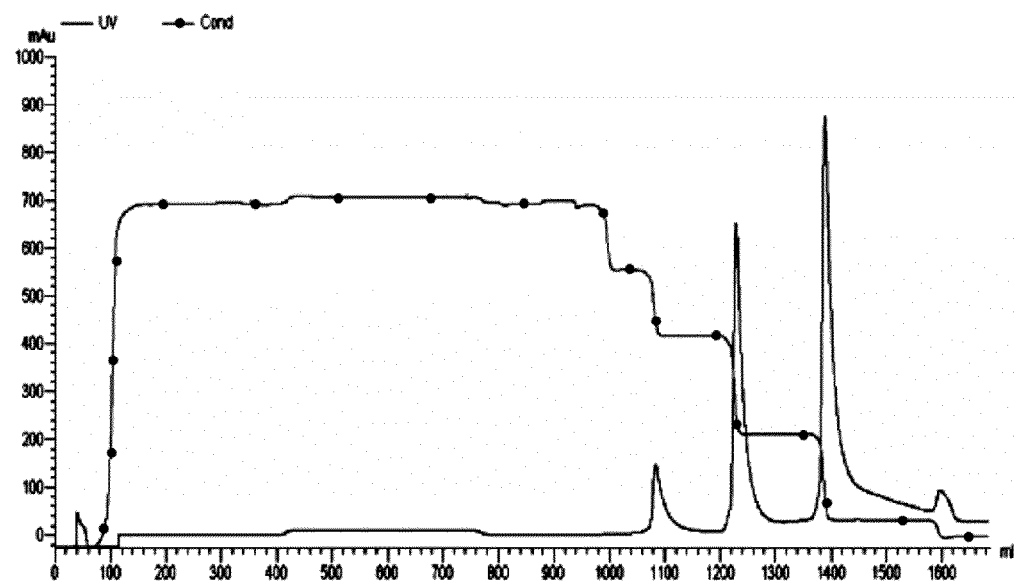
FIG. 3 shows Phenyl Sepharose FF column separation of Batansine-0206.
Figure 4:
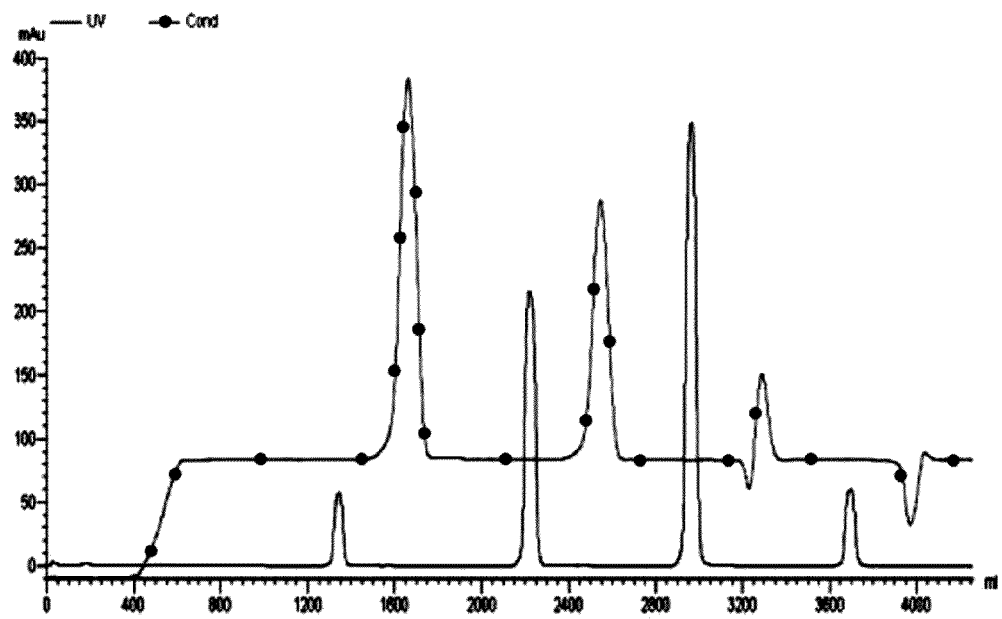
FIG. 4 shows Sephadex G25(M) column separation of Batansine-0606.
Figure 5:
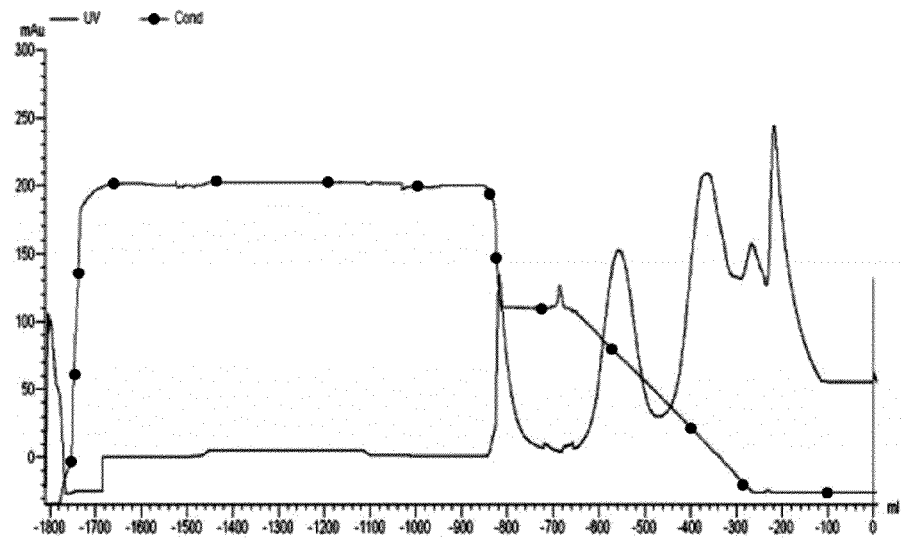
FIG. 5 shows Phenyl Sepharose FF column separation of Batansine-0606.

As used herein, the following definitions shall apply unless otherwise indicated.

As used herein, unless otherwise stated, the singular forms "a," "an," and "the" include plural reference. Thus, for example, a reference to "a compound" includes a plurality of compounds.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% or plus or minus 5%, or plus or minus 1% of the particular term.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, "maytansinoid" refers to a maytansine analogue, including stereoisomers thereof. Maytansine can be isolated from plants of the genus *Maytenus* U.S. Pat. No. 3,896,111). It is of the formula:

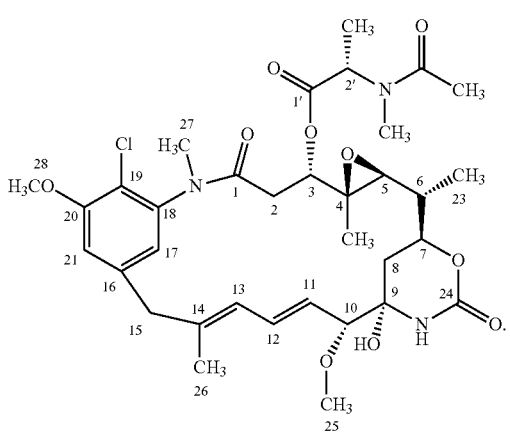 [SMILES: COc1cc2cc(c1Cl)N(C)C(=O)C[C@H](OC(=O)[C@H](C)N(C)C(C)=O)[C@]1(C)O[C@H]1[C@H](C)[C@@H]1C[C@@](O)(NC(=O)O1)[C@H](OC)/C=C/C=C(\C)C2]

Maytansinoids are compounds having the ring structure of maytansine with one or more modifications of the substituents on the ring.

"Alkyl" refers to monovalent saturated aliphatic hydrocarbyl groups having from 1 to 10 carbon atoms and preferably 1 to 6 carbon atoms. $C_v$ alkyl wherein v is an integer represents an alkyl having v carbons. This term includes, by way of example, linear and branched hydrocarbyl groups such as methyl($CH_3$—), ethyl($CH_3CH_2$—), n-propyl ($CH_3CH_2CH_2$—), isopropyl(($CH_3)_2CH$—), n-butyl ($CH_3CH_2CH_2CH_2$—), isobutyl(($CH_3)_2CHCH_2$—), sec-butyl(($CH_3)(CH_3CH_2)CH$—), t-butyl(($CH_3)_3C$—), n-pentyl ($CH_3CH_2CH_2CH_2CH_2$—), and neopentyl(($CH_3)_3CCH_2$—). "Alkylene" is a divalent saturated aliphatic hydrocarbyl groups having from 1 to 10 carbon atoms and preferably 1 to 6 carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl(>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably from 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' and R" is hydrogen but not both. When referring to a disubstituted amino, it is meant that neither R' and R" are hydrogen.

"Amino acid" refers any compound, whether natural, unnatural or synthetic, which comprises both an amino group and a carboxy group. Examples of amino acid include, but are not limited to glycine ($NH_2CH_2COOH$), cysteine, alanine, N-methyl-L-alanine, including both the D and L optical isomers. "Amino acid side chain" refers to the substituent that replaces a hydrogen of the methylene group of glycine or glycine derivatives, such as N-alkylglycine or glycine esters. Examples of an amino acid side chain include, but are not limited to the side chains of the natural amino acids, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Carbonyl" refers to the divalent group —C(O)— which is equivalent to —C(=O)—.

"Carboxy" or "carboxyl" refers to —COOH or $CO_2H$ or salts thereof.

"Carboxylic acid" refers to a compound having at least one carboxy.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl:

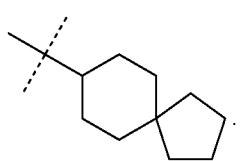

Cycloalkylene refers to a cyclic alkylene.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring.

Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Substituted alkyl," "substituted alkenyl," "substituted alkynyl," "substituted cycloalkyl," "substituted cycloalkenyl," "substituted aryl," "substituted heteroaryl" or "substituted heterocyclic" refers to alkyl, alkenyl, alkynyl, cycloalkyl, cycloalkenyl, aryl, heteroaryl or heterocyclic groups, respectively, which are substituted with 1 to 5, preferably 1 to 3, or more preferably 1 to 2 substituents selected from the group consisting of alkyl, halo alkyl, —O—R$^{20}$, —S—R$^{20}$, alkenyl, alkynyl, —C(=O)R$^{20}$, —C(=S)R$^{20}$, —C(=O)OR$^{20}$, —NR$^{20}$C(=O)R$^{21}$, —OC(=O)R$^{21}$, —NR$^{20}$R$^{20}$, —C(=O)NR$^{20}$R$^{20}$, —C(=S)NR$^{20}$R$^{20}$, —NR$^{20}$R$^{20}$C(=O)NR$^{20}$R$^{20}$, —NR$^{20}$C(=S)NR$^{20}$R$^{20}$, —OC(=O)NR$^{20}$R$^{20}$, —SO$_2$NR$^{20}$R$^{20}$, —OSO$_2$NR$^{20}$R$^{20}$, —NR$^{20}$SO$_2$NR$^{20}$R$^{20}$, —C(=N R$^{20}$)NR$^{20}$R$^{20}$, aryl, —NR$^{20}$C(=O)OR$^{21}$, —OC(=O)OR$^{21}$, cyano, cycloalkyl, cycloalkenyl, —NR$^{20}$C(=NR$^{20}$)NR$^{20}$R$^{20}$, halo, hydroxy, heteroaryl, heterocyclic, nitro, —SO$_3$H, —SO$_2$R$^{21}$, and —OSO$_2$R$^{21}$, wherein each R$^{20}$ is selected from the group consisting of hydrogen, alkyl, alkenyl, alkynyl, aryl, cycloalkyl, cycloalkenyl, heteroaryl, and heterocyclic or two R$^{20}$ with the atom(s) bound thereto form a heterocyclic ring, and R$^{21}$ is selected from the group consisting of alkyl, alkenyl, alkynyl, aryl, cycloalkyl, cycloalkenyl, heteroaryl, and heterocyclic.

"Nitro" refers to the group —NO$_2$.

"Oxo" refers to the atom (=O) or (—O$^-$).

"Spiro ring systems" refers to bicyclic ring systems that have a single ring carbon atom common to both rings.

"Thiol" refers to the group —SH.

"Thiocarbonyl" refers to the divalent group —C(S)— which is equivalent to —C(=S)—.

"Thione" refers to the atom (=S).

"Compound" or "compounds" as used herein is meant to include the stereoiosmers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Solvate" refer to an association of a solvent with a compound, in the crystalline form. The solvent association is typically due to use of the solvent in the synthesis, crystallization, and/or recrystallization of the compound. "Solvate" includes hydrate which is an association of water with a compound, in the crystalline form.

"Patient" or "subject" refers to mammals and includes humans and non-human mammals.

"Pharmaceutically acceptable salt" refers to pharmaceutically acceptable salts of a compound, which salts are derived from a variety of organic and inorganic counter ions well known in the art and include, by way of example only, when the molecule contains an acidic functionality, salts of organic or inorganic bases, such as sodium, potassium, calcium, magnesium, ammonium, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and tetraalkylammonium, and the like; and when the molecule contains a basic functionality, salts of organic or inorganic acids, such as hydrochloride, hydrobromide, tartrate, mesylate, acetate, maleate, and oxalate. Other non-limiting examples of acids include sulfuric acid, nitric acid, phosphoric acid, propionic acid, glycolic acid, pyruvic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease.

"Effective amount" is intended to mean an amount of an active compound or pharmaceutical agent that elicits the biological or medicinal response in a tissue, system, animal, individual or human that is being sought by a researcher, veterinarian, medical doctor or other clinician, which includes treating a disease.

Drug Derivatives for Conjugation with an Antigen Binding Unit

In one aspect, disclosed herein is a maytansinoid derivative having a linking group capable of conjugating to an antigen binding unit (Abu), by forming a linker that is not acid labile, not peptidase cathepsin sensitive, and does not contain a disulfide bond.

Maytansinoids suitable for attaching the linking group include maytansinol and maytansinol analogues and can be isolated from natural sources according to known methods, produced using biotechnologies (see e.g., Yu et al., 99 PNAS 7968-7973 (2002)), or prepared synthetically according to known methods (see e.g., Cassady et al., Chem. Pharm. Bull. 52(1) 1-26 (2004)).

Certain examples of suitable maytansinol analogues include:

(1) C-19-dechloro (U.S. Pat. No. 4,256,746) (prepared by LAH reduction of ansamytocin P2);
(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using lithium aluminium hydride (LAH));
(3) C-20-demethoxy, C-20-acyloxy (—OCOR), +/−dechloro (U.S. Pat. No. 4,294,757) (prepared by acylation using acyl chlorides);
(4) C-9-SH (U.S. Pat. No. 4,424,219) (prepared by the reaction of maytansinol with $H_2S$ or $P_2S_5$);
(5) C-14-hydroxymethyl($CH_2OH$) or acyloxymethyl ($CH_2OC(=O)$phenyl or $CH_2OC(=O)(C_1$-$C_5$ alkyl)) (U.S. Pat. No. 4,331,598) (prepared from *Nocardia*);
(6) C-15-hydroxy/acyloxy (U.S. Pat. No. 4,364,866) (prepared by the conversion of maytansinol by *Streptomyces*);
(7) C-15-methoxy (U.S. Pat. Nos. 4,313,946 and 4,315,929) (isolated from *Trewia nudlflora*);
(8) C-18-N-demethyl (U.S. Pat. Nos. 4,362,663 and 4,322,348) (prepared by the demethylation of maytansinol by *Streptomyces*); and
(9) 4,5-deoxy (U.S. Pat. No. 4,371,533) (prepared by the titanium trichloride/LAH reduction of maytansinol).

Many positions on maytansinol can be useful as the linkage position, depending upon the type of linker. For example, for forming an ester linkage, the C-3 position having a hydroxyl group, the C-14 position modified with hydroxymethyl, the C-15 position modified with a hydroxyl group and the C-20 position having a hydroxyl group are all suitable. In some embodiments, the linkage position is the C-3 position.

In some embodiments, provided herein is a maytansinoid derivative of Formula I or I-1:

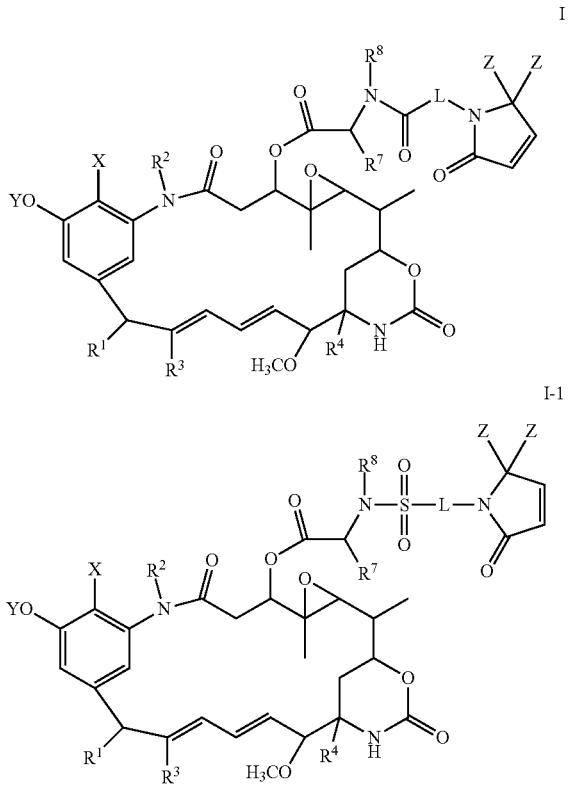

or a salt thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2OH$, or —$CH_2C(=O)R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
each Z is independently hydrogen or $C_1$-$C_4$ alkyl, or the two Z with the carbon atom to which they are attached form a C=O; and
L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8$C(=O)—, —$SO_2NR^8$—, or —$NR^8SO_2$—; preferably L is —$(CH_2)_m$—, wherein m is selected from an integer of 1 to 20, preferably 1 to 10, more preferably 5 to 10;
substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each R$^{11}$ is independently hydrogen, alkyl, aryl, cycloalkyl, cycloalkenyl, heteroaryl, and heterocyclic, or the two R$^{11}$ together with the nitrogen form a heterocyclic, wherein the heterocyclic is optionally substituted with one or two oxo.

In some embodiments, the compound of Formula I is

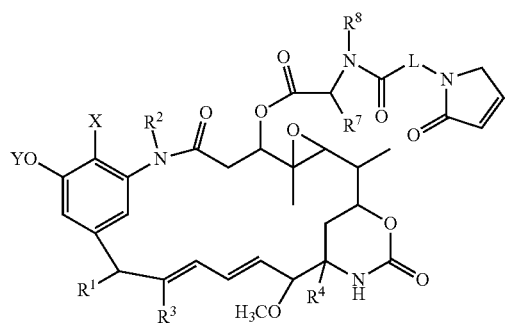

or

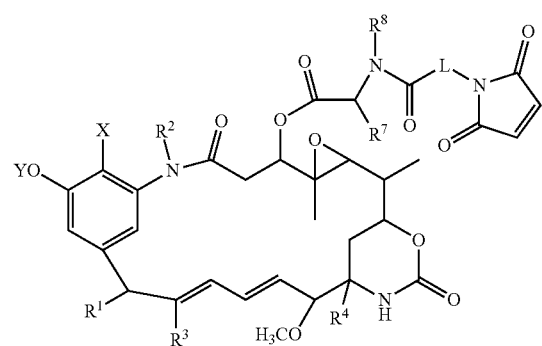

In some embodiments, the compound of Formula I-1 is

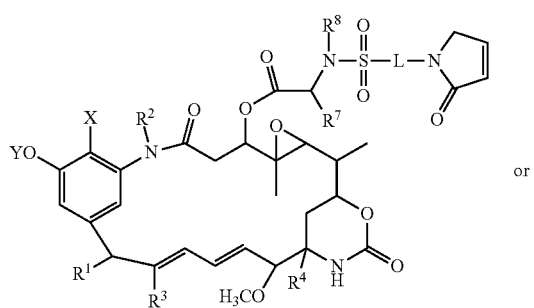

or

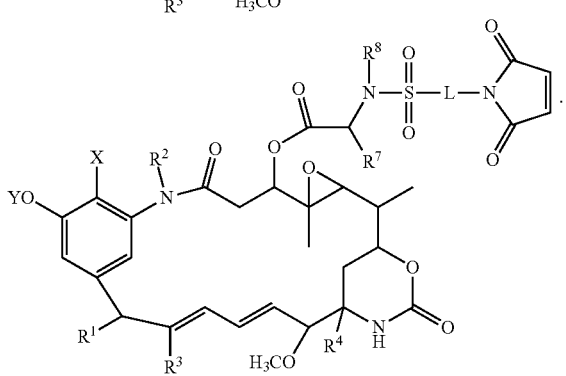

In some embodiments, the compound of Formula I is the isomer:

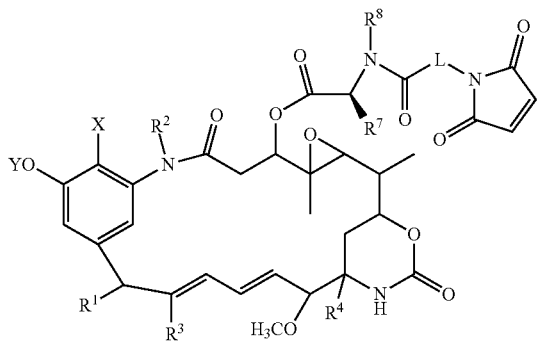

In some embodiments, the compound of Formula I-1 is the isomer:

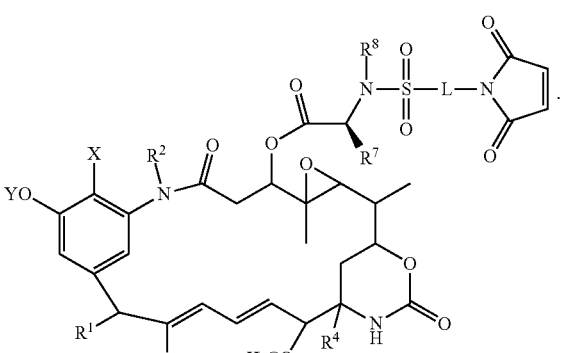

In some embodiments, provided herein is a maytansinoid derivative of Formula II or II-1.

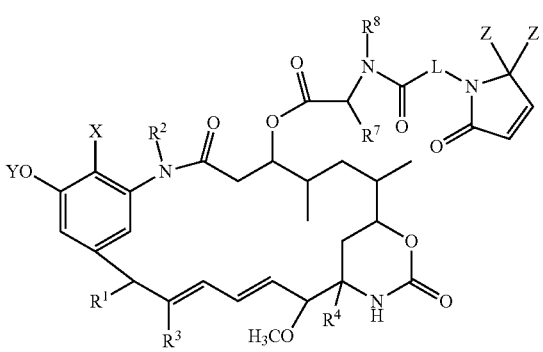

19
-continued

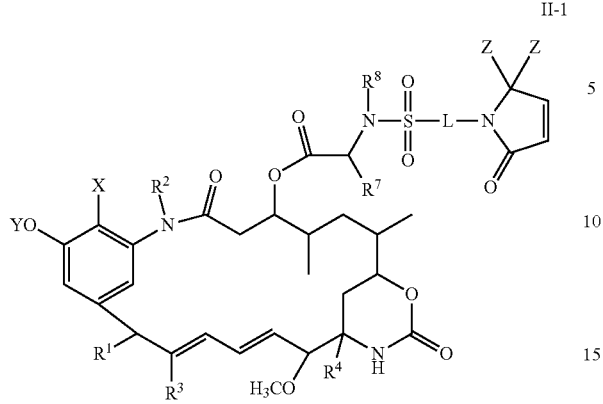

II-1 or a salt thereof, wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —CH$_2$OH, or —CH$_2$C(=O)$R^6$;

$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_{1-6}$ alkyl;

each Z is independently hydrogen or $C_1$-$C_4$ alkyl, or the two Z with the carbon atom to which they are attached form a C=O; and L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —N$R^8$—, —C(O)—, —C(=O)N$R^8$—, —N$R^8$C(=O)—, —SO$_2$N$R^8$—, or —N$R^8$SO$_2$—; Preferably L is —(CH$_2$)$_m$—, wherein m is selected from an integer of 1 to 20, preferably 1 to 10, more preferably 5 to 10;

substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo.

20

In some embodiments, the compound of Formula II is

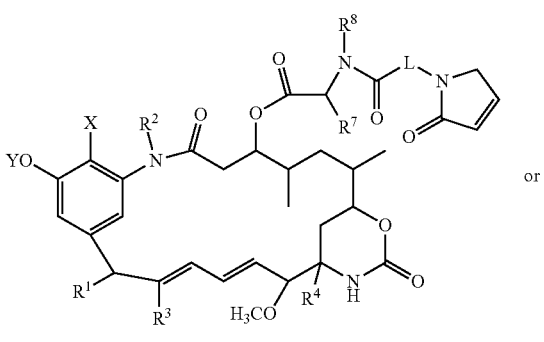

or

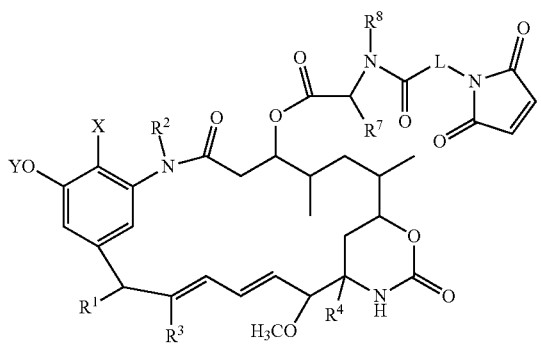

In some embodiments, the compound of Formula II-1 is

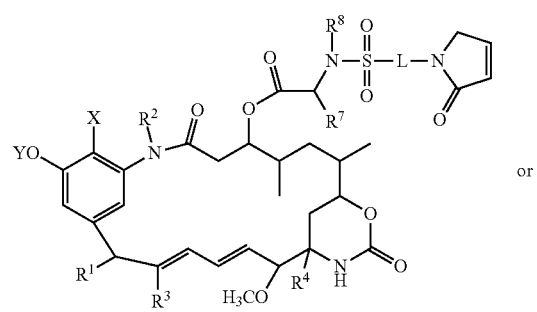

or

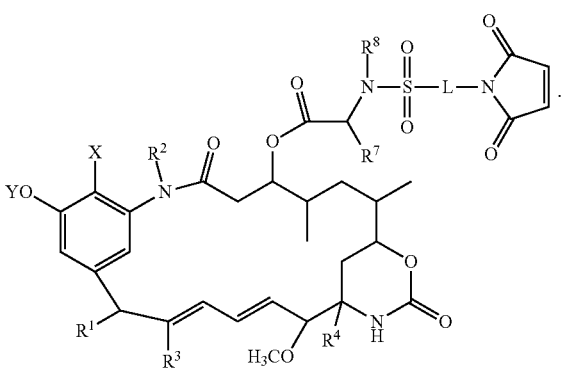

In some embodiments, the compound of Formula II is the isomer:

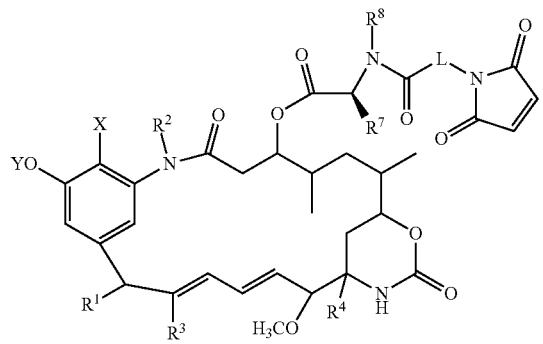

In some embodiments, the compound of Formula II-1 is the isomer:

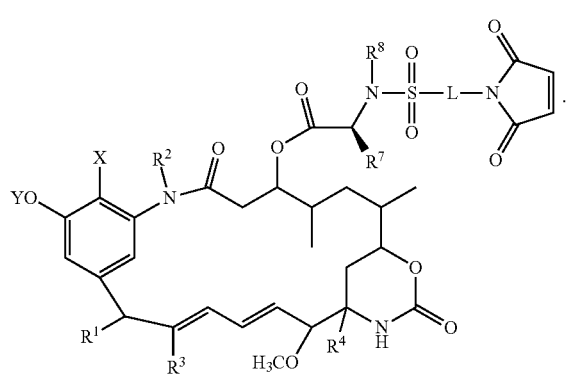

In some embodiments, X is hydrogen. In some embodiments, X is chloro. In some embodiments, Y is hydrogen. In some embodiments, $R^1$ is hydrogen. In some embodiments, $R^2$ is methyl. In some embodiments, $R^3$ is methyl. In some embodiments, $R^4$ is —OH. In some embodiments, $R^7$ is an amino acid side chain. In some embodiments, $R^7$ is methyl. In some embodiments, $R^8$ is methyl.

In some embodiments, L is unsubstituted $C_1$-$C_{20}$ alkylene. In some embodiments, L is substituted $C_1$-$C_{20}$ alkylene. In some embodiments, L is unsubstituted $C_1$-$C_{10}$ alkylene. In some embodiments, L is substituted $C_1$-$C_{10}$ alkylene. In some embodiments, L is —(CH$_2$)$_5$—. In some embodiments, L is unsubstituted $C_1$-$C_{20}$ alkylene wherein one or two of the —CH$_2$— groups are independently replaced with $C_3$-$C_8$ cycloalkylene, —O—, —S—, —NR$^8$—, —C(=O)NR$^8$—, —NR$^8$C(=O)—, —SO$_2$NR$^8$—, or —NR$^8$SO$_2$—. In some embodiments, L is substituted $C_1$-$C_{20}$ alkylene wherein one or two of the —CH$_2$— groups are independently replaced with $C_3$-$C_8$ cycloalkylene, —O—, —S—, —NR$^8$—, —C(=O)NR$^8$—, —NR$^8$C(=O)—, —SO$_2$NR$^8$—, or —NR$^8$SO$_2$—. In some embodiments, when more than one —CH$_2$— groups are replaced, the —CH$_2$— groups are not adjacent to each other.

In some embodiments, provided is a compound of Formula III or III-1:

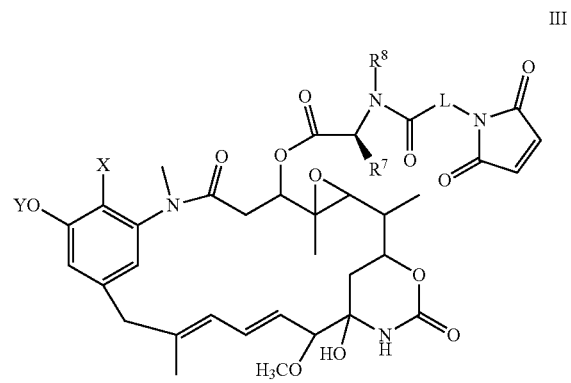

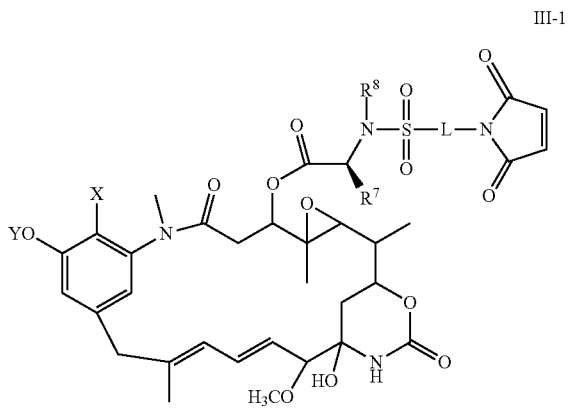

or a salt thereof,
wherein
X is H or Cl;
Y is H or methyl;
$R^7$ is hydrogen, $C_1$-$C_6$ alkyl or an amino acid side chain;
$R^8$ is hydrogen or $C_1$-$C_6$ alkyl; and
L is selected from $C_1$-$C_{20}$ alkylene, $C_3$-$C_8$ cycloalkylene, and $C_1$-$C_{20}$ alkylene wherein one or more of the —CH$_2$— groups are independently replaced with $C_3$-$C_8$ cycloalkylene, —O—, —S—, —NR$^8$—, —C(=O)NR$^8$—, —NR$^8$C(=O)—, —SO$_2$NR$^8$—, or —NR$^8$SO$_2$—.

In some embodiments, the compound is of Formula IV or IV-1:

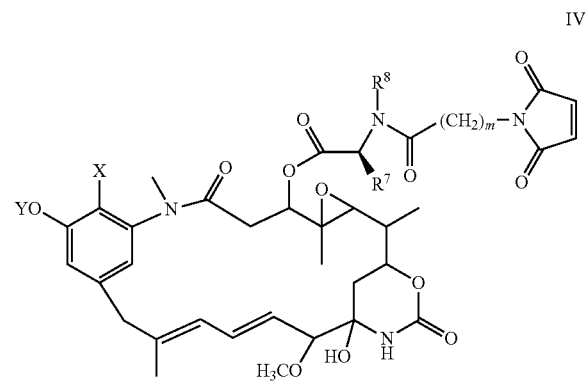

-continued

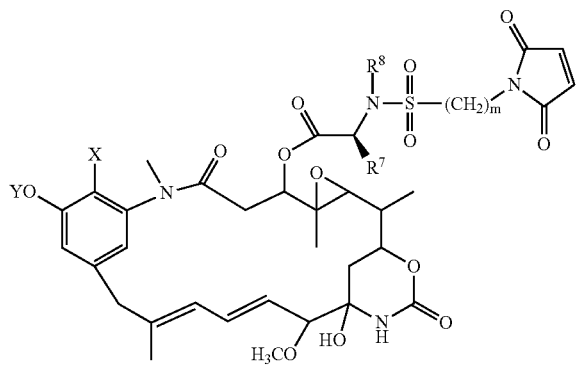

or a salt thereof,
wherein
  X is H or Cl;

Y is H or methyl;

$R^7$ is hydrogen, $C_1$-$C_6$ alkyl or an amino acid side chain;

$R^8$ is hydrogen or $C_1$-$C_6$ alkyl; and m is selected from an integer of 1 to 20, preferably 1 to 10, more preferably 5 to 10.

In some embodiments, the compound is $N_2$-deacetyl-$N_2$-(6-maleimido-1-oxo-hexyl)maytansine, named batansine, or a salt thereof. Batansine is represented by Formula V:

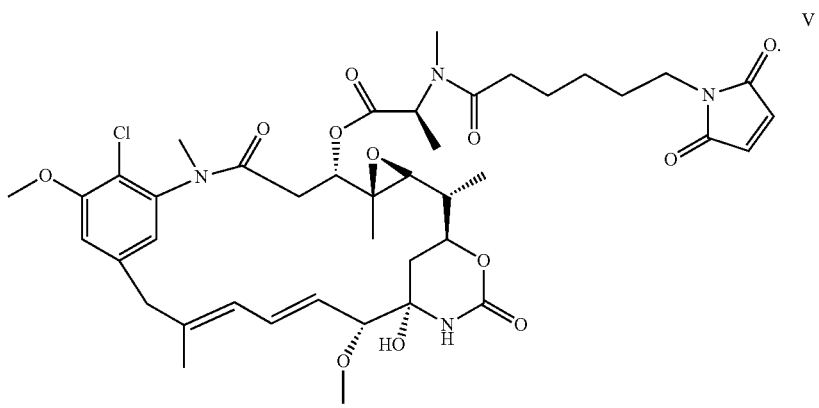

In some embodiments, the compound of Formula I or I-1 is selected from:

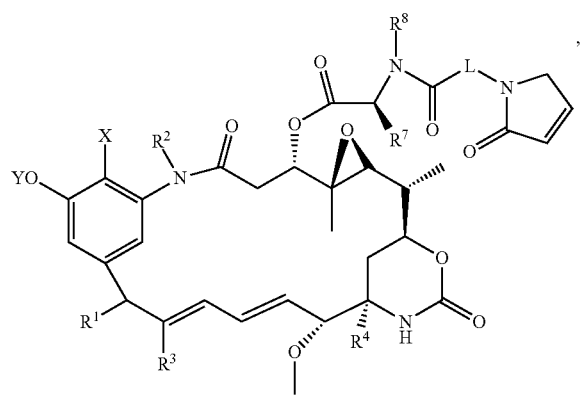

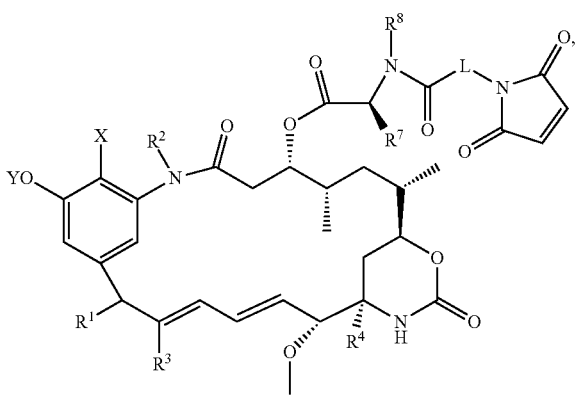

25 26
-continued
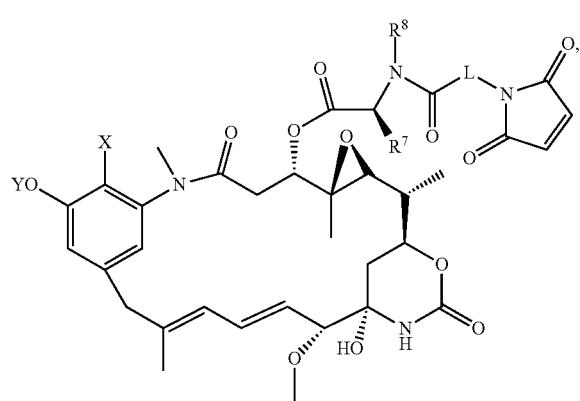
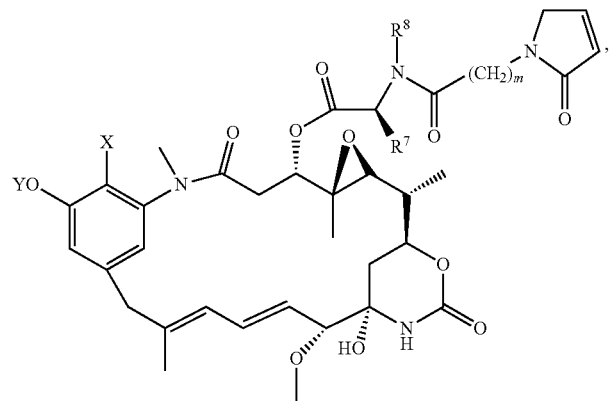
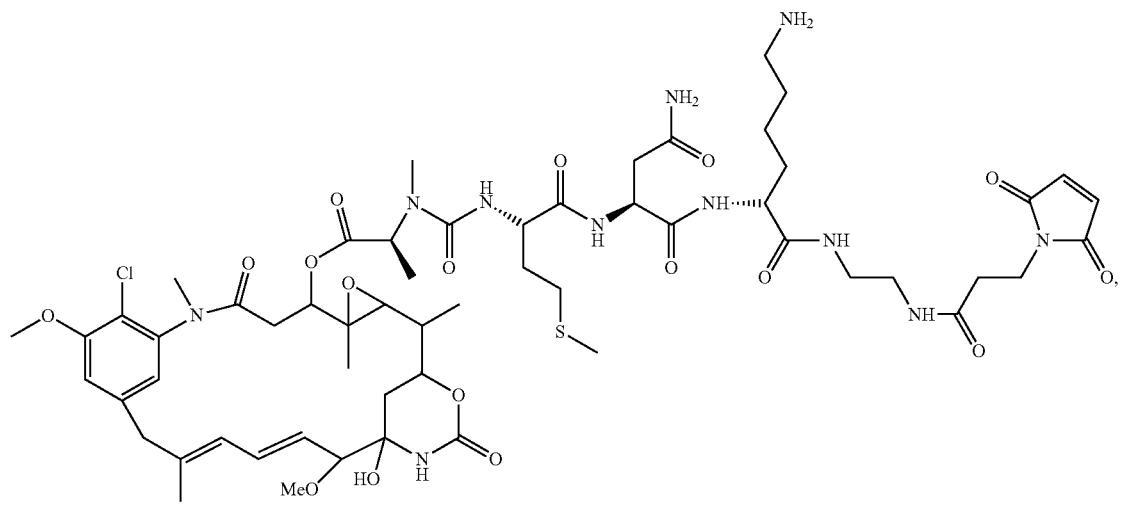
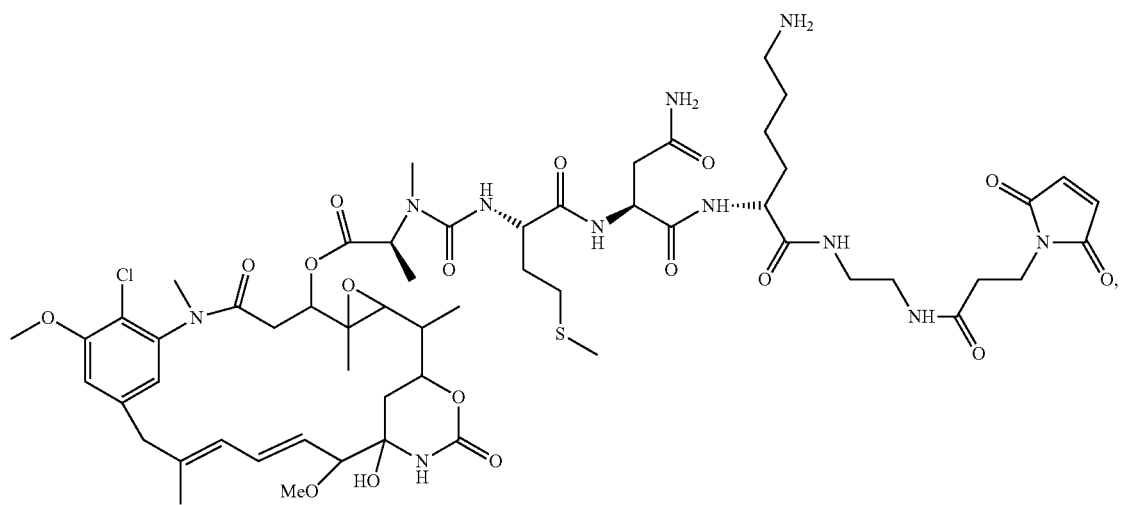

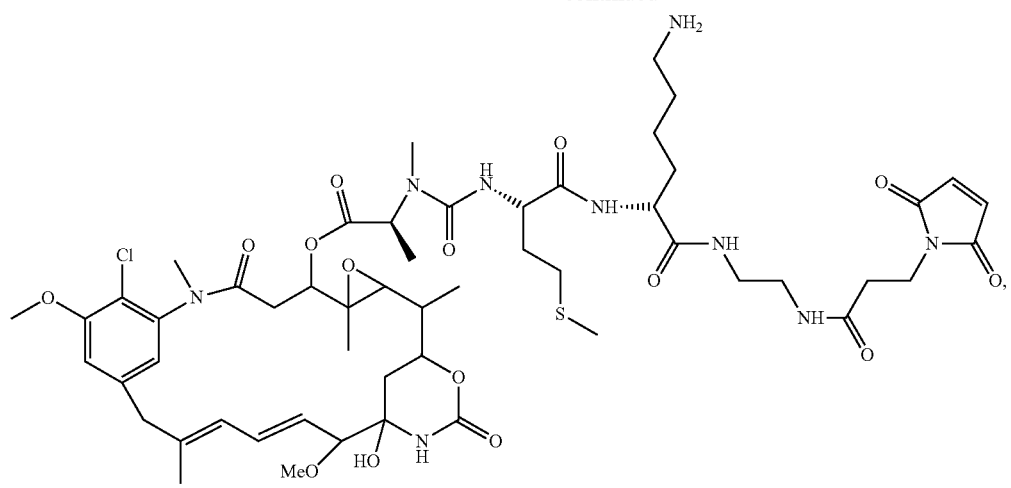
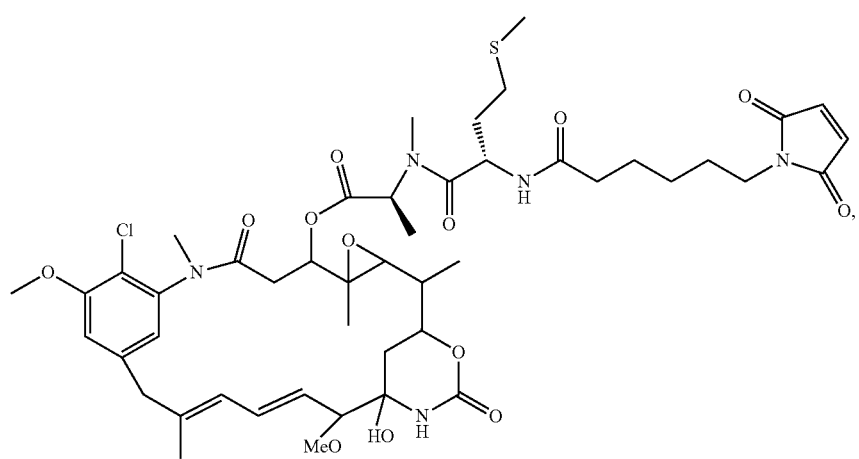
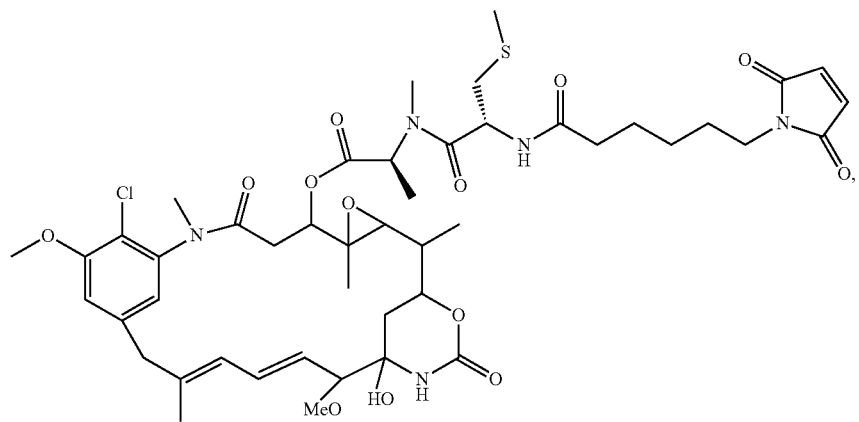

-continued
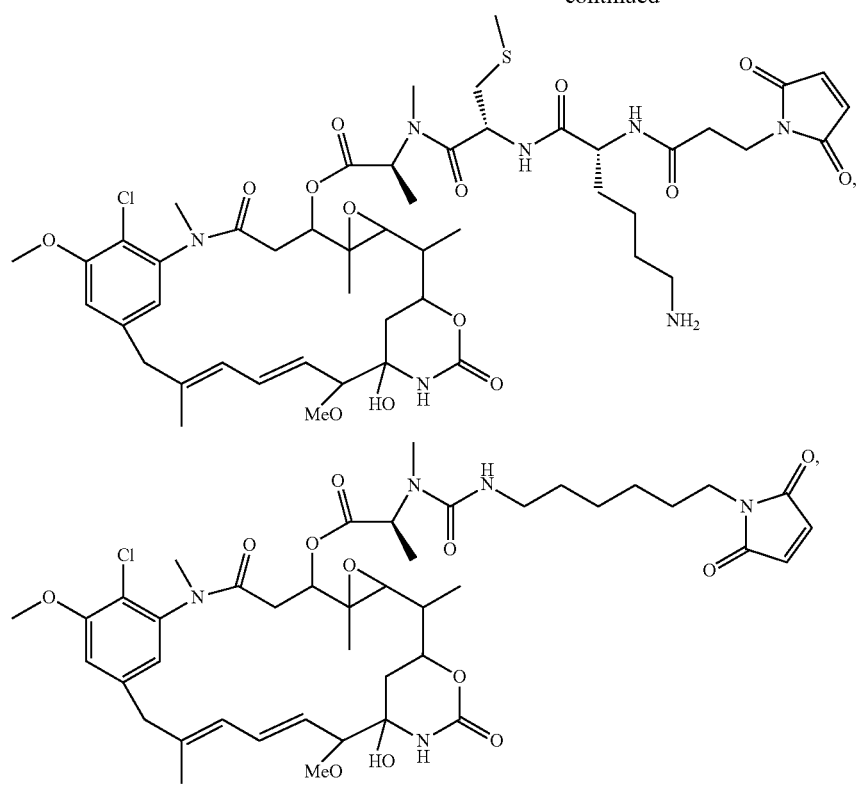
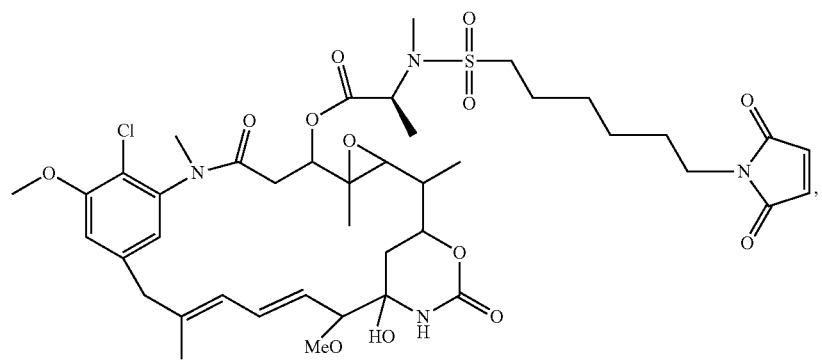
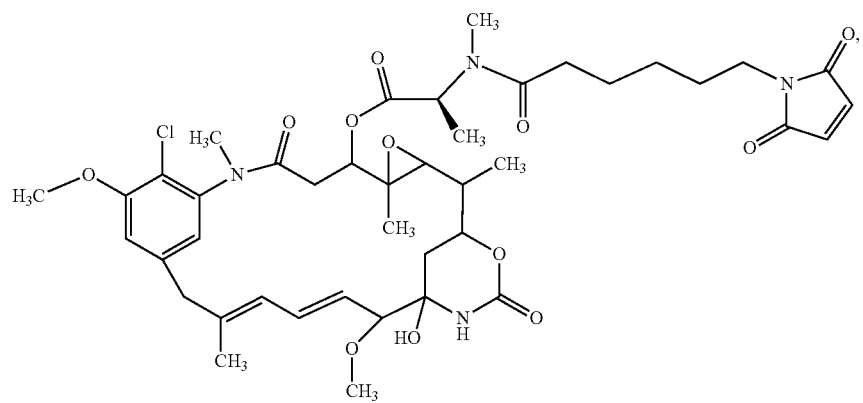

-continued
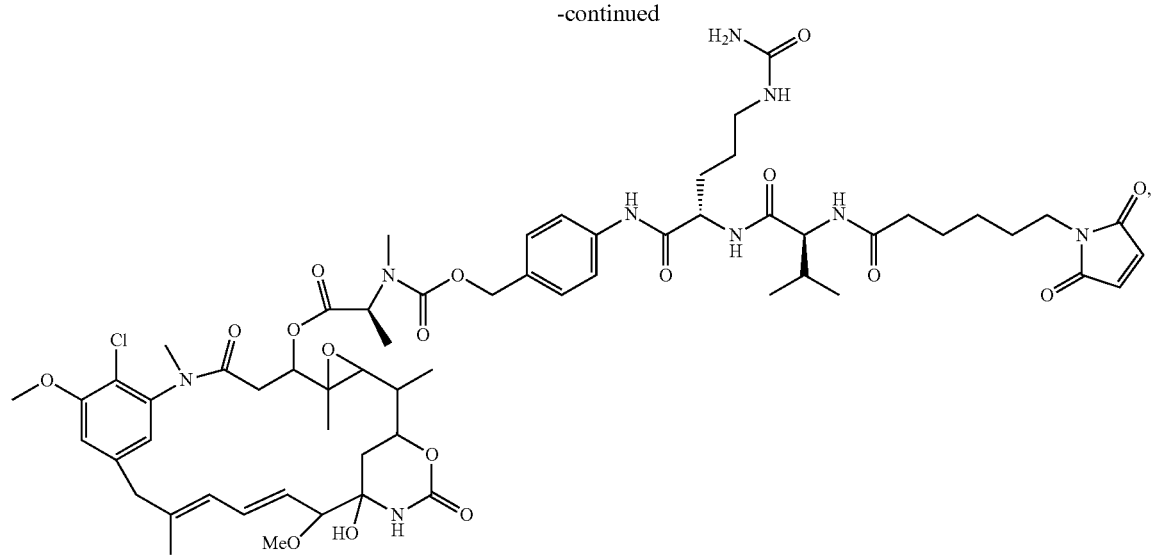
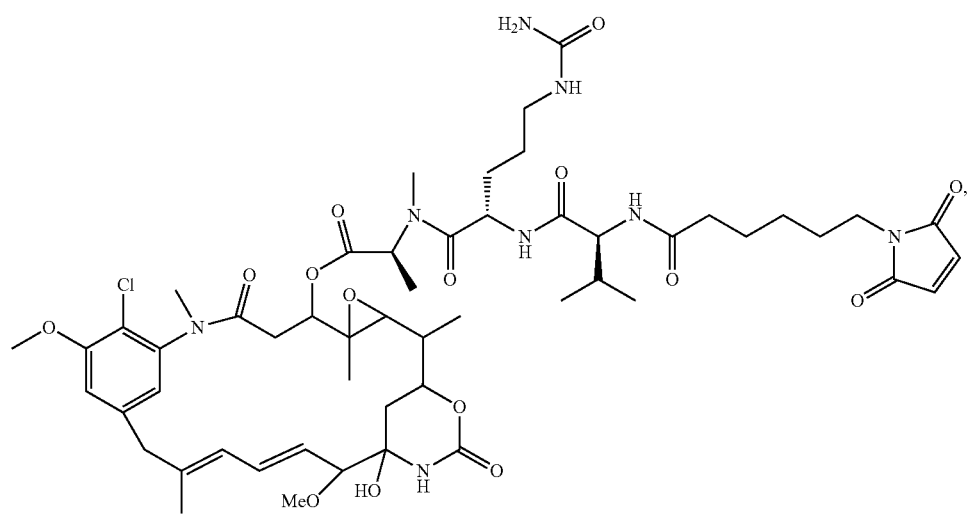
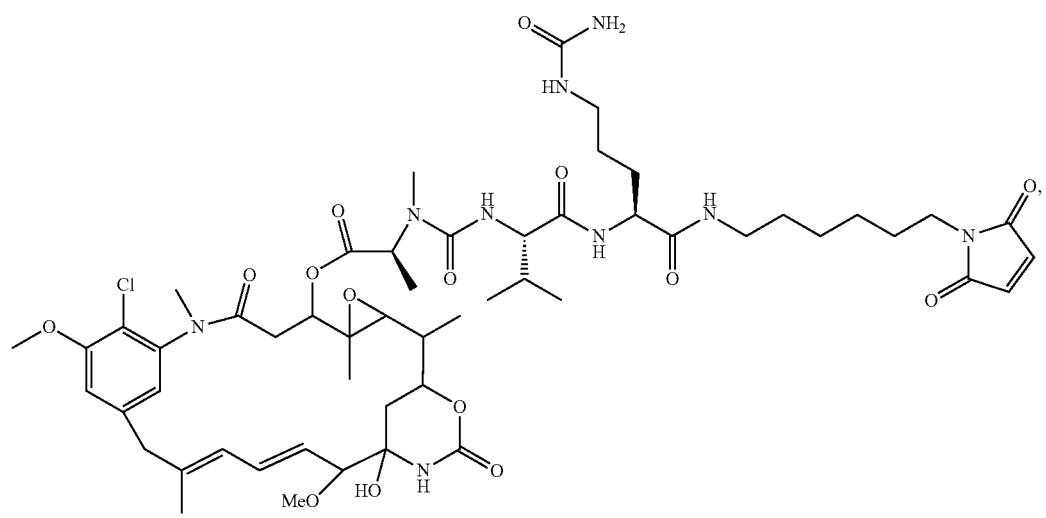

-continued

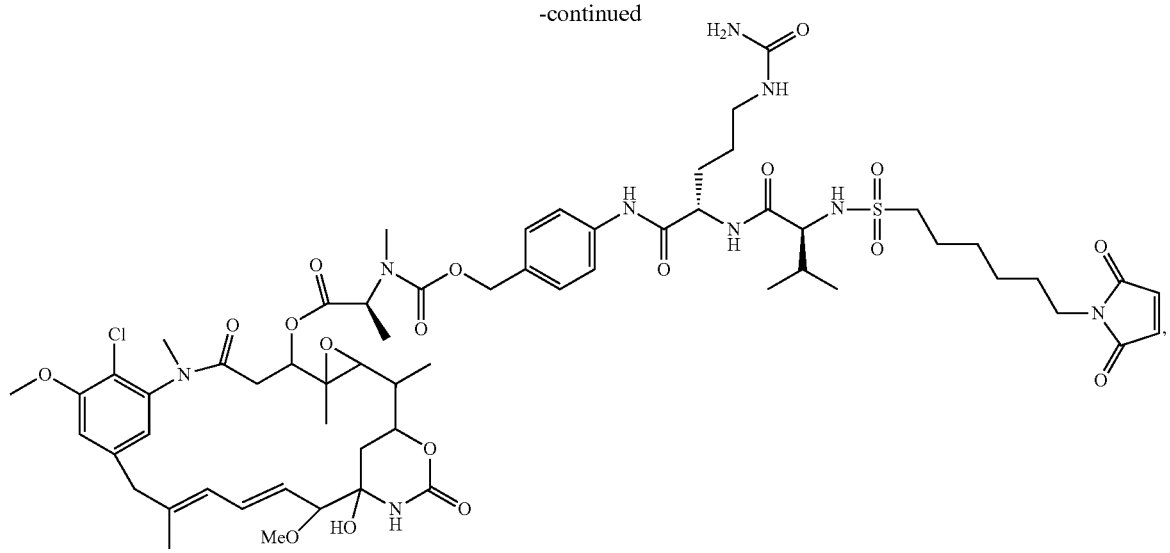

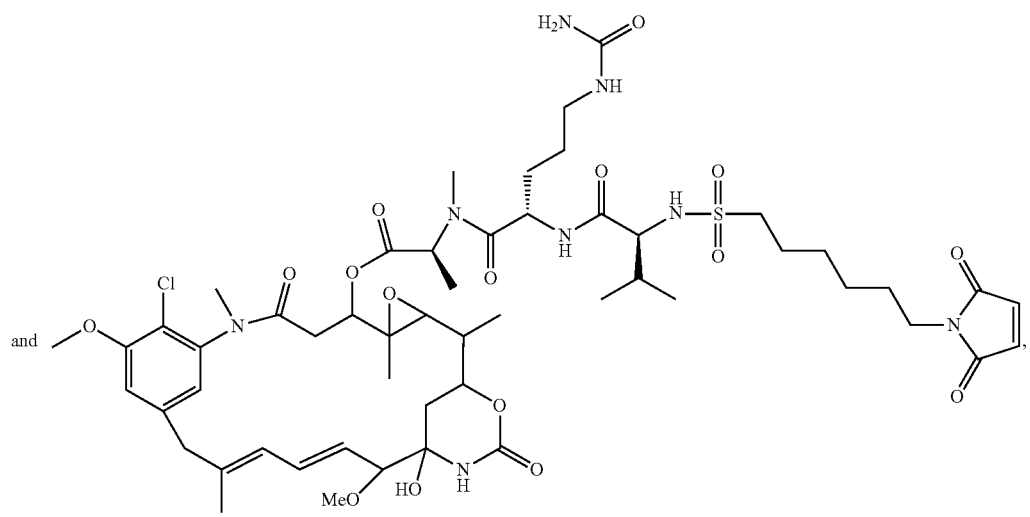 [SMILES: COc1cc2cc(c1Cl)N(C)C(=O)CC(OC(=O)[C@H](C)N(C)C(=O)[C@H](CCCNC(N)=O)NC(=O)[C@@H](NS(=O)(=O)CCCCCCN1C(=O)C=CC1=O)C(C)C)C1(C)OC1C(C)C1CC(O)(NC(=O)O1)C(OC)/C=C/C=C(\C)C2]

or a salt thereof.

Drug Linker Antigen Binding Unit Conjugates

In another aspect, disclosed herein is a maytansinoid conjugated with an antigen binding unit (Abu) via a linker (drug linker Abu conjugate).

In exemplary embodiments, the drug linker Abu conjugate is a maytansinoid conjugated to an antibody via a linker that is neither acid-labile, cathepsin sensitive, nor containing a disulfide bond.

In some embodiments, provided herein is a maytansinoid linker antigen binding unit conjugate of Formula Ia or Ia-1:

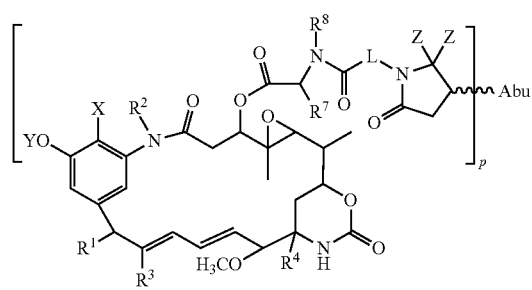

-continued

[Structure Ia-1]

or a pharmaceutically acceptable salt or solvate thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
p is selected from 1, 2, 3, 4, 5, 6, 7, 8, 9, and 10;
each Z is independently hydrogen or $C_1$-$C_4$ alkyl, or the two Z with the carbon atom to which they are attached form a C=O;
L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8$C(=O)—, —$SO_2NR^8$—, or —$NR^8SO_2$—; Preferably L is —$(CH_2)_m$—, wherein m is selected from an integer of 1 to 20, preferably 1 to 10, more preferably 5 to 10;
substituted $C_1$-$C_{20}$ alkylene is $C_1$-$C_{20}$ alkylene substituted with 1 to 4 —$SO_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CON$R^{11}R^{11}$, —$CO_2$H, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and
Abu is an antigen binding unit.

In some embodiments, the compound of Formula Ia or Ia-1 is

[Structure] or

[Structure]

In some embodiments, the compound of Formula Ia is:

[Structure]

and the compound of Formula Ia-1 is:

[Structure]

In some embodiments, provided herein is a maytansinoid linker antigen binding unit conjugate of Formula IIa or IIa-1:

IIa

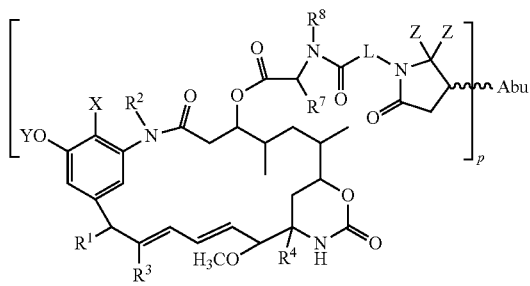

IIa-1

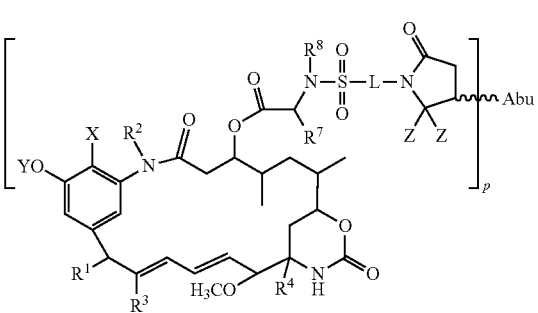

or a pharmaceutically acceptable salt or solvate thereof, wherein

X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
p is selected from 1, 2, 3, 4, 5, 6, 7, 8, 9, and 10;
each Z is independently hydrogen or $C_1$-$C_4$ alkyl, or the two Z with the carbon atom to which they are attached form a C=O;
L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —N$R^8$—, —C(O)—, —C(=O)N$R^8$—, —N$R^8$C(=O)—, —SO$_2$N$R^8$—, or —N$R^8$SO$_2$—; Preferably L is —(CH$_2$)$_m$—, wherein m is selected from an integer of 1 to 20, preferably 1 to 10, more preferably 5 to 10;
substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CON$R^{11}R^{11}$, —CO$_2$H, and —N$R^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and
Abu is an antigen binding unit.

In some embodiments, the compound of Formula IIa or IIa-1 is

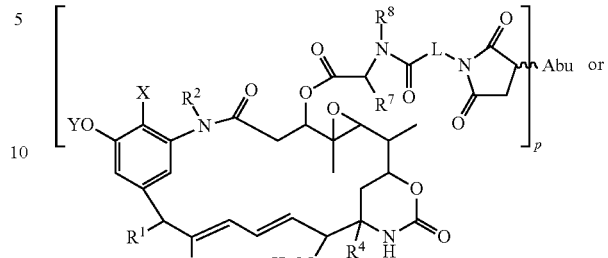

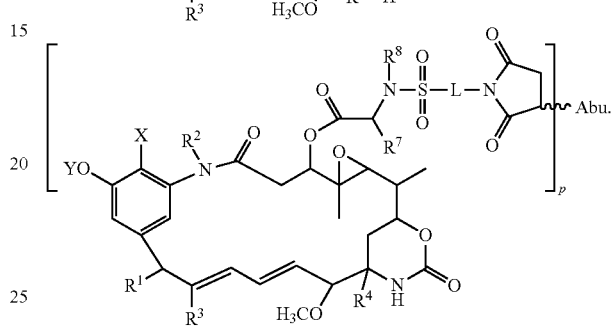

In some embodiments, the compound of Formula IIa is:

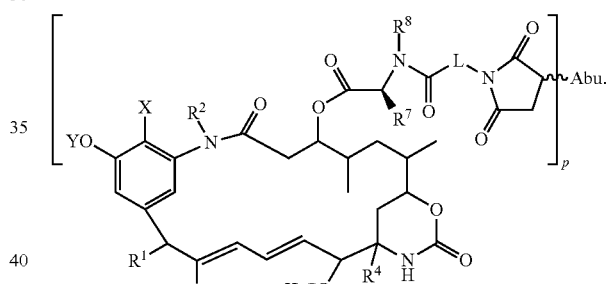

The compound of Formula IIa-1 is:

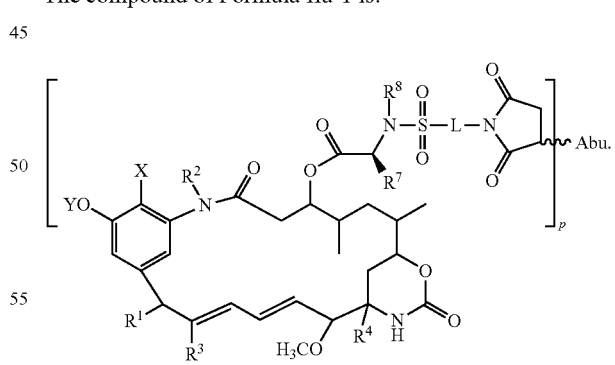

In some embodiments, X is hydrogen. In some embodiments, X is chloro. In some embodiments, Y is hydrogen. In some embodiments, $R^1$ is hydrogen. In some embodiments, $R^2$ is methyl. In some embodiments, $R^3$ is methyl. In some embodiments, $R^4$ is —OH. In some embodiments, $R^7$ is an amino acid side chain. In some embodiments, $R^7$ is methyl. In some embodiments, $R^8$ is methyl.

In some embodiments, L is unsubstituted $C_1$-$C_{20}$ alkylene. In some embodiments, L is substituted $C_1$-$C_{20}$ alkylene. In some embodiments, L is unsubstituted $C_1$-$C_{10}$ alkylene. In some embodiments, L is substituted $C_1$-$C_{10}$ alkylene. In some embodiments, L is —$(CH_2)_5$—. In some embodiments, L is unsubstituted $C_1$-$C_{20}$ alkylene wherein one or two of the —$CH_2$— groups are independently replaced with $C_3$-$C_8$ cycloalkylene, —O—, —S—, —$NR^8$—, —C(=O)$NR^8$—, —$NR^8$C(=O)—, —$SO_2NR^8$—, or —$NR^8SO_2$—. In some embodiments, L is substituted $C_1$-$C_{20}$ alkylene wherein one or two of the —$CH_2$— groups are independently replaced with $C_3$-$C_8$ cycloalkylene, —O—, —S—, —$NR^8$—, —C(=O)$NR^8$—, —$NR^8$C(=O)—, —$SO_2NR^8$—, or —$NR^8SO_2$—. In some embodiments, when more than one —$CH_2$— groups are replaced, the replaced —$CH_2$— groups are not adjacent to each other.

In some embodiments, provided is a compound of Formula IIIa or IIIa-1:

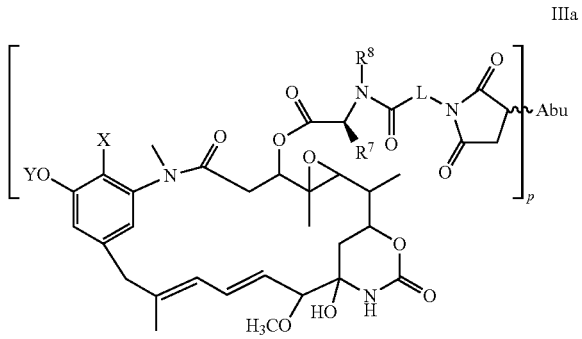

IIIa

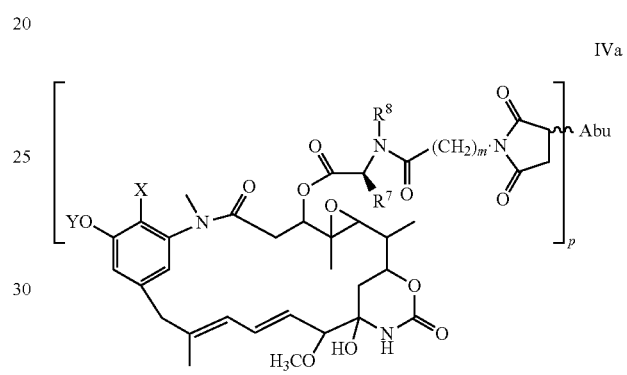

or a pharmaceutically acceptable salt or solvate thereof, wherein
  X is H or Cl;
  Y is H or methyl;
  $R^7$ is hydrogen, $C_1$-$C_6$ alkyl or an amino acid side chain;
  $R^8$ is hydrogen or $C_1$-$C_6$ alkyl;
  p is selected from 1, 2, 3, 4, 5, 6, 7, 8, 9, and 10;
  L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8$C(=O)—, —$SO_2NR^8$—, or —$NR^8SO_2$—; preferably L is —$(CH_2)_m$—, wherein m is selected from an integer of 1 to 20, preferably 1 to 10, more preferably 5 to 10;

substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and
  Abu is an antigen binding unit.

In some embodiments, the compound is of Formula IVa or IVa-1:

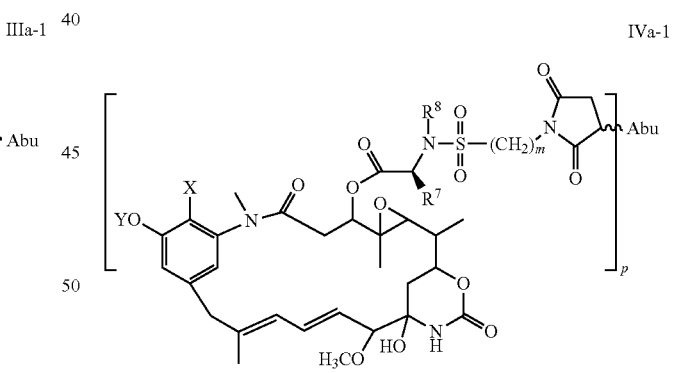

or a pharmaceutically acceptable salt or solvate thereof, wherein
  X is H or Cl;
  Y is H or methyl;
  $R^7$ is hydrogen, $C_1$-$C_6$ alkyl or an amino acid side chain;
  $R^8$ is hydrogen or $C_1$-$C_6$ alkyl;
  p is selected from 1, 2, 3, 4, 5, 6, 7, 8, 9, and 10;
  m is selected from an integer of 1 to 20, preferably 1 to 10, more preferably 5 to 10; and
  Abu is an antigen binding unit.

In some embodiments, the compound is of Formula Va:
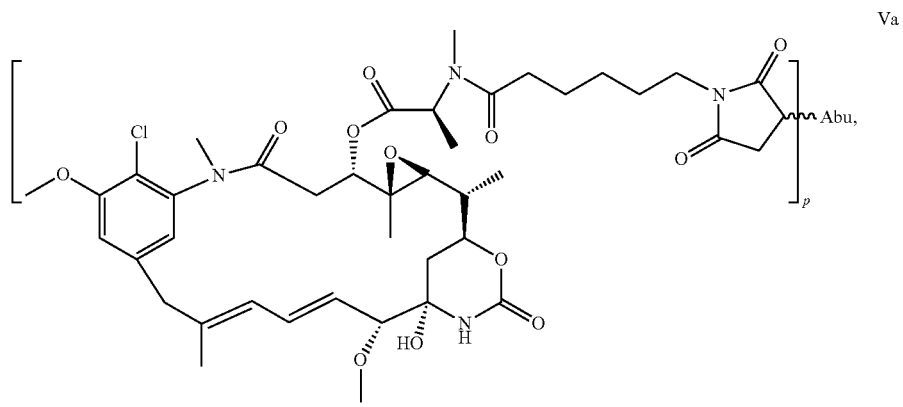
or a pharmaceutically acceptable salt or solvate thereof.
In some embodiments, the compound of Formula Ia or Ia-1 is selected from:
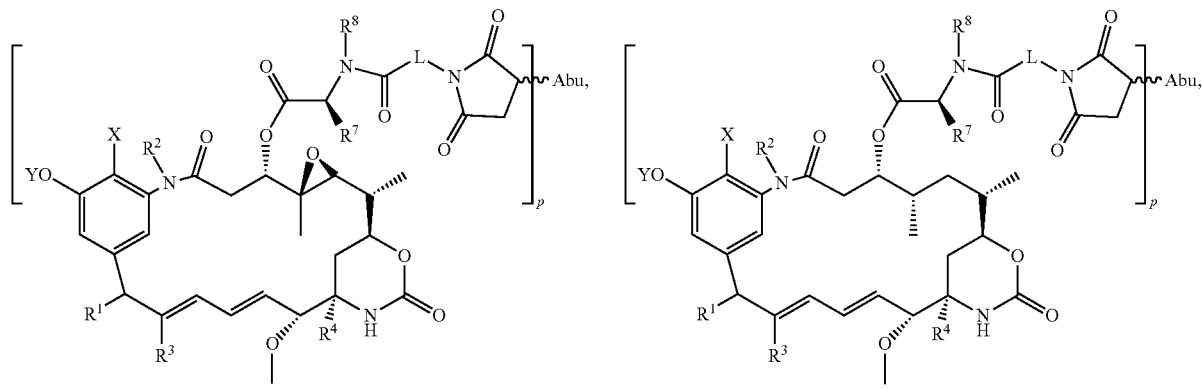
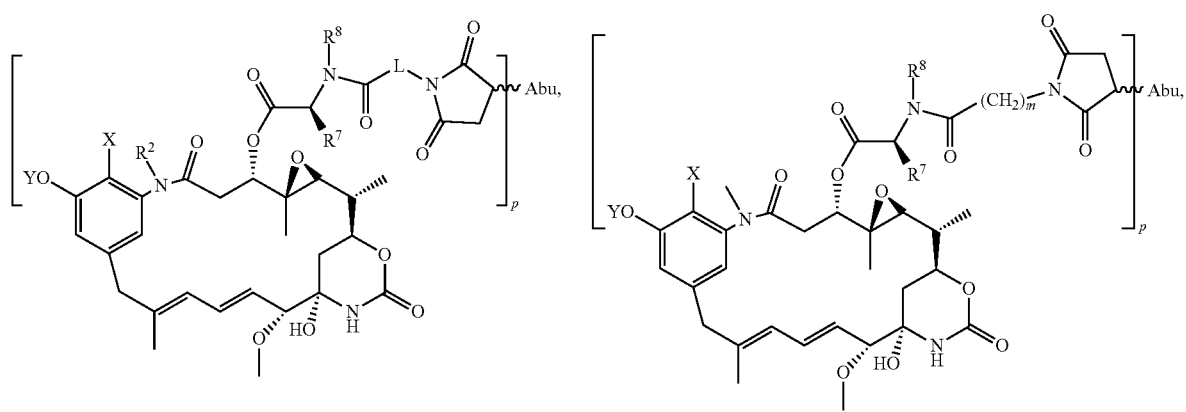

VIa
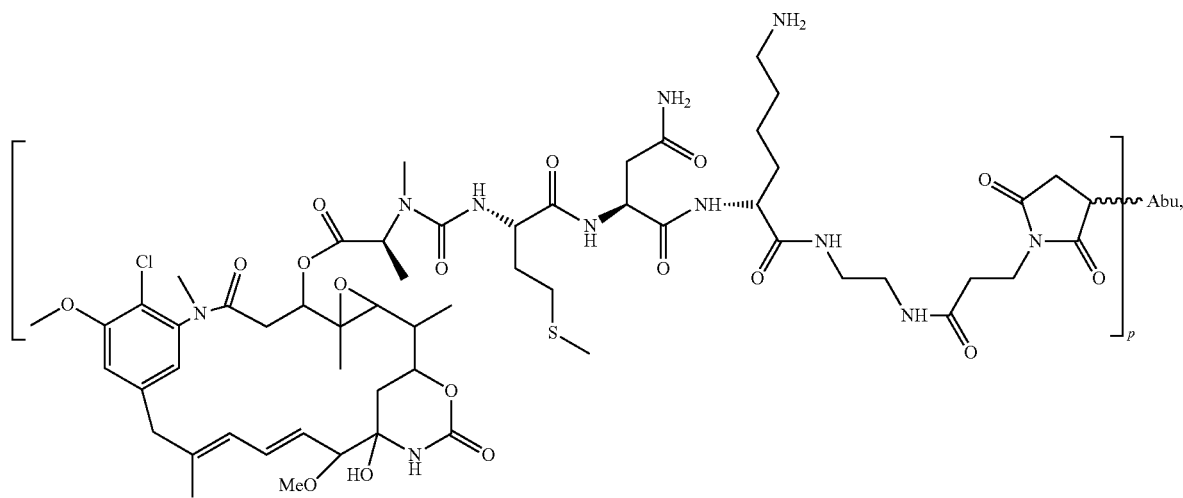
VIIa
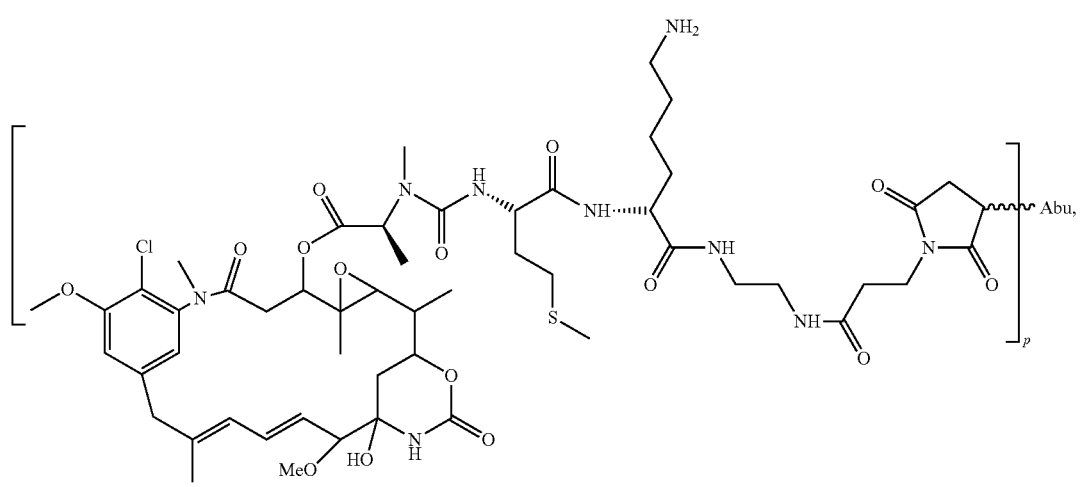
VIIIA
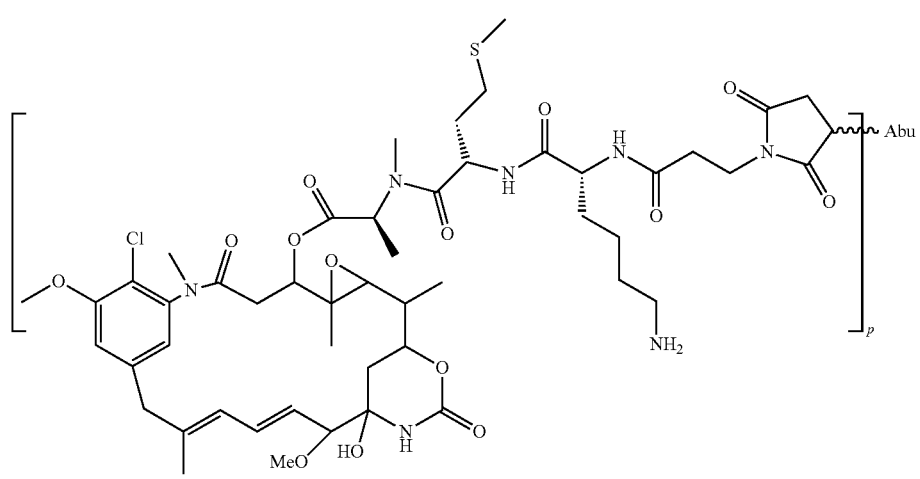

-continued
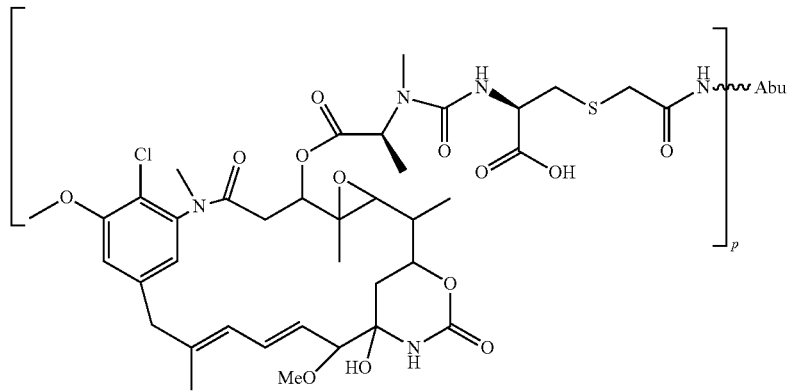
IXa
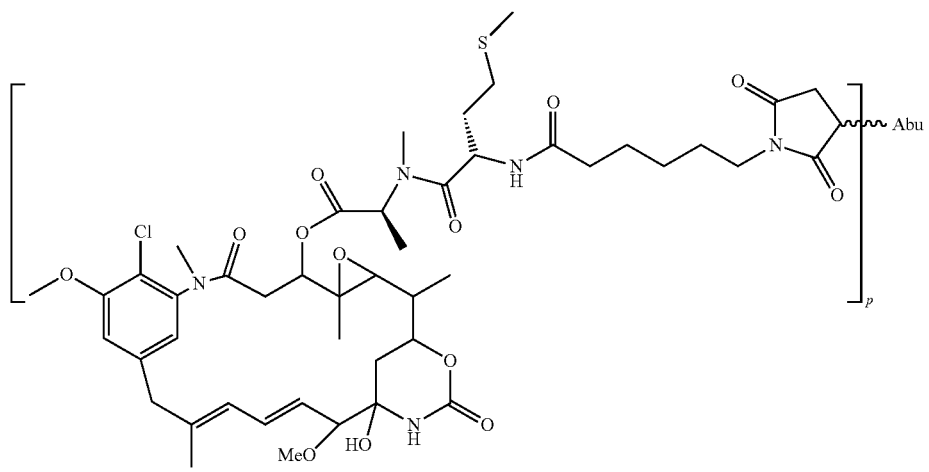
Xa
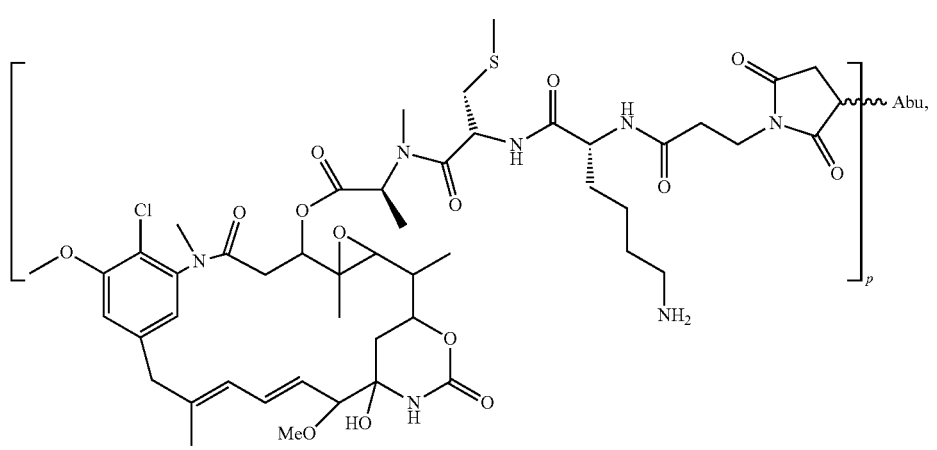
XIa

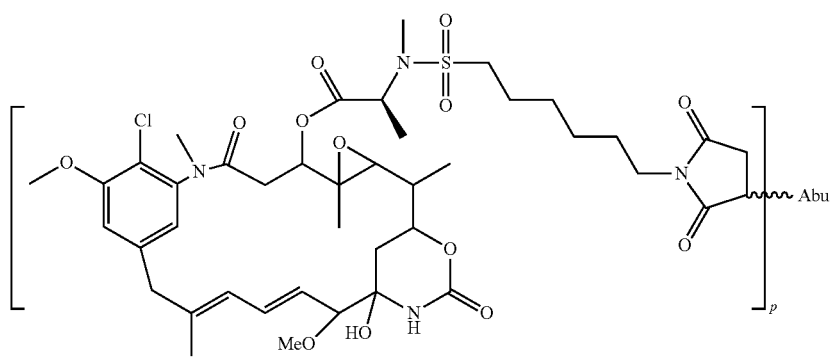
Va-1
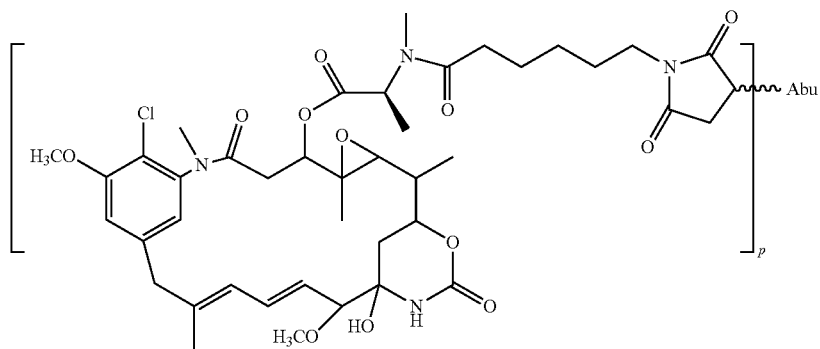
Va
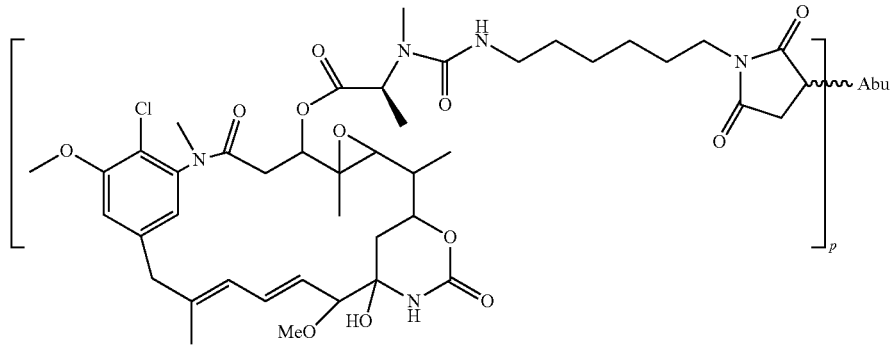
XIIa
In some embodiments, the compound of Formula Ia or Ia-1 is selected from:
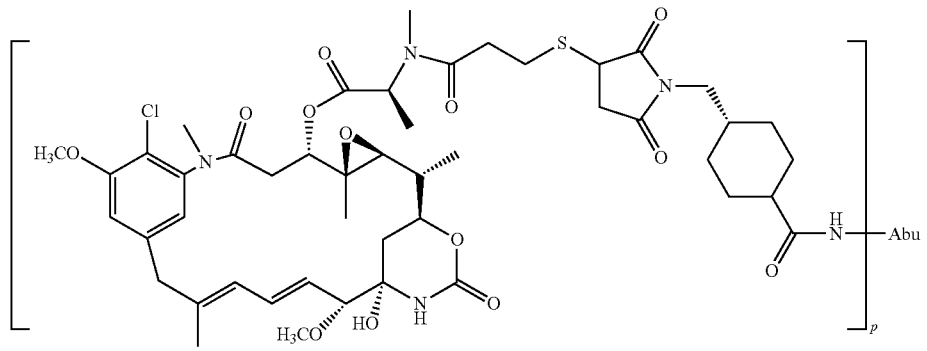
XIVa -continued
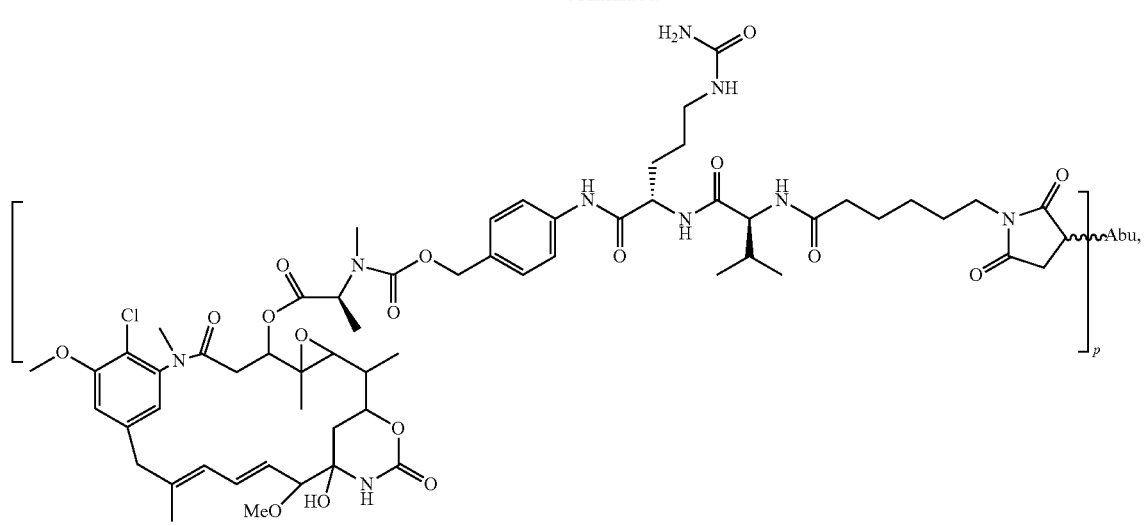
XVa
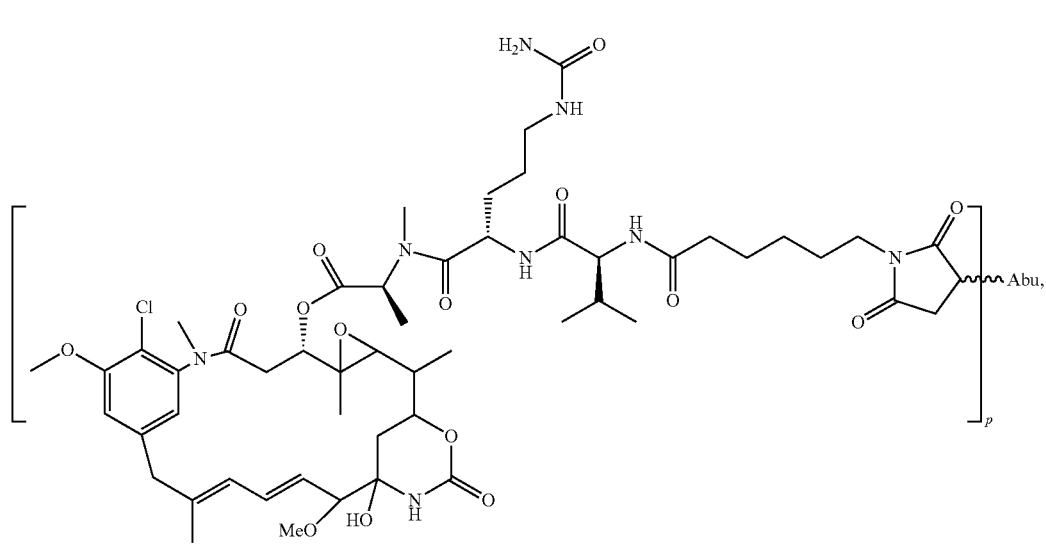
XVIa
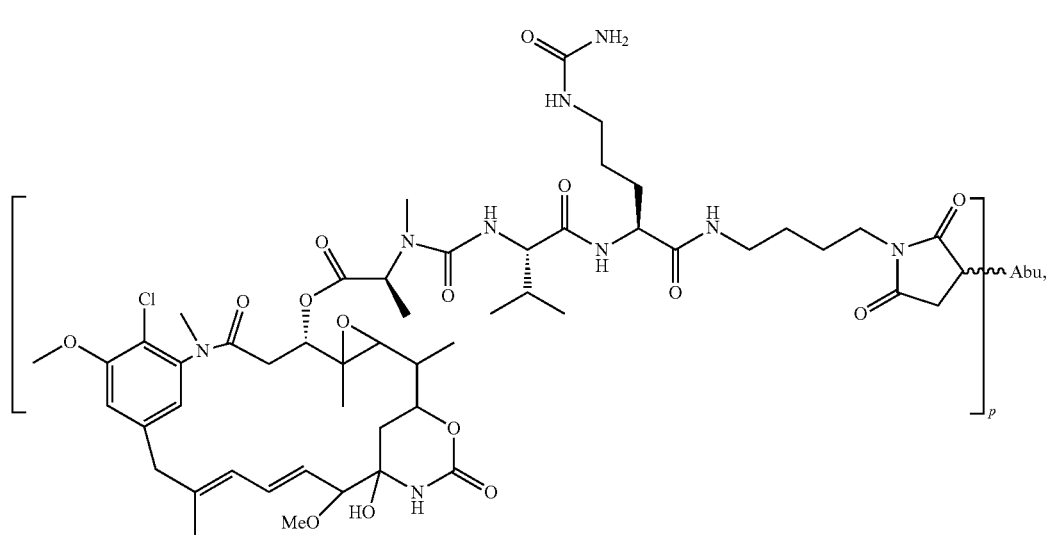
XVIIa

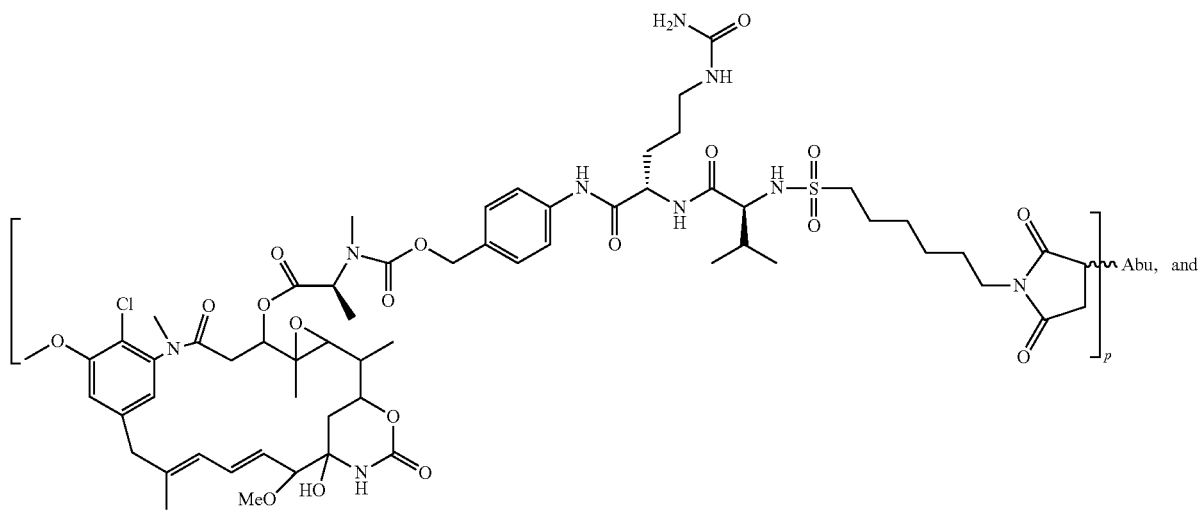

XVIIIa

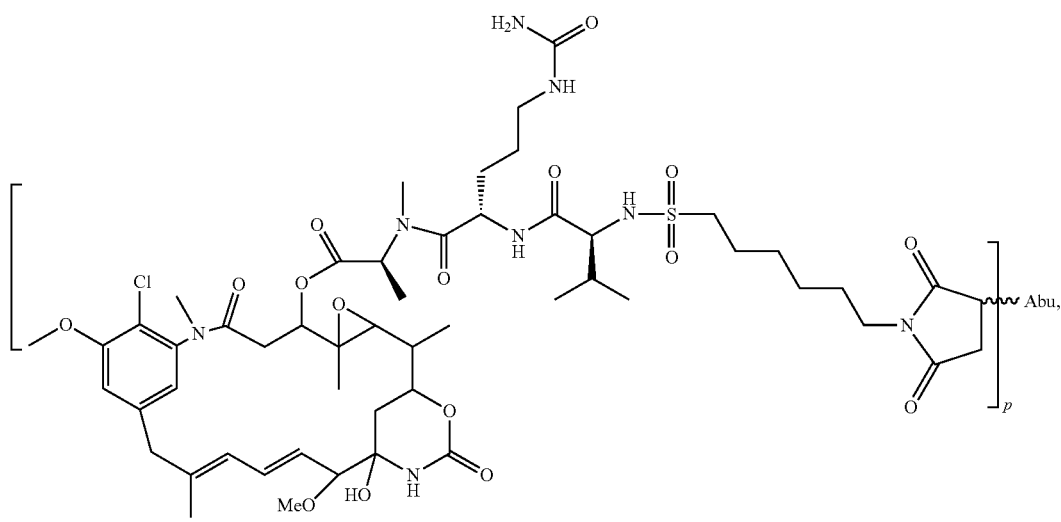

XIXa or a pharmaceutically acceptable salt thereof.

The maytansinoid component of the maytansinoid derivatives having a linking group capable of conjugating to an antigen binding unit (Abu) or the maytansinoid linker antigen binding unit conjugates can be substituted by other suitable cytotoxic agents, for example, an auristatin, a DNA minor groove binding agent, a DNA minor groove alkylating agent, an enediyne, a lexitropsin, a duocarmycin, a taxane, a puromycin, a dolastatin, and a vinca alkaloid. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In some embodiments, the cytotoxic agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-3, DM-4, or eleutherobin. Suitable immunosuppressive agents include, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist. In some embodiments, the cytotoxic agent is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, DM-3, DM-4, or netropsin.

The maytansinoid component of the maytansinoid derivatives having a linking group capable of conjugating to an antigen binding unit (Abu) and the maytansinoid linker antigen binding unit conjugates can also be substituted by a suitable immunosuppressive agent, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

Antigen Binding Units

The antigen binding units may be of any kind presently known, or that become known, and include peptides and non-peptides. Generally, these can be antibodies (for example, monoclonal antibodies), lymphokines, hormones, growth factors, vitamins, nutrient-transport molecules (such as transferrin), or any other cell-binding molecules or substances that specifically bind a target, derived from antibodies, antibody fragments, cell specific ligands, derived from peptides, carbohydrates, natural or synthetic chemical compounds; or a pharmaceutically acceptable salt or solvate thereof.

Antigen binding units include ragments of antibodies (polyclonal and monoclonal) such as Fab, Fab', F(ab')$_2$, and Fv (see, e.g., Parham, J. Immunol. 131:2895-2902 (1983); Spring et al., J. Immunol. 113:470-478 (1974); Nisonoff et al., Arch. Biochem. Biophys. 89:230-244 (1960)); domain antibodies (dAbs) and antigen-binding fragments thereof, including camelid antibodies (see, e.g., Desmyter et al., Nature Struct. Biol, 3:752 (1996)); shark antibodies called new antigen receptors (IgNAR) (see, e.g., Greenberg et al., Nature, 374:168 (1995); Stanfield et al. Science 305:1770-1773 (2004)).

Monoclonal antibody techniques allow for the production of antigen binding unit in the form of specific monoclonal antibodies. Particularly well known in the art are techniques for creating monoclonal antibodies produced by immunizing mice, rabbits, or any other mammal with the antigen of interest such as the tumor specific antigens isolated from the target cell. Another method of creating antigen binding unit is using phage libraries of scFv (single chain variable region), specifically human scFv (see, e.g., Griffiths et al., U.S. Pat. Nos. 5,885,793 and 5,969,108; McCafferty et al., WO 92/01047; Liming et al., WO 99/06587), or domain antibodies using yeast selection system (see, e.g., U.S. Pat. No. 7,195,595). In addition, resurfaced antibodies such as those disclosed in U.S. Pat. No. 5,639,641 may also be used, as may chimerized or humanized antibodies.

Selection of a particular antigen binding unit is a matter of choice that depends upon the disease type, cells and tissues that are to be targeted.

In some embodiments, the antigen binding unit is human monoclonal antibody.

Antigen binding units that have specificity to a tumor antigen can be used. A "tumor antigen" as used herein, refers to an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

Hormones and cellular factors can be tumor antigens. Non-limiting examples include lymphokines such as IL-2, IL-3, IL-4, IL-6, hormones such as insulin, thyrotropin releasing hormone (TRH), melanocyte-stimulating hormone (MSH), steroid hormones such as androgens and estrogens; growth factors and colony-stimulating factors such as EGF, TGF-alpha, FGF, VEGF, G-CSF, M-CSF and GM-CSF (see, e.g., Burgess, Immunology Today 5:155-158 (1984)), transferrin (see, e.g., O'Keefe et al., J. Biol. Chem. 260:932-937 (1985)); and vitamins, such as folate.

Antigen binding units having specificity to a protein that is overexpressed on a tumor cell as compared to a corresponding non-tumor cell can also be used. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as cystic fibrosis.

It is contemplated that antigen binding units can be modified to introduce an amino acid sequence having improved antibody-dependent cellular cytotoxicity (ADCC). For instance, an IgG2 antibody can be modified to include an Fc and/or hinge region from an IgG1 antibody to achieve improved ADCC. Examples of IgG1-Fc that mediates improved ADCC, as well as methods of screening for such sequences, are known in the art (e.g., Stewart et al. Protein Eng Des Sel. 24(9):671-8, 2011).

One particular example of such an antigen binding unit, Bat0206, having improved ADCC has been tested in the present disclosure. Bat0206 includes an anti-EGFR light chain having an amino acid sequence of SEQ ID NO: 1 and an anti-EGFR heavy chain having an amino acid sequence of SEQ ID NO: 2. As shown in Table 1, SEQ ID NO NO: 2 includes a fragment (not underlined) derived from an IgG2 antibody which is fused with an Fc fragment of an IgG1 antibody (underlined and bold).

TABLE 1

Amino acid sequences of exemplifying antigen binding units

| SEQ ID NO: | Amino acid sequence and name |
|---|---|
| 1 | Bat0202 (Anti-EGFR Light Chain 1)<br>DIQMTQSPSSLSASVGDRVTITCQASQDISNYLNWYQQKPGKAPKLLIYD<br>ASNLETGVPSRFSGSGSGTDFTFTISSLQPEDIATYFCQHFDHLPLAFGG<br>GTKVEIKRTVAAPSVFIFPPSDEQLKSGTASVVCLLNNFYPREAKVQWKV |

TABLE 1-continued

Amino acid sequences of exemplifying antigen binding units

| SEQ ID NO: | Amino acid sequence and name |
|---|---|
| | DNALQSGNSQESVTEQDSKDSTYSLSSTLTLSKADYEKHKVYACEVTHQG LSSPVTKSFNRGEC |
| 2 | Bat0204 (Anti-EGFR heavy Chain 1)<br>QVQESGPGLVKPSETLSLTCTVSGGSVSSGDYYWTWIRQSPGKGLEWIGH IYYSGNTNYNPSLKSRLTISIDTSKTQFSLKLSSVTAADTAIYYCVRDRV TGAFDIWGQGTLVIVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK |
| 3 | Cetuximab Light Chain<br>DILLTQSPVILSVSPGERVSFSCRASQSIGTNIHWYQQRTNGSPRLLIKY ASESISGIPSRFSGSGSGTDFTLSINSVESEDIADYYCQQNNNWPTTFGA GTKLELKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGA |
| 4 | Cetuximab heavy Chain<br>QVQLKQSGPGLVQPSQSLSITCTVSGFSLTNYGVHWVRQSPGKGLEWLGV IWSGGNTDYNTPFTSRLSINKDNSKSQVFFKMNSLQSNDTAIYYCARALT YYDYEFAYWGQGTLVTVSAASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKRVEPKSPKSCDKTHTCPPCPAPELLGGPSVFLFPP KPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTP PVLDSDGSFFLYSKLTVDKSRWQQGNVFSCSVMHEALHNHYTQKSLSLSP GK |
| 5 | EGF-ABXL (Anti-EGFR Light Chain 3)<br>DIQMTQSPSSLSASVGDRVTITCQASQDISNYLNWYQQKPGKAPKLLIYD ASNLETGVPSRFSGSGSGTDFTFTISSLQPEDIATYFCQHFDHLPLAFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |
| 6 | EGF-ABXH (Anti-EGFR Heavy Chain 3)<br>QLQESGPGLVKPSETLSLTCTVSGGSVSSGDYYWTWIRQSPGKGLEWIGH IYYSGNTNYNPSLKSRLTISIDTSKTQFSLKLSSVTAADTAIYYCVRDRV TGAFDIWGQGTMVTVSSASTKGPSVFPLAPCSRSTSESTAALGCLVKDYF PEPVTVSWNSGALTSGVHTFPAVLQSSGLYSLSSVVTVPSSNFGTQTYTC NVDHKPSNTKVDERKCCVECPAGPSVFLFPPKPKDTLMISRTPEVTCVVV DVSHEDPEVQFNWYVDGVEVHNAKTKPREEQFNSTFRVVSVLTVVHQDWL NGKEYKCKVSNKGLPAPIEKTISKTKGQPREPQVYTLPPSREEMTKNQVS LTCLVKGFYPSDIAVEWESNGQPENNYKTTPPMLDSDGSFFLYSKLTVDK SRWQQGNVFSCSVMHEALHNHYTQKSLSLSPGK |
| 7 | Nimotuzumab Light Chain<br>DIQMTQSPSSLSASVGDRVTITCRSSQNIVHSNGNTYLDWYQQTPGKAPK LLIYKVSNRFSGVPSRFSGSGSGTDFTFTISSLQPEDIATYYCFQYSHVP WTFGQGTKLQITREVAAPSVFIFPPSDEQLKSGTASVVCLLNNFYPREAK VQWKVDNALQSGNSQESVTEQDSKDSTYSLSSTLTLSKADYEKHKVYACE VTHQGLSSPVTKSFNRGEC |
| 8 | Nimotuzumab Heavy Chain<br>QVQLQQSGAEVKKPGSSVKVSCKASGYTFTNYYTYWVRQAPGQGLEWIGG INPTSGGSNFNEKFKTRVTITADESSTTAYMELSSLRSEDTAFYFCTRQG LWFDSDGRGFDFWGQGTTVTVSSASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVP |
| 9 | Matuzumab Light Chain<br>QVDIQMTQSPSSLSASVGDRVTITCSASSSVTYMYWYQQKPGKAPKLLIY DTSNLASGVPSRFSGSGSGTDYTFTISSLQPEDIATYYCQQWSSHIFTFG QGTKVEIKRTVAAPSVFIFPPSDEQLKSGTASVVCLLNNFYPREAKVQWK VDNALQSGNSQESVTEQDSKDSTYSLSSTLTLSKADYEKHKVYACEVTHQ GLSSPVTKSFNRGE |
| 10 | Matuzumab Heavy Chain<br>QVQLVQSGAEVKKPGASVKVSCKASGYTFTSHWMHWVRQAPGQGLEWIGE FNPSNGRTNYNEKFKSKATMTVDTSTNTAYMELSSLRSEDTAVYYCASRD |

TABLE 1-continued

Amino acid sequences of exemplifying antigen binding units

| SEQ ID NO: | Amino acid sequence and name |
|---|---|
| | YDYDGRYFDYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKS |

Another example of the antigen binding unit is Cetuximab which is a chimeric (mouse/human) monoclonal antibody targeting epidermal growth factor receptor (EGFR). The light and heavy chain sequences of Cetuximab are provided as SEQ ID NO: 3 and 4, respectively, shown in Table 1. Another anti-EGFR antibody is Panitumumab which is a fully human monoclonal antibody. Still another anti-EGFR antibody is Nimotuzumab, and the light and heavy chain sequences of Nimotuzumab are provided as SEQ ID NO: 7 and 8; still another anti-EGFR antibody is Matuzumab, and the light and heavy chain sequences of Matuzumab are provided as SEQ ID NO: 9 and 10. EGFR is over expressed in many cancer tissues such as metastatic colorectal cancer and head and neck cancer.

Rituximab is a chimeric monoclonal antibody against the protein CD20, which is primarily found on the surface of B cells. Rituximab specifically binds to and destroys B cells, and is therefore used to treat diseases which are characterized by excessive numbers of B cells, overactive B cells, or dysfunctional B cells. This includes many lymphomas, leukemias, transplant rejection, and some autoimmune disorders. The light chain and heavy chain sequences of Rituximab are provided in Table 1 as SEQ ID NO: 13 and 14, respectively.

Similarly, the monoclonal antibody trastuzumab (marketed as Herceptin®) is a chimeric monoclonal antibody against the protein Her2, that interfering with the Her2/neu receptor. The light chain and heavy chain sequences of trastuzumab are provided in Table 1 as SEQ ID NO: 11 and 12, respectively. In some cancers, notably some breast cancers, Her2 is over-expressed, and causes breast cells to reproduce uncontrollably. Trastuzumab is used to treat certain breast cancers and gastric cancers.

Additional examples of antigen binding units and their sequences are provided in Table 1, without limitation.

Non-antibody molecules can also be used an antigen binding unit to target specific cell populations. For example, GM-CSF, which binds to myeloid cells, can be used as a cell-binding agent to target diseased cells from acute myelogenous leukemia. In addition, IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor (EGF) can be used to target squamous cancers such as lung and head and neck. Somatostatin can be used to target neuroblastomas and other tumor types. Cancers of the breast and testes can be successfully targeted with estrogen (or estrogen analogues) or androgen (or androgen analogues) respectively as cell-binding agents.

In some embodiments, the antibody is an equivalent of any one of the antibodies described herein. Equivalents of antibody include those having at least about 80% homology or identity or alternatively, at least about 85%, or alternatively at least about 90%, or alternatively at least about 95%, or alternatively 98% homology with nepenthesin, or alternatively a polypeptide or protein encoded by a polynucleotide that hybridizes under stringent conditions to the nucleotide sequence encoding nepenthesin or its complement, while maintaining the desired structure and exhibiting at least part of the antigen binding activity of the antibody.

In another aspect, provided is a D-L-Abu which is one or more of maytansinoid lined with Bat0206, wherein Bat0206 comprises an anti-EGFR light chain having an amino acid sequence of SEQ ID NO: 1 and an anti-EGFR heavy chain having an amino acid sequence of SEQ ID NO: 2, or an equivalent thereof.

In some embodiments, provided herein is a maytansinoid linker Bat0206 conjugate of Formula Id or IId:

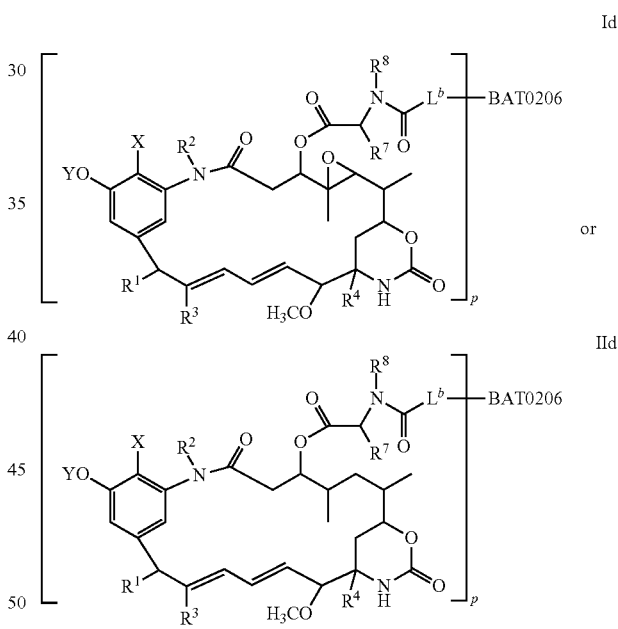

or a pharmaceutically acceptable salt or solvate thereof, wherein

X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH; and
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
p is selected from 1, 2, 3, 4, 5, 6, 7, 8, 9, and 10; and $L^b$ is selected from $C_1$-$C_{20}$ alkylene optionally substituted with $C_1$-$C_4$ alkyl, —$SO_3H$ or —$P(O)(OH)_2$, $C_3$-$C_8$ cycloalkylene optionally substituted with $C_1$-$C_4$ alkyl, and $C_1$-$C_{20}$ alkylene which is optionally substituted with $C_1$-$C_4$ alkyl —$SO_3H$ or —$P(O)(OH)_2$ and wherein one or more of the —$CH_2$— groups are independently replaced with $C_3$-$C_8$ cycloalkylene, —O—, —S—, —S—S—, —$NR^8$—, —$C(=O)NR^8$—, —$NR^8C(=O)$—, —$SO_2NR^8$—, or —$NR^8SO_2$, 3-8 membered heterocycloalkylene optionally substituted with one or more $C_1$-$C_4$ alkyl or oxo.

In some embodiments, $L^b$ is $C_1$-$C_{20}$ alkylene which is optionally substituted with $C_1$-$C_4$ alkyl, —$SO_3H$ or —$P(O)(OH)_2$ and wherein one or more of the —$CH_2$— groups are independently replaced with —S—, —S—S—, —$C(=O)NR^8$—, —$NR^8C(=O)$—,

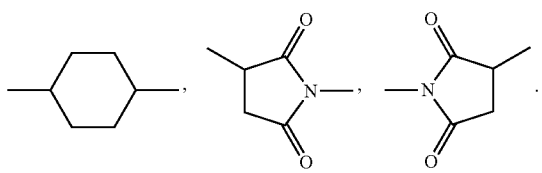

In some embodiments, the compound of Formula Id is selected from:

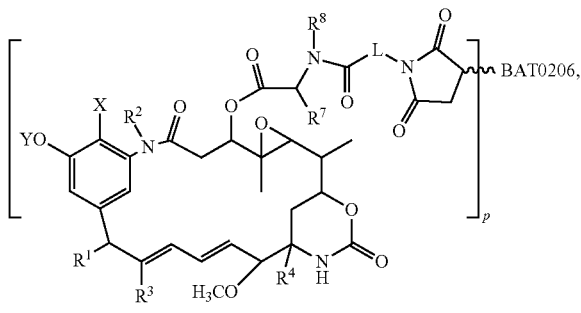
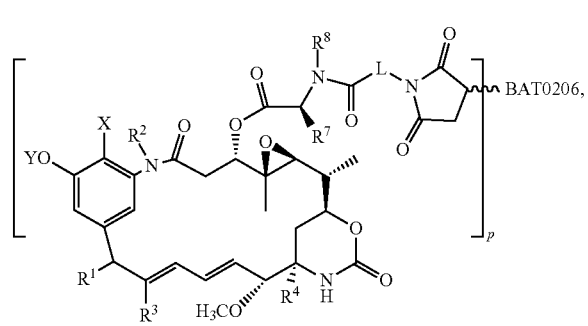

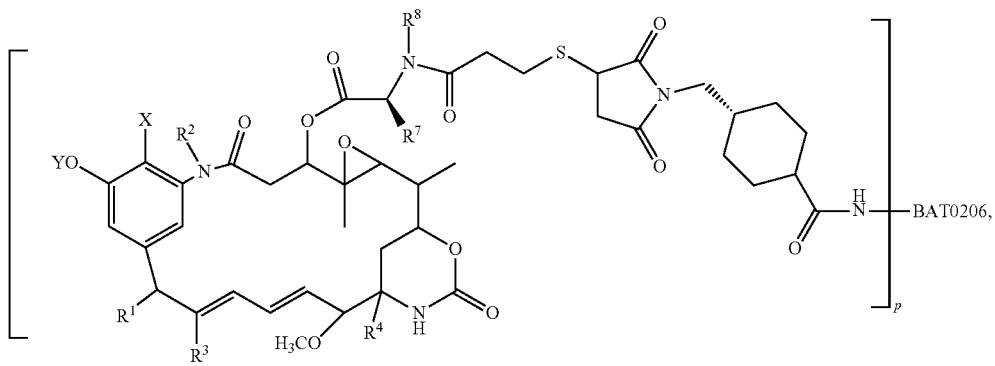

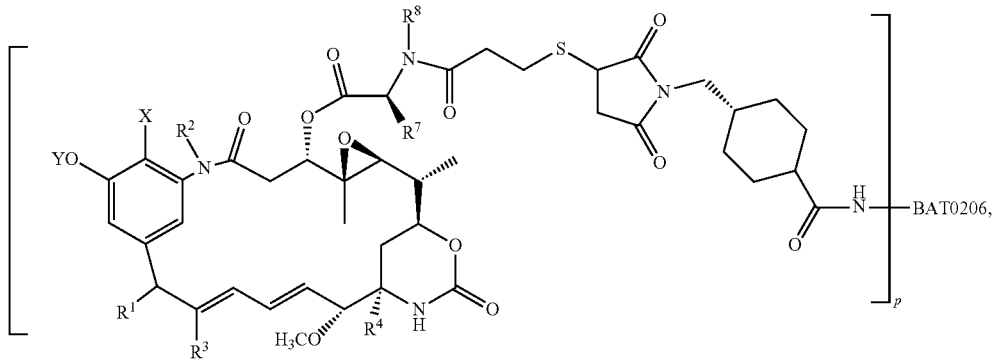

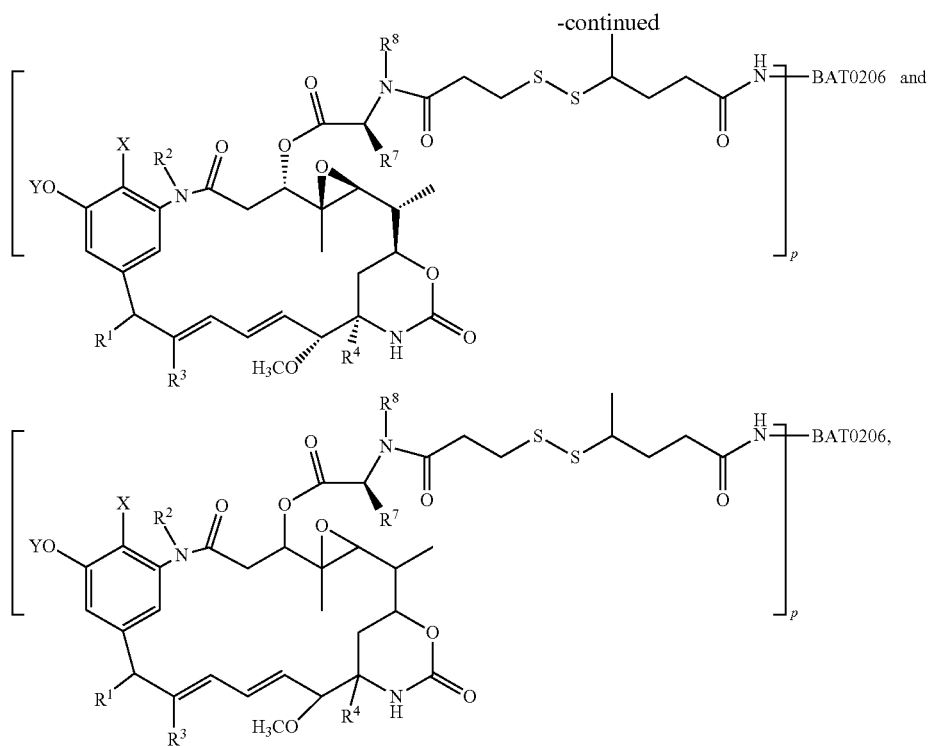
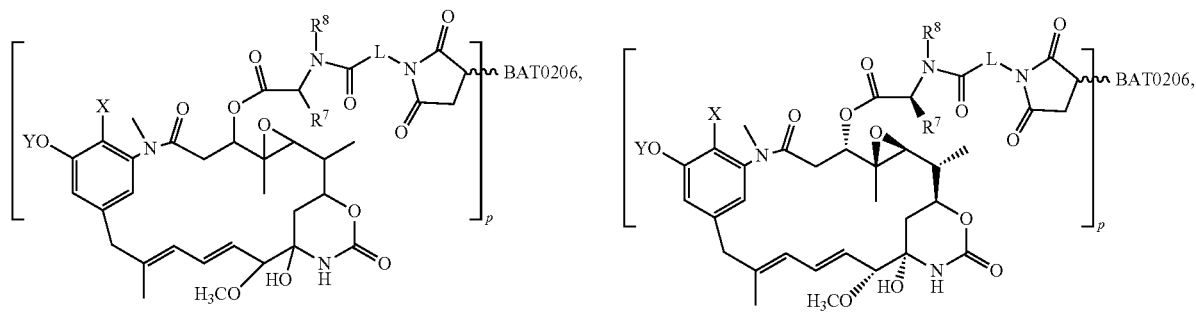
or a pharmaceutically acceptable salt or solvate thereof,
In some embodiments, the compound of Formula Id is selected from:
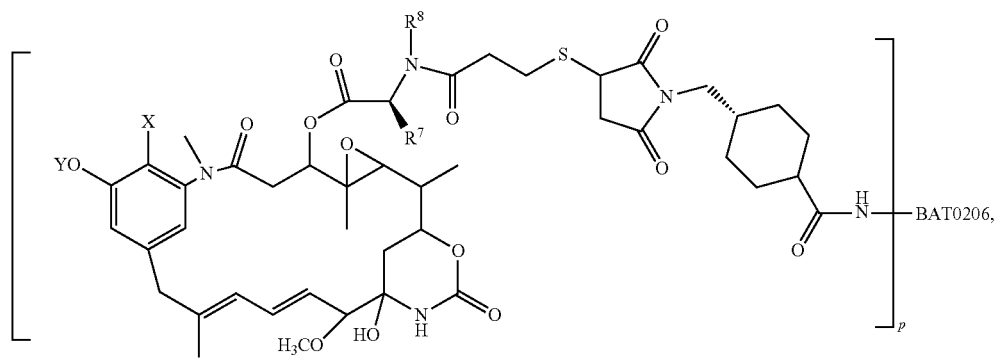

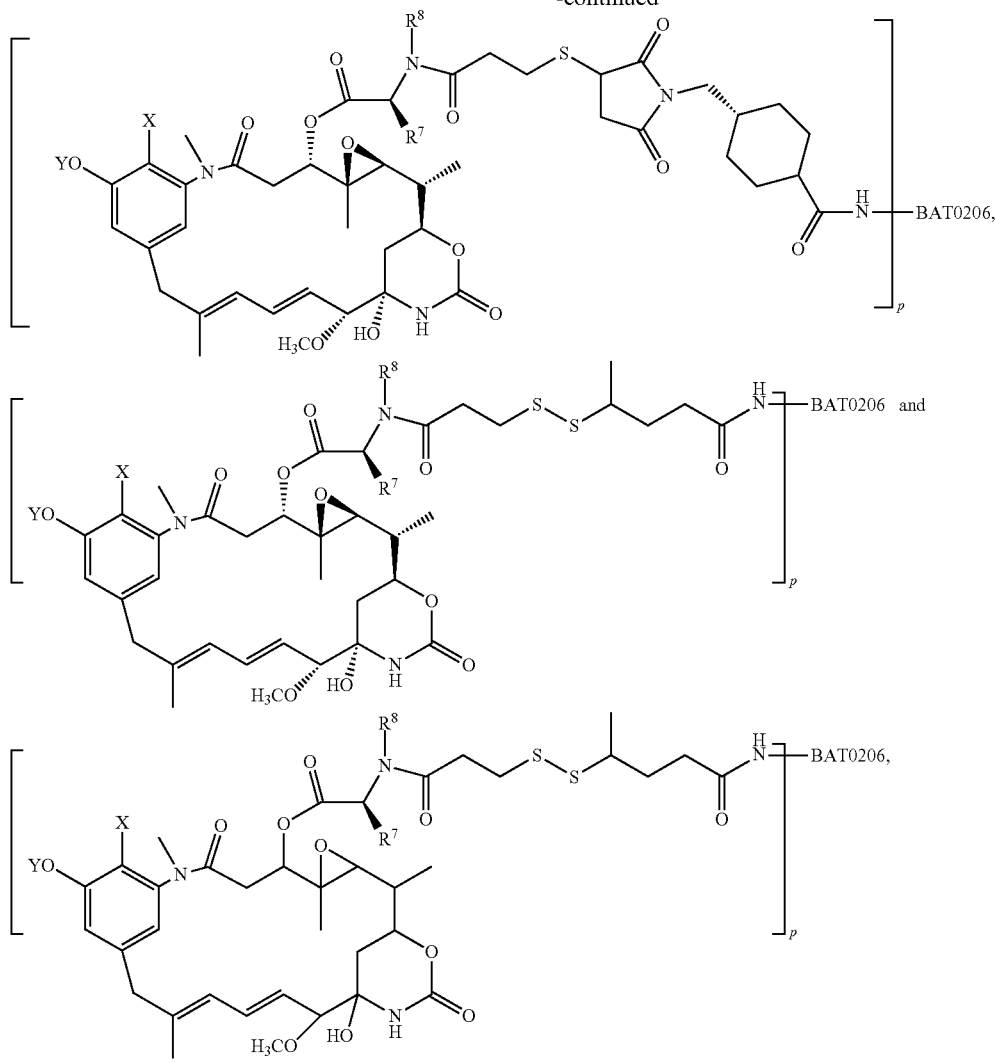
or a pharmaceutically acceptable salt or solvate thereof, wherein
X is H or Cl;
Y is H or methyl;
$R^7$ is hydrogen, $C_1$-$C_6$ alkyl or an amino acid side chain;
$R^8$ is hydrogen or $C_1$-$C_6$ alkyl;
p is selected from 1, 2, 3, 4, 5, 6, 7, 8, 9, and 10.
In some embodiments, the compound of Formula Id is selected from:
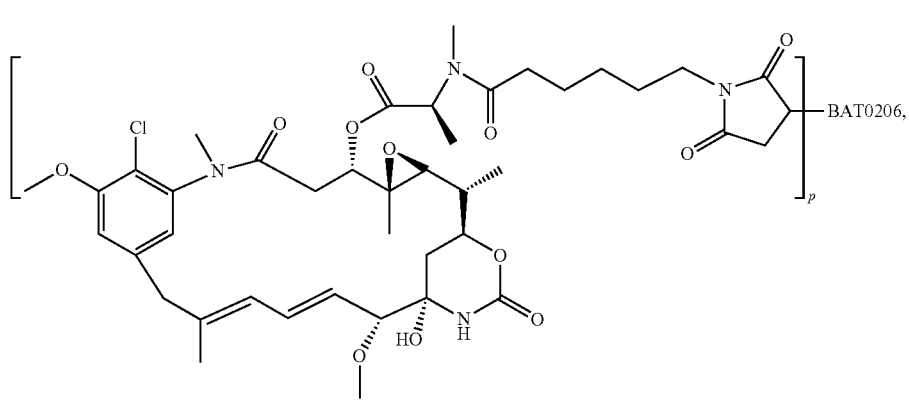
(Batansine-0206)

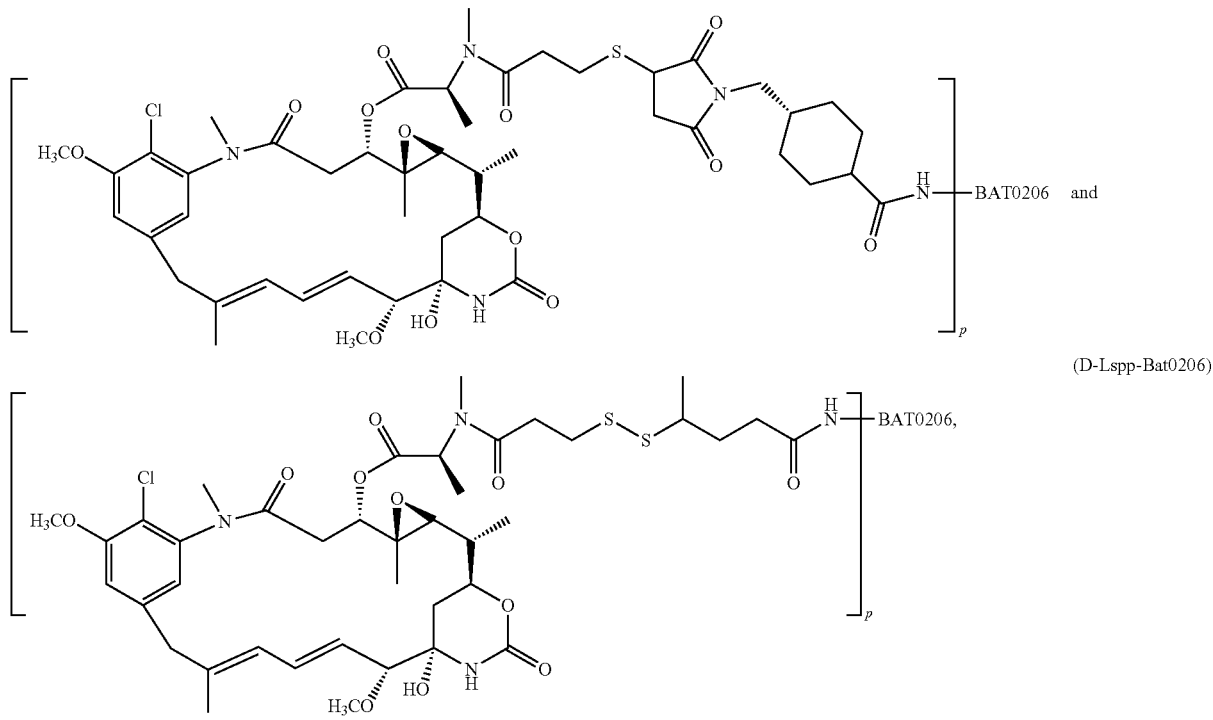

(D-Lmcc-Bat0206)

(D-Lspp-Bat0206)

or a pharmaceutically acceptable salt or solvate thereof.

Conjugation of a Drug to an Antigen Binding Unit

As discussed, a drug (e.g., a maytansinoid drug derivative) can be conjugated to an antigen binding unit through a linker. In one embodiment, the antigen binding unit can be modified with appropriate bifunctional modifying agent. In some embodiments, a group comprising a thiol (SH) group (also referred to as thio-comprising group) can be introduced to the side-chain of an amino acid residue, such as the side-chain of a lysine, on the antigen binding unit. For example, the amino group of a lysine residue on the antigen binding unit can be converted to a thiol-comprising group by reaction with 2-iminothiolane (Traut's Reagent), or with N-succinimidyl 3-(2-pyridyldithio)propanoate (SPDP), N-succinimidyl 4-(2-pyridyldithio)butanoate (SPDB), etc and followed by reduction with a reducing reagent, such as 2-mercaptoethanol, dithiothreitol (DTT) or tris(2-carboxyethyl)phosphine (TCEP).

Non-limiting examples of thiol-comprising group that can replace the side-chain amino group of a lysine residue include —NHC(=NH)(CH$_2$)$_n$SH and —NHC(O)(CH$_2$)$_n$SH, wherein n is 1, 2, 3, 4, 5 or 6. When a thiol-comprising group is introduced to an amino acid residue, the amino acid residue is referred to as thiolated amino acid. For example, when the side-chain amino group of a lysine residue is converted to a thio-comprising group, the lysine residue is referred to as thiolated lysine. The number of free thiol (SH) group introduced in an antigen binding unit may vary, such as between 1 and about 20, or 5 to 15, and or 5 to 12. The linkers or drug-linkers can form bonds with the free thiol (SH) group of a thiolated lysine residue on the antigen binding unit. In some embodiments, the number of linkers or drug-linkers that form bonds with thiolated lysine residues in the antigen binding unit is between 1 and about 10. In some embodiments, the number of such formed bonds is at least 1, or alternatively at least 2, or 3, or 4, or 5. In some embodiments, the number of such formed bonds is no more than 10, or alternatively no more than 9, or 8, or 7, or 6, or 5, or 4. In some embodiments, each antigen binding unit, on average, is conjugated with 3-5 drug molecules.

In another embodiment, a drug-linker can be conjugated to an antigen binding unit by binding to the thiol group of a cysteine residue. Each antigen binding unit typically contains multiple cysteines, but many, if not all, of them form disulfite bonds between each other, and thus are not available for such conjugation. In some embodiments, therefore, one or more of the disufite bonds of the antigen binding unit can be broken to form free thiol (SH) groups by reaction with a reducing reagent, such as 2-mercaptoethanol, dithiothreitol (DTT) or tris(2-carboxyethyl)phosphine (TCEP), for instance. The reaction can be monitored and/or controlled so that a sufficient number of disulfite bonds are broken to allow conjugation while maintaining a sufficient number of disulfide bonds to keep the structure stability of the antigen binding unit.

In some embodiments, the number of bonds formed between the drug-linker and cysteine residue on the antigen binding unit is from 1 to 10. In one embodiment, the number of such bonds is at least 1, or alternatively at least 2, or 3, or 4, or 5. In some embodiments, the number of such formed bonds is no more than 10, or alternatively no more than 9, or 8, or 7, or 6, or 5, or 4. In one embodiment, each antigen binding unit, on average, is conjugated with 3-5 drug molecules through cysteines.

In some embodiments, drug molecules are conjugated to the antigen binding unit through a mixture of lysine and cysteine residues.

An antigen binding unit can be modified, by way of, e.g., site-specific mutagenesis, to introduce additional thiolated lysine or cysteine residues to allow suitable conjugation. Amino acid modification methods are well known in the art. Modified antigen binding units can then be experimentally examined for their stability and antigen binding capability. In one embodiment, at least one thiolated lysine or cysteine residue is introduced by such modification. In another embodiment, at least two thiolated lysine or cysteine residues are introduced by such modification.

Drug Load

The drug load on an antigen binding unit may vary depending on many factors, such as the potency of the drug, the size, stability of the antigen binding unit, conjugatable groups available on the antigen binding unit, etc. In some embodiments, 1 to 10 maytansinoid drug molecules are conjugated with 1 antigen binding unit molecule. In some embodiments, an average of 3 to 5 maytansinoid drug molecules are conjugated with 1 antigen binding unit molecule. In some embodiments, an average of 3.5 maytansinoid drug molecules are conjugated with 1 antigen binding unit molecule.

Preparation of Drug Linker Antigen Binding Unit Conjugates

In another aspect, provided are methods of preparing a maytansinoid drug linker antigen binding unit conjugate compound comprising contacting a compound of any one of Formula I, I-1, II, II-1, III, III-1, IV, IV-1 and V with an antigen binding unit. In some embodiments, the compound of any one of Formula I, I-1, II, II-1, III, III-1, IV, IV-1 and V and an antigen binding unit are dissolved in an aqueous solution. In some embodiments, the solution comprises a buffer, such as a phosphate buffer.

Metabolites of Drug Linker Antigen Binding Unit Conjugates

While not wishing to be bound to any theories, it is contemplated that upon endocytosis, compounds of any one of Formula Ia-Va is degraded by intracellular proteins to degradation products comprising the maytansinoid moiety which are cytotoxic.

In another aspect, disclosed herein is a compound of Formula Ib or Ib-1:

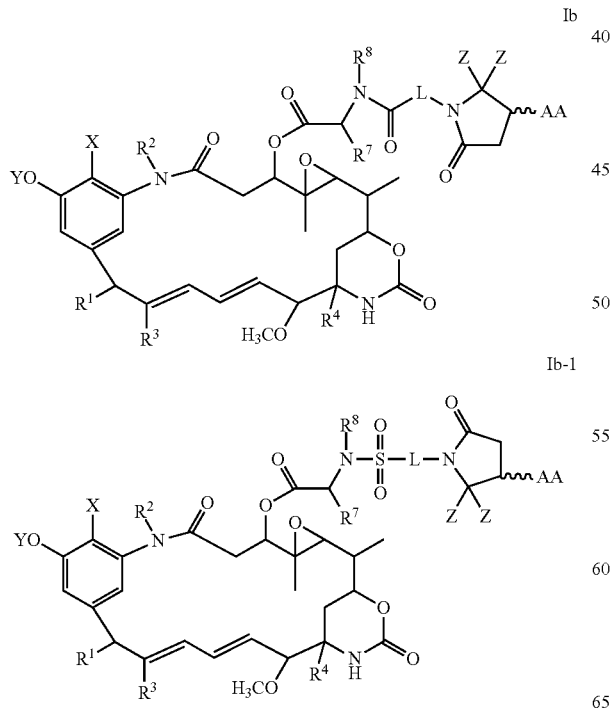

or a salt thereof, wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —$CH_2OH$, or —$CH_2C$(=O)$R^6$;

$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_{1-6}$ alkyl;

each Z is independently hydrogen or $C_1$-$C_4$ alkyl, or the two Z with the carbon atom to which they are attached form a C=O;

L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8C$(=O)—, —$SO_2NR^8$—, or —$NR^8SO_2$—; Preferably L is —$(CH_2)_m$—, wherein m is selected from an integer of 1 to 20, preferably 1 to 10, more preferably 5 to 10;

substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and AA is an amino acid, such as a cysteine or a thiolated amino acid, such as a thiolated lysine.

In some embodiments, the compound is:

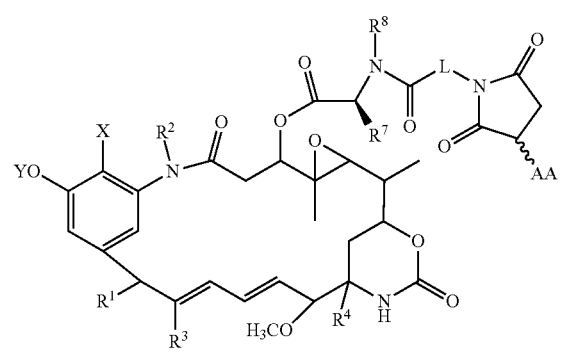

-continued

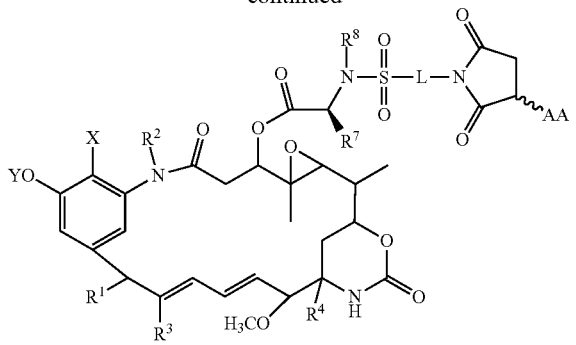

or a salt thereof,

In some embodiments, provided herein is a compound of Formula IIb or IIb-1:

IIb

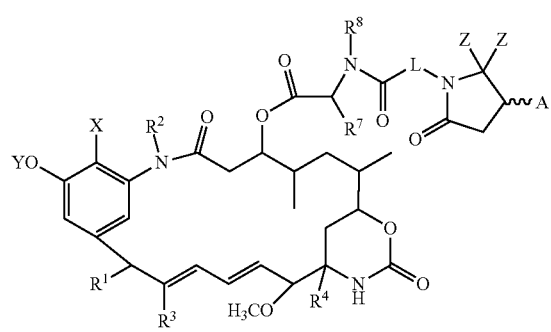

IIb-1

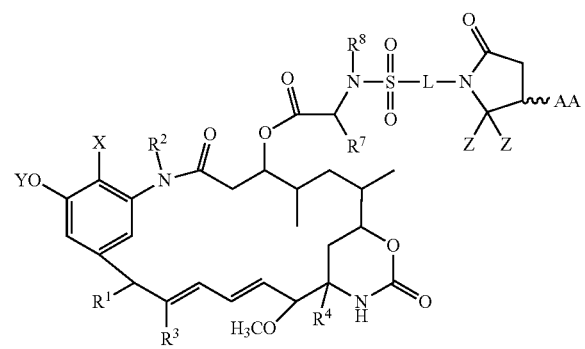

or a salt thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
each Z is independently hydrogen or $C_1$-$C_4$ alkyl, or the two Z with the carbon atom to which they are attached form a C=O;

L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —NR$^8$—, —C(O)—, —C(=O)NR$^8$—, —NR$^8$C(=O)—, —SO$_2$NR$^8$—, or —NR$^8$SO$_2$—; preferably L is —(CH$_2$)$_m$—, wherein m is selected from an integer of 1 to 20, preferably 1 to 10, more preferably 5 to 10;

substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and AA is an amino acid, such as a cysteine or a thiolated amino acid, such as a thiolated lysine.

In some embodiments, X is hydrogen. In some embodiments, X is chloro. In some embodiments, Y is hydrogen. In some embodiments, $R^1$ is hydrogen. In some embodiments, $R^2$ is methyl. In some embodiments, $R^3$ is methyl. In some embodiments, $R^4$ is —OH. In some embodiments, $R^7$ is an amino acid side chain. In some embodiments, $R^7$ is methyl. In some embodiments, $R^8$ is methyl.

In some embodiments, L is unsubstituted $C_1$-$C_{20}$ alkylene. In some embodiments, L is substituted $C_1$-$C_{20}$ alkylene. In some embodiments, L is unsubstituted $C_1$-$C_{10}$ alkylene. In some embodiments, L is substituted $C_1$-$C_{10}$ alkylene. In some embodiments, L is —(CH$_2$)$_5$—. In some embodiments, L is unsubstituted $C_1$-$C_{20}$ alkylene wherein one or two of the —CH$_2$— groups are independently replaced with $C_3$-$C_8$ cycloalkylene, —O—, —S—, —NR$^8$—, —C(=O)NR$^8$—, —NR$^8$C(=O)—, —SO$_2$NR$^8$—, or —NR$^8$SO$_2$—. In some embodiments, L is substituted $C_1$-$C_{20}$ alkylene wherein one or two of the —CH$_2$— group is independently replaced with $C_3$-$C_8$ cycloalkylene, —O—, —S—, —NR$^8$—, —C(=O)NR$^8$—, —NR$^8$C(=O)—, —SO$_2$NR$^8$—, or —NR$^8$SO$_2$—. In some embodiments, when more than one —CH$_2$— groups are replaced, the —CH$_2$— groups are not adjacent to each other.

In some embodiments, provided is a compound of the formula:

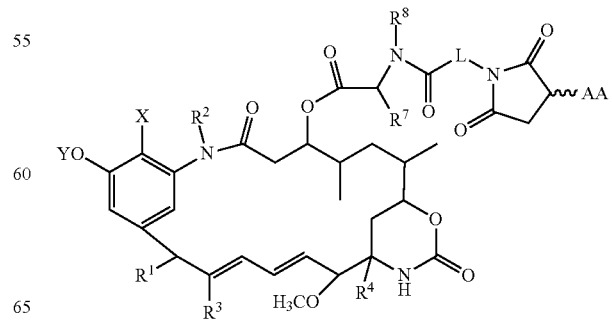

-continued

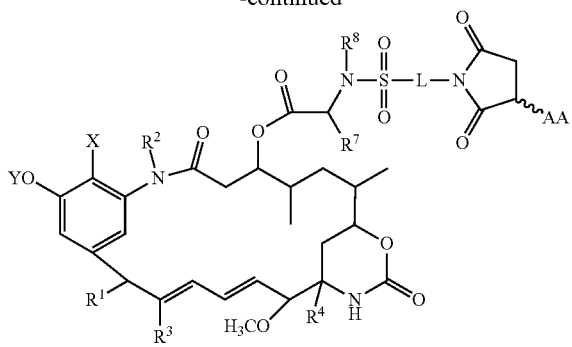

In some embodiments, provided is a compound of Formula IIIb or IIIb-1:

IIIb

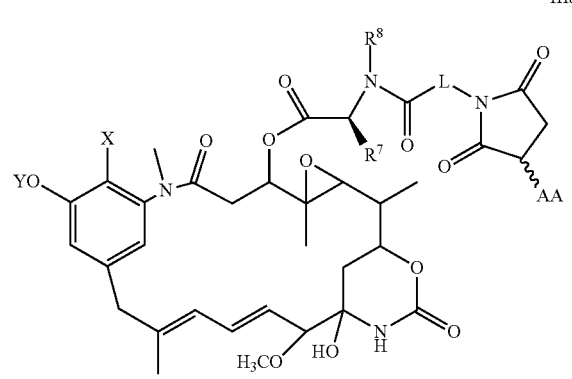

IIIb-1

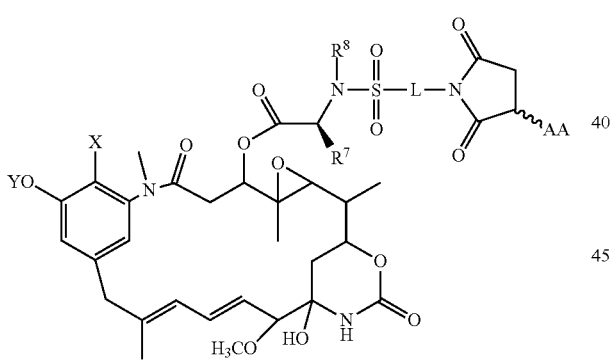

or a salt thereof,
wherein
X is H or Cl;
Y is H or methyl;
$R^7$ is hydrogen, $C_1$-$C_6$ alkyl or an amino acid side chain;
$R^8$ is hydrogen or $C_1$-$C_6$ alkyl;
L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8$C(=O)—, —$SO_2NR^8$—, or —$NR^8SO_2$—; preferably L is —$(CH_2)_m$—, wherein m is selected from an integer of 1 to 20, preferably 1 to 10, more preferably 5 to 10;
substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and AA is an amino acid, such as a cysteine or a thiolated amino acid, such as a thiolated lysine.

In some embodiments, the compound is of Formula IVb or IVb-1:

IVb

IVb-1 or a salt thereof,
wherein
X is H or Cl;
Y is H or methyl;
$R^7$ is hydrogen, $C_1$-$C_6$ alkyl or an amino acid side chain;
$R^8$ is hydrogen or $C_1$-$C_6$ alkyl;
m is an integer of 1 to 20, preferably 1 to 10, more preferably 5 to 10; and
AA is an amino acid, such as a cysteine or a thiolated amino acid, such as a thiolated lysine.

In some embodiments, the compound is of Formula Vb:
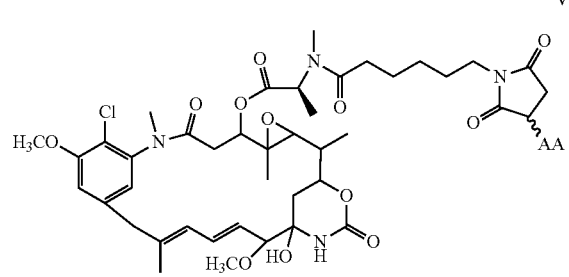
or a salt thereof.
In some embodiments, AA is, but not limited to:
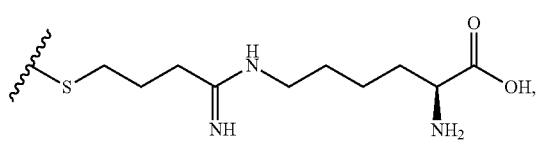
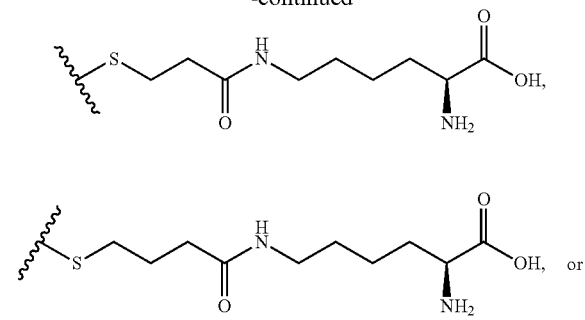
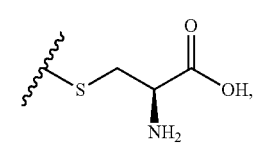
wherein ~~~ represents point of connection to the rest of the molecule.
In some embodiments, the compound of Formula Ib is selected from:
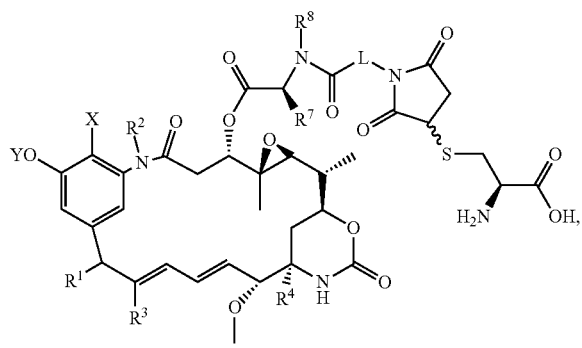
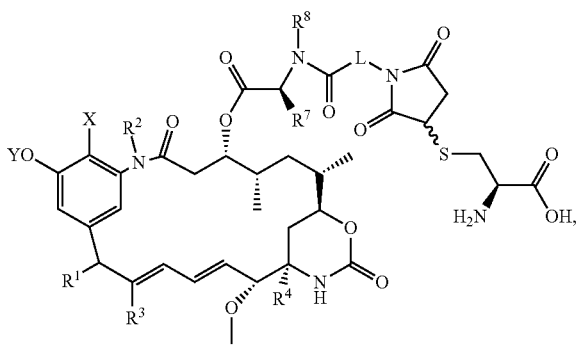
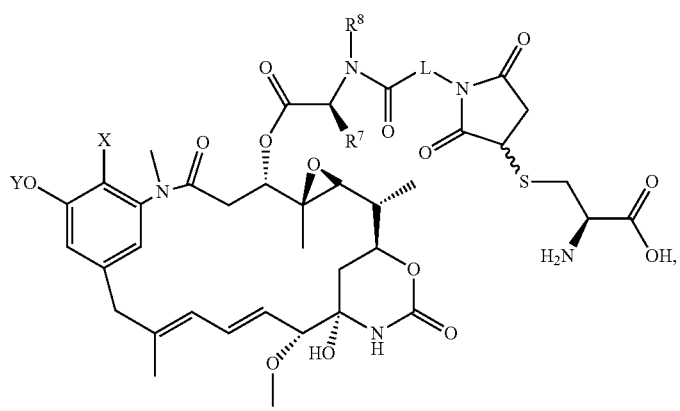

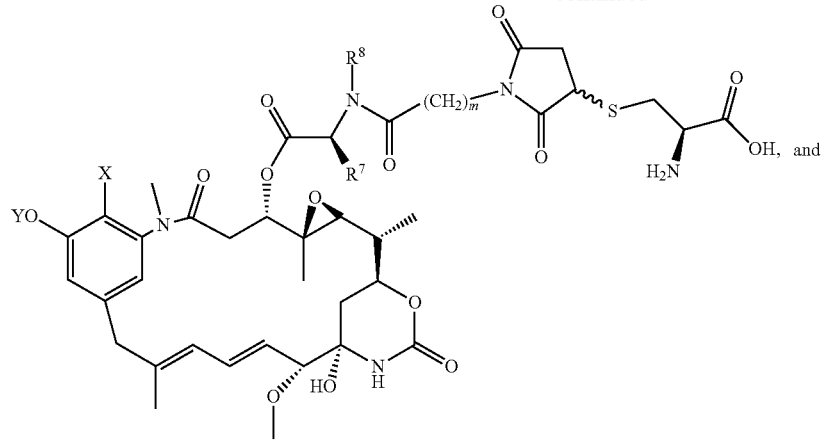
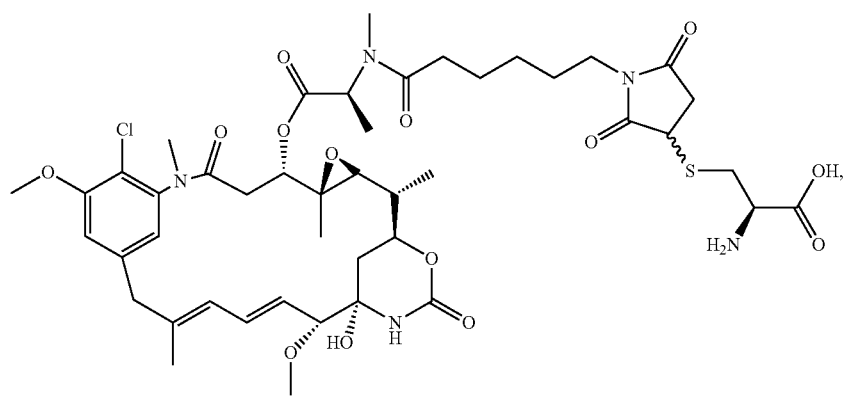
or a salt thereof.
While not wishing to be bound to any theories, it is contemplated that upon endocytosis, compounds of any one of Formula Ia-Va, formula Va-XIIa is degraded by intracellular proteins to degradation products comprising the maytansinoid moiety which are cytotoxic.
In another aspect, disclosed herein is a compound of Formula Vc:
Vc
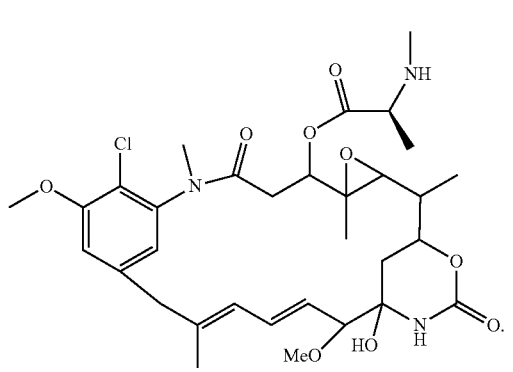

In another aspect, disclosed herein are compounds degraded by intracellular proteins to degradation products comprising the maytansinoid moiety which are cytotoxic, and these compounds include but not limited to:
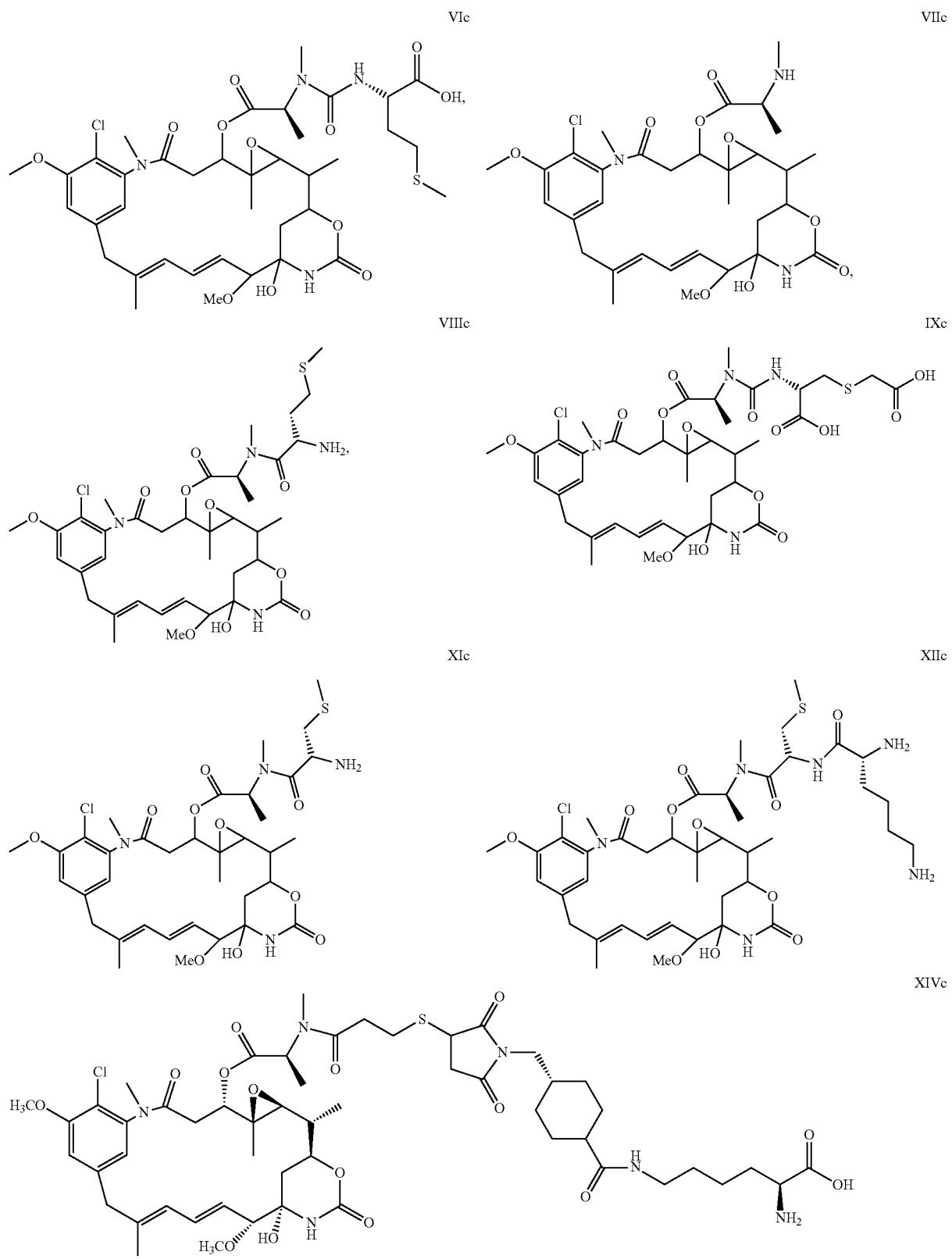

Methods of Treatment

In another aspect, provided herein is a method of treating a proliferative, inflammatory or immunologic disease or condition in a patient in need thereof comprising administering an effective amount of one or more compounds as described herein, for example, a compound of any one of Formula Ia-Va, Id and formula Va-XIVc.

The compounds can be formulated as pharmaceutical compositions and administered to the patient in a variety of forms adapted to the chosen route of administration, i.e., orally or parenterally, by intravenous, intramuscular, topical or subcutaneous routes. The amount of the compounds will vary depend on the nature of the drug, linker, drug load, degree of cell surface triggered the internalization, trafficking, and release of the drug, the disease being treated, the conditions of the patient, such as age, gender, weight, etc. and can be determined by methods known to the art, for example, see U.S. Pat. No. 4,938,949, and will be ultimately at the discretion of the attendant physician or clinician.

In general, a suitable dose will be in the range of from about 0.1 to about 200 mg/kg, e.g., from about 0.5 to about 50 mg/kg of body weight IV infusion over 30-90 min every 1-4 week for 52 weeks, about 1.0 to about 25 mg/kg of body weight IV infusion over 30-90 min every 1-4 week for 52 weeks, about 1.5 to about 15 mg/kg body weight IV infusion over 30-90 min every 1-4 week for 52 weeks, or in the range of about 1 to 10 mg/kg body weight IV infusion over 30-90 min every 1-4 week. In some embodiments, the dose is from about 1.0 mg to about 100 mg/day, e.g., from about 2 mg to about 5 g per day, about 10 mg to about 1 g per day, about 20 to about 500 mg per day, or in the range of about 50 to 100 mg per day. The compounds can be administered daily, weekly, monthly, such as once a day, every 1-3 weeks, or month. Alternatively, the compounds can be administered in cycles, such as administered daily for a number of days, for example, 5 days to 21 days, with a period, such as one day to seven days, wherein no drug is being administered.

In some embodiments, the compound is administered at an initial dose of 1-4 mg/kg over 30-90 minute IV infusion, followed by 1-2 mg/kg over 30 minute IV infusion weekly or every 1-4 weeks for 52 weeks. In some embodiments, the compound is administered at an initial dose of 2-10 mg/kg over 30-90 minutes IV infusion, followed by 1-5 mg/kg over 30-90 minutes IV infusion every 1-4 weeks for 52 weeks.

In some embodiments, the compounds are administered in conjunction with another therapy. For example, the compounds can be co-administered with another therapy for treating cancer, for example, radiation therapy or another anticancer agent known in the art.

In another aspect, provided herein is a method of treating a proliferative, inflammatory or immunologic disease or condition in a patient in need thereof comprising administering an effective amount of a compound of Formula Ib, wherein the compound of Formula Ib is generated as a result of a metabolic chemical reaction following administration of a compound of Formula Ia, or a pharmaceutically acceptable salt thereof, to the individual. Metabolic chemical reaction refers to a reaction occurring inside the body, for example, cells, of the subject, in which a chemical compound is converted to another chemical compound. The conversion can be by metabolic and/or chemical processes and can occur in one step or through a series of two or more steps. Metabolic chemical reactions include reactions of degrading a protein or peptide component of a maytansinoid linker antigen binding unit conjugate, such as an antibody or antibody fragment, by proteins inside a cell.

In some embodiments, provided herein is a method of treating a proliferative, inflammatory or immunologic disease or condition in a patient in need thereof comprising administering an effective amount of a compound of Formula IIb, wherein the compound of Formula IIb is generated as a result of a metabolic chemical reaction following administration of a compound of Formula IIa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula Mb, wherein the compound of Formula IIIb is generated as a result of a metabolic chemical reaction following administration of a compound of Formula IIIa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula VIb, wherein the compound of Formula VIb is generated as a result of a metabolic chemical reaction following administration of a compound of Formula VIa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula Vb, wherein the compound of Formula Vb is generated as a result of a metabolic chemical reaction following administration of a compound of Formula Va, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula Vc, wherein the compound of Formula Vc is generated as a result of a metabolic chemical reaction following administration of a compound of Formula Va, VIa, or VIIa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula VIIIc, wherein the compound of Formula VIIIc is generated as a result of a metabolic chemical reaction following administration of a compound of Formula VIIIa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula IXc, wherein the compound of Formula IXc is generated as a result of a metabolic chemical reaction following administration of a compound of Formula IXa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula Xc, wherein the compound of Formula Xc is generated as a result of a metabolic chemical reaction following administration of a compound of Formula Xa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula XIc, wherein the compound of Formula XIc is generated as a result of a metabolic chemical reaction following administration of a compound of Formula XIa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula XIIc, wherein the compound of Formula XIIc is generated as a result of a metabolic chemical reaction following administration of a compound of Formula XIIa, or a pharmaceutically acceptable salt thereof, to the patient.

In some embodiments, provided herein is a method of treating a proliferative, inflammatory or immunologic disease or condition in a patient in need thereof comprising administering an effective amount of a compound of Formula XIVc, wherein the compound of Formula XIVc is generated as a result of a metabolic chemical reaction following administration of a compound of Formula XIVa, or a pharmaceutically acceptable salt thereof, to the patient.

The diseases being treated can be determined by the antigen binding unit of the conjugate. In some embodiments, the disease a proliferative disease, such as a cancer, including melanoma, breast cancer, bladder cancer, lung cancer, thyroid cancer, prostate cancer, ovarian cancer, mast cell leukemia, germ cell tumors, small-cell lung carcinoma, gastrointestinal stromal tumors, acute myelogenous leukemia (AML), B-chronic lymphatic leukemia (B-CLL), and non-Hodgkin lymphoma (NHL), neuroblastoma, or pancreatic cancer. In some embodiments, the disease an inflammatory disease, or an immunologic disease, such as graft rejections, and autoimmune diseases, such as type 1 diabetes, rheumatoid arthritis, systemic lupus erythematosus, and inflammatory bowel disease.

Pharmaceutical Compositions

In a further aspect, provided are pharmaceutical compositions comprising one or more compounds as described herein, for example, a compound of any one of Formula Ia-Va, and one or more pharmaceutically acceptable carriers. Such compositions should contain at least 0.1% of active compound. The percentage of the compositions may vary and may be between about 2 to about 90% of the weight of a given unit dosage form. The amount of active compound in such therapeutically useful compositions is such that an effective dosage level will be obtained.

Examples of compositions for oral administration include, but are not limited to, ingestible tablets, buccal tablets, troches, capsules, elixirs, suspensions, syrups, solutions, wafers, and the like. Compositions suitable for injection or infusion can include sterile aqueous solutions or dispersions in a pharmaceutically acceptable liquid carrier or vehicle, or sterile powders comprising the active ingredient which are adapted for the extemporaneous preparation of sterile injectable or infusible solutions or dispersions, optionally encapsulated in liposomes. Other forms of pharmaceutical compositions include topical formulations, such as gel, ointments, creams, lotions or transdermal patches, etc.

The pharmaceutical compositions include using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

In a further aspect, provided are methods of producing a pharmaceutical composition comprising admixing a compound as described herein, for example, a compound of any one of Formula Ia-Va and Id, and a pharmaceutically acceptable carrier. Methods of admixing an active ingredient with a pharmaceutically acceptable carrier are generally known in the art, for example, uniformly mixing the active compound (s) with liquids or finely divided solid carriers, or both, in the required proportions, and then, if necessary, forming the resulting mixture into a desired shape.

In some embodiments, a compound of any one of Formula Ia-Va and Id is formulated as an injectable, for example, at a concentration of 2-50 mg/mL in an aqueous solution comprising 4-10 mg/mL sodium chloride and/or 5-12 mg/mL sodium acetate, or alternatively at a concentration of 2-50 mg/mL in an aqueous solution comprising 5-10 mg/mL sodium chloride, 1-5 mg/mL sodium phosphate dibasic heptahydrate, 0.1-0.5 mg/mL sodium phosphate monobasic monohydrate.

Other examples of formulations of a compound of any one of Formula Ia-Va and Id include an injectable formulation having a concentration of 2-100 mg/mL of the compound in an aqueous solution comprising 0.5-1.0% sodium chloride, 0.05-0.10% monobasic sodium phosphate dihydrate, 1.0-2.0% dibasic sodium phosphate dihydrate, 0.01-0.05% sodium citrate, 0.10-0.20% citric acid monohydrate, 1.0-2.0% mannitol, 0.1%-0.2 polysorbate 80, and Water for Injection, USP. Sodium hydroxide added as necessary to adjust pH.

Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Coupling reagents include carbodiimide, amininum and phosphonium based reagents. Carbodiimide type reagents include dicyclohexylcarbodiimide (DCC), diisopropylcarbodiimide (DIC), and 1-ethyl-3-(3-dimethylaminopropyl)-dicarbodiimide (EDC), etc. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (TCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include 7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (PyBOP). Amide formation step may be conducted in a polar solvent such as dimethylformamide (DMF) and may also include an organic base such as diisopropylethylamine (DIEA) or dimethylaminopyridine (DMAP).

The following examples are provided to illustrate certain aspects of the present invention and to aid those of skill in the art in practicing the invention. These examples are in no way to be considered to limit the scope of the invention.

EXAMPLES

The examples below as well as throughout the application, the following abbreviations have the following meanings. If not defined, the terms have their generally accepted meanings.

ACN=acetonitrile
Ala=alanine
aq.=aqueous
brs=broad singlet
calc.=calculated
d=doublet
DCM=dichloromethane
dd=double doublet
DIEA=N,N-diisopropylethylamine
DMA=N,N-dimethylacetamide
DMAP=dimethylaminopyridine
DMF=dimethylformamide
DMSO=dimethylsulfoxide
DTT=dithiothreitol
EDTA=ethylenediaminetetraacetate or salt
Et=ethyl
EtOAc=ethyl acetate
g=gram
h=hour
HCl=hydrochloric acid
HPLC=high-pressure liquid chromatography
Hz=hertz
J=coupling constant
LC-MS=liquid chromatography mass spectroscopy
m=multiplet
MDC=maytansinol
Me=methyl
MeOH=methanol
MHz=megahertz
min=minute
mL=milliliter
mm=millimeter
m.p.=melting point
OTf=triflate (trifluoromethanesulfonate)
N=normal
r.t.=room temperature
PBS=phosphate buffered saline
Rt=retention time
s=singlet
t=triplet
TLC=thin layer chromatography
vol=volume
μL=microliter
μm=micrometer MATERIALS AND METHODS: NMR specetra were recorded on a Bruker AM 400 (400 MHz) spectrometer. Chemical shifts in CDCl$_3$ are reported in ppm relative to residual CHCl$_3$ as an internal standard. UV spectra were recorded on a Beckman DU-640 spectrophotometer. Mass spectra were acquired on a ThermoFinnigan LCQ DECA XP+ instrument using electrospray ionization. HPLC was performed using an Agilent HPLC 1100 system equipped with a diode array detector and a Kromasil reverse phase C-18 5 μm, 250×4.6 mm column, eluting with a gradient of acetonitrile:water (50-95% CH$_3$CN 0-10 min, 95% CH$_3$CN 10-15 min, flow rate=1.0 mL/min. Silica gel for flash column chromatography was from Branch of Qiangdao Haiyang Chemical Co., Ltd. Maytansinol was prepared from ansamitocin P-3 (which in turn was obtained from the fermentation of the microorganism *Actinosynnema pretiosum*) as previously described (Widdison, et al. (2006) J. Med. Chem. 49: 4392-4408). Dichloromethane was dried by distillation over calcium hydride. Dimethylformamide was dried by distillation over calcium hydride under reduced pressure. All other solvents used are reagent grade or HPLC grade.

Example 1

Esterification of Maytansinol with Fmoc-N-methyl-L-alanine (Fmoc-N-Me-D/L-Ala-MDC)

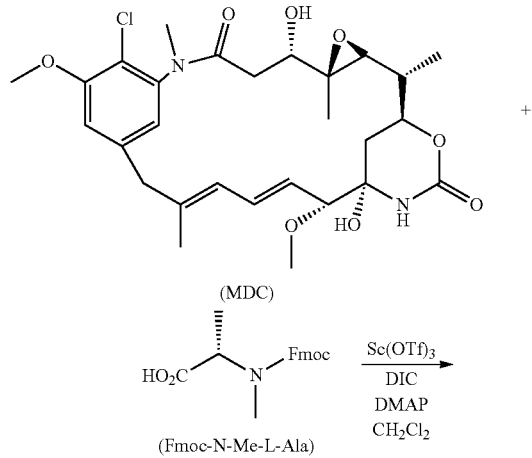

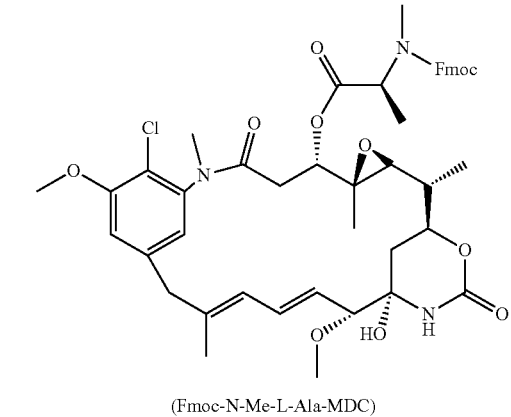

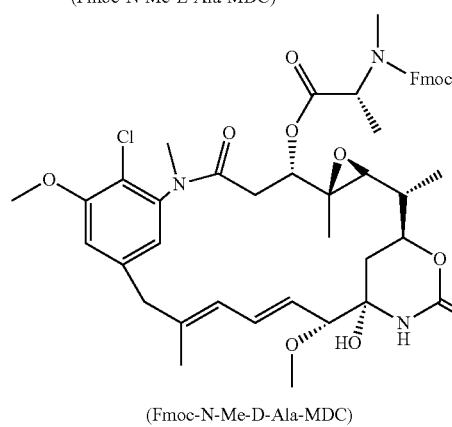

A mixture of maytansinol (0.600 g, 1.062 mmol), Fmoc-N-Me-L-Ala (6.911 g, 21.24 mmol), Sc(OTf)$_3$ (0.314 g, 0.637 mmol) and DMAP (0.389 g, 3.186 mmol) in CH$_2$Cl$_2$ (100 mL) was stirred for 0.5 h at −8° C. DIC (2.949 g, 23.37 mmol) was added dropwise, stirred for 0.5 h, warmed to r.t. slowly, filtered to recover the Lewis acid catalyst, the filtrate was quenched with diluted HCl and extracted with CH$_2$Cl$_2$.

The combined organic phase was washed with NaHCO$_3$ aq, brine, dried over anhydrous Na$_2$SO$_4$. The solvent was removed under reduced pressure. Chromatography (silica gel, CH$_2$Cl$_2$/MeOH 30:1) gave the desired product as a mixture of diastereomer Fmoc-N-Me-D/L-Ala-MDC: white solid (0.8385 g, 90.5%). Further column chromatography (silica gel, CH$_2$Cl$_2$/MeOH 100:1 to 20:1) gave two fractions as pure diastereomer. The higher Rf fraction was determined to be the D-aminoacyl ester diastereomer (Fmoc-N-Me-D-Ala-MDC), while the lower Rf fraction was the desired L-aminoacyl ester (Fmoc-N-Me-L-Ala-MDC). Fmoc-N-Me-L-Ala-MDC: white solid (0.4262 g, 46.0% yield), $^1$H NMR (400 MHz, CDCl$_3$): δ0.77 (3H, s), 1.22-1.32 (6H, m), 1.40-1.48 (1H, m), 1.63 (3H, s), 2.13 (1H, dd, J=14.4, 2.8 Hz), 2.53 (1H, dd, J=14.4, 10.8 Hz), 2.64 (3H, s), 2.88 (3H, s), 3.00 (1H, d, J=9.6 Hz), 3.07 (1H, d, J=12.4 Hz), 3.35 (3H, s), 3.48 (1H, d, J=8.8 Hz), 3.59 (1H, d, J=11.2 Hz), 3.97 (3H, s), 4.13-4.19 (1H, m), 4.15 (1H, s), 4.24 (1H, t, J=10.8 Hz), 4.72-4.77 (2H, m), 5.03 (1H, q, J=6.8 Hz), 5.65 (1H, dd, J=15.2, 9.2 Hz), 6.29 (1H, br), 6.41 (1H, dd, J=15.2, 11.2 Hz), 6.52 (1H, d, J=1.2 Hz), 6.70 (1H, d, J=10.8 Hz), 6.79 (1H, d, J=1.2 Hz), 7.33 (1H, t, J=7.6 Hz), 7.36 (1H, t, J=7.6 Hz), 7.39 (1H, d, J=7.6 Hz), 7.49 (1H, d, J=7.6 Hz), 7.70 (1H, d, J=7.6 Hz), 7.72 (1H, d, J=7.6 Hz). LC-MS (M+Na$^+$) calc.: 894.3. found: 894.3. Fmoc-N-Me-D-Ala-MDC: white solid (0.3993 g, 43.1% yield), $^1$H NMR (400 MHz, CDCl$_3$): δ0.84 (3H, s), 1.22-1.27 (3H, m), 1.40-1.48 (1H, m), 1.51 (3H, d, J=7.6 Hz), 1.67 (3H, s), 2.20 (1H, dd, J=14.4, 2.8 Hz), 2.63 (1H, dd, J=14.4, 12.4 Hz), 2.85 (1H, d, J=9.6 Hz), 2.96 (3H, s), 3.17 (3H, s), 3.20 (1H, s), 3.24 (3H, s), 3.40 (1H, d, J=9.2 Hz), 3.51 (1H, d, J=12.8 Hz), 3.99 (3H, s), 4.20-4.28 (2H, m), 4.38-4.43 (2H, m), 4.80-4.98 (2H, m), 5.80 (1H, dd, J=15.2, 11.2 Hz), 6.18 (1H, s), 6.25 (1H, d, J=10.8 Hz), 6.40 (1H, dd, J=15.2, 11.2 Hz), 6.79 (1H, d, J=1.6 Hz), 6.84 (1H, d, J=1.6 Hz), 7.32 (2H, t, J=7.6 Hz), 7.41 (2H, t, J=7.6 Hz), 7.61 (2H, d, J=7.6 Hz), 7.77 (2H, d, J=7.6 Hz). LC-MS (M+Na$^+$) calc.: 894.3. found: 894.3.

Example 2

Deprotection of Fmoc-N-Me-D/L-Ala-MDC (N-Me-D/L-Ala-MDC)

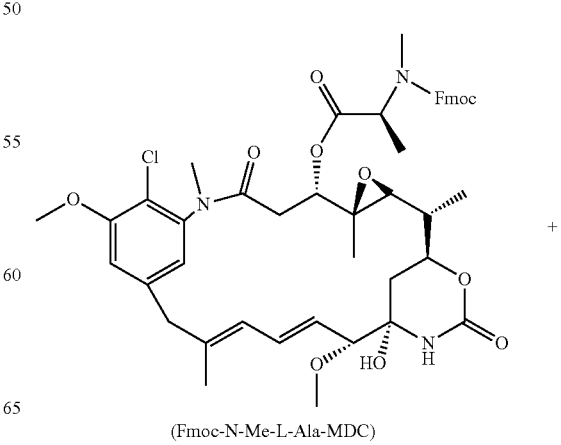

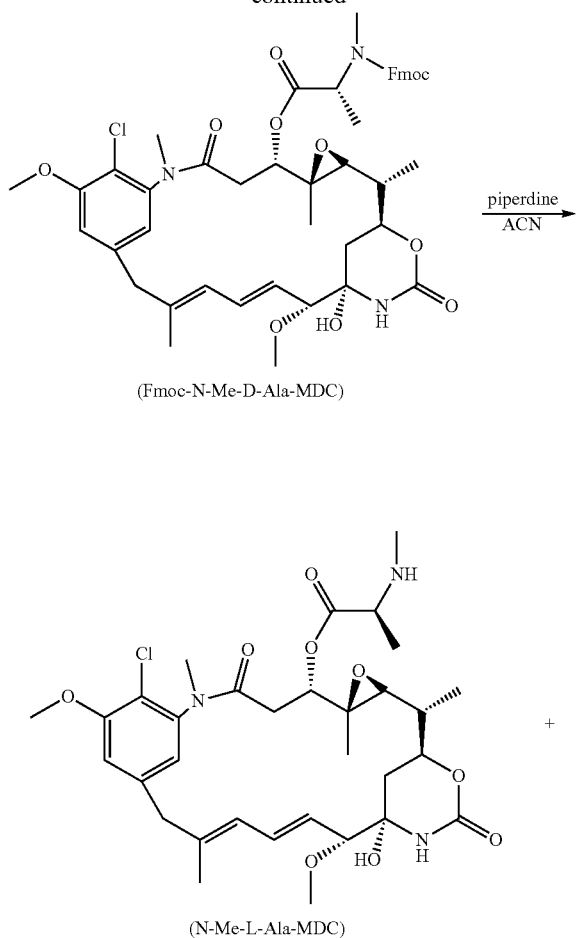

(Fmoc-N-Me-D-Ala-MDC)

(N-Me-L-Ala-MDC)

(N-Me-D-Ala-MDC)

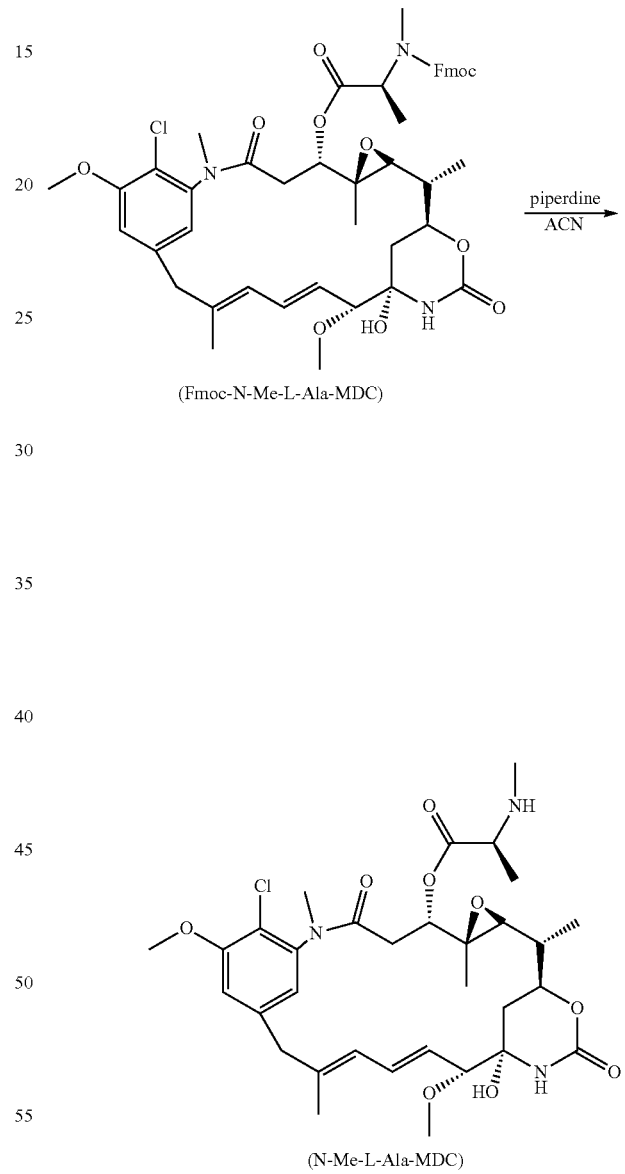

product, which was used in the next step without further purification. LC-MS (M+H⁺) calc.: 650.3. found: 650.3. Rt: 3.96 min.

Example 3

Deprotection of Fmoc-N-Me-L-Ala-MDC (N-Me-L-Ala-MDC)

(Fmoc-N-Me-L-Ala-MDC)

(N-Me-L-Ala-MDC)

Into Fmoc-N-Me-D/L-Ala-MDC (0.463 g, 0.5307 mmol) in ACN (200 mL) was added piperidine (0.865 g, 10.15 mmol). The mixture was stirred at r.t. for 4 h, quenched with water and extracted with CH$_2$Cl$_2$. The combined organic phase was washed with brine and dried over Na$_2$SO$_4$. The solvent was removed under reduced pressure to give the crude product, which was used in the next step without further purification.

Into Fmoc-N-Me-L-Ala-MDC (0.463 g, 0.5307 mmol) in ACN (200 mL) was added piperidine (0.865 g, 10.15 mmol). The mixture was stirred at r.t. for 4 h, quenched with water and extracted with CH$_2$Cl$_2$. The combined organic phase was washed with brine and dried over Na$_2$SO$_4$. The solvent was removed under reduced pressure to give the crude product, which was used in the next step without further purification. LC-MS (M+H⁺) calc.: 650.3. found: 650.3. Rt: 3.96 min.

Example 4
Condensation of N-Me-D/L-Ala-MDC with MA-ACP (D-3AA-MDC and L-3AA-MDC)
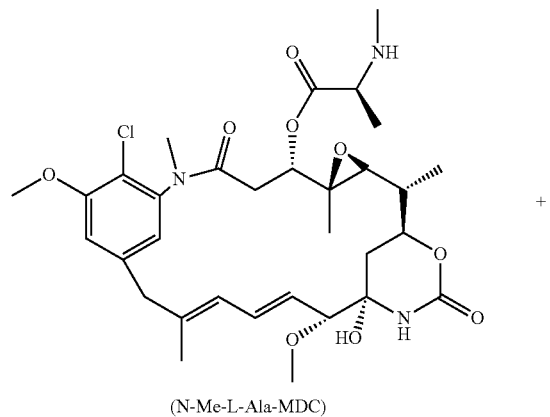
(N-Me-L-Ala-MDC)
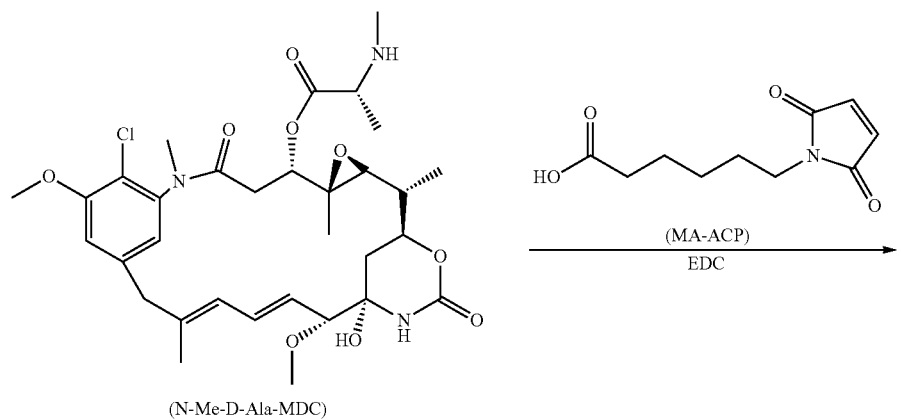
(N-Me-D-Ala-MDC)
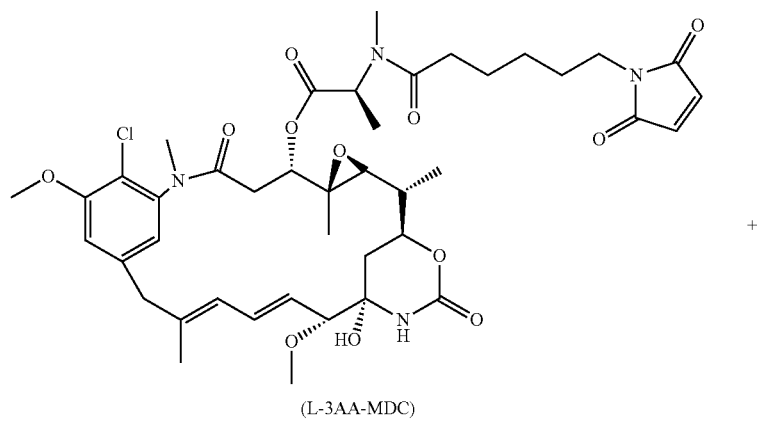
(L-3AA-MDC)

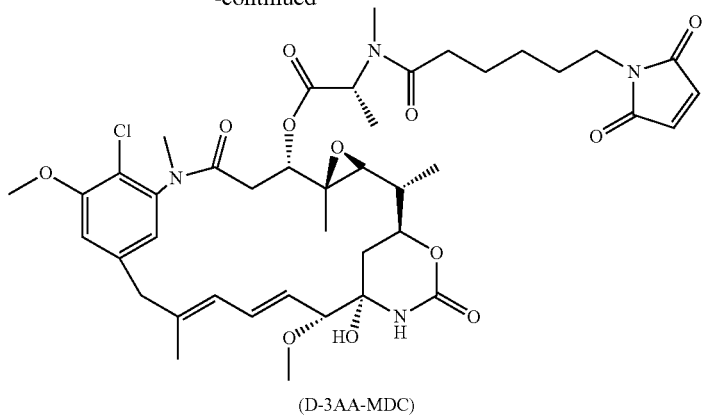

(D-3AA-MDC)

Into above prepared N-Me-D/L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EtOAc, washed with brine, and dried over $Na_2SO_4$. The solvent was removed under reduced pressure. Chromatography (silica gel: $CH_2Cl_2$/MeOH 30:1) gave the crude product. Further purification by preparative HPLC on a YMC C-18 column (250×20 mm, S 10 μm) gave two fractions (Rt=6.59 min and 6.98 min) as white solid. The higher Rt fraction was determined to be the D-aminoacyl ester diastereomer (D-3AA-MDC, 45.2%), while the lower Rt fraction was the desired L-aminoacyl ester (L-3AA-MDC, 54.8%). L-3AA-MDC: white solid (0.1364 g, 30.5% overall yield over two steps), $^1$H NMR (400 MHz, $CDCl_3$): δ0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz), 6.64 (1H, s), 6.65 (2H, s), 6.72 (1H, d, J=11.2 Hz), 6.82 (1H, s). LC-MS (M+Na$^+$) calc.: 865.3. found: 865.3. Rt: 6.59 min. D-3AA-MDC: white solid (0.1128 g, 25.2% overall yield over two steps), $^1$H NMR (400 MHz, $CDCl_3$): δ0.86 (3H, s), 1.22-1.38 (4H, m), 1.25 (3H, d, J=9.2 Hz), 1.38-1.45 (1H, m), 1.48 (3H, d, J=7.6 Hz), 1.56-1.70 (4H, m), 1.68 (3H, s), 1.75 (1H, d, J=13.6 Hz), 2.19 (1H, dd, J=14.4, 2.8 Hz), 2.28-2.36 (2H, m), 2.65 (1H, dd, J=14.2, 12.0 Hz), 2.80 (1H, d, J=9.6 Hz), 3.01 (3H, s), 3.19 (1H, d, J=13.2 Hz), 3.32 (3H, s), 3.42 (1H, d, J=9.6 Hz), 3.47-3.54 (3H, m), 3.98 (3H, s), 4.29 (1H, t, J=10.4 Hz), 4.88 (1H, dd, J=11.8, 3.2 Hz), 5.07 (1H, q, J=7.6 Hz), 5.84 (1H, dd, J=15.2, 9.2 Hz), 6.23 (1H, d, J=11.2 Hz), 6.27 (1H, s), 6.41 (1H, dd, J=15.2, 11.2 Hz), 6.69 (2H, s), 6.79 (1H, d, J=1.2 Hz), 6.84 (1H, d, J=1.2 Hz). LC-MS (M+Na$^+$) calc.: 865.3. found: 865.3. Rt: 6.98 min.

Example 5

Condensation of N-Me-L-Ala-MDC with MA-ACP (L-3AA-MDC)

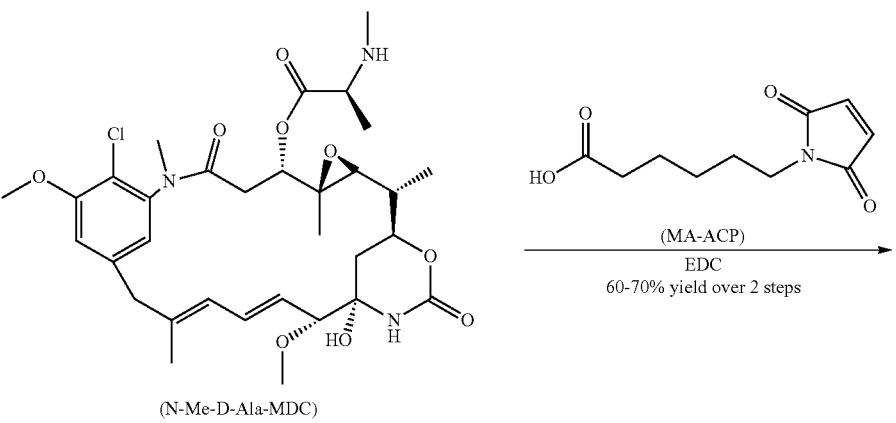

-continued

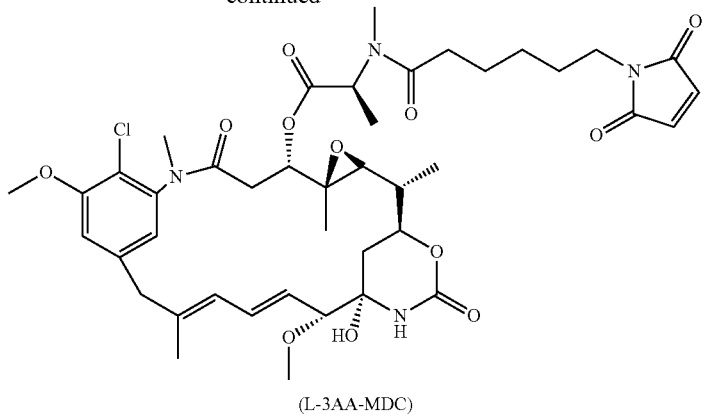

(L-3AA-MDC)

Into above prepared N-Me-L-Ala-MDC (0.5307 mmol) and MA-ACP (0.448 g, 2.123 mmol) in DMF (25 mL) under 0° C. was added EDC (0.407 g, 2.123 mmol). The mixture was stirred at r.t. overnight, quenched with water, extracted with EtOAc, washed with brine, dried over $Na_2SO_4$. The solvent was removed under reduced pressure. Chromatography (silica gel: $CH_2Cl_2$/MeOH 30:1) gave the crude product. Further purification by preparative HPLC on a YMC C-18 column (250×20 mm, S 10 μm) gave the desired L-3AA-MDC: white solid (0.280 g, 62.6% overall yield over two steps), $^1$H NMR (400 MHz, $CDCl_3$): δ0.79 (3H, s), 1.17-1.32 (3H, m), 1.27 (3H, s), 1.29 (3H, s), 1.40-1.76 (7H, m), 2.12-2.23 (2H, m), 2.31-2.45 (1H, m), 2.59 (1H, t, J=12.8 Hz), 2.82 (3H, s), 3.01 (1H, d, J=9.6 Hz), 3.10 (1H, d, J=8.8 Hz), 3.17 (3H, s), 3.34 (3H, s), 3.42 (2H, t, J=6.8 Hz), 3.48 (2H, d, J=6.8 Hz), 3.62 (1H, d, J=12.8 Hz), 3.97 (3H, s), 4.27 (1H, t, J=11.2 Hz), 4.76 (1H, d, J=11.6 Hz), 5.36 (1H, q, J=6.8 Hz), 5.65 (1H, dd, J=15.2, 9.2 Hz), 6.25 (1H, s), 6.41 (1H, dd, J=15.2, 11.2 Hz), 6.64 (1H, s), 6.65 (2H, s), 6.72 (1H, d, J=11.2 Hz), 6.82 (1H, s). LC-MS (M+Na$^+$) calc.: 865.3. found: 865.3. Rt: 6.59 min.

Example 6

Figure 6:
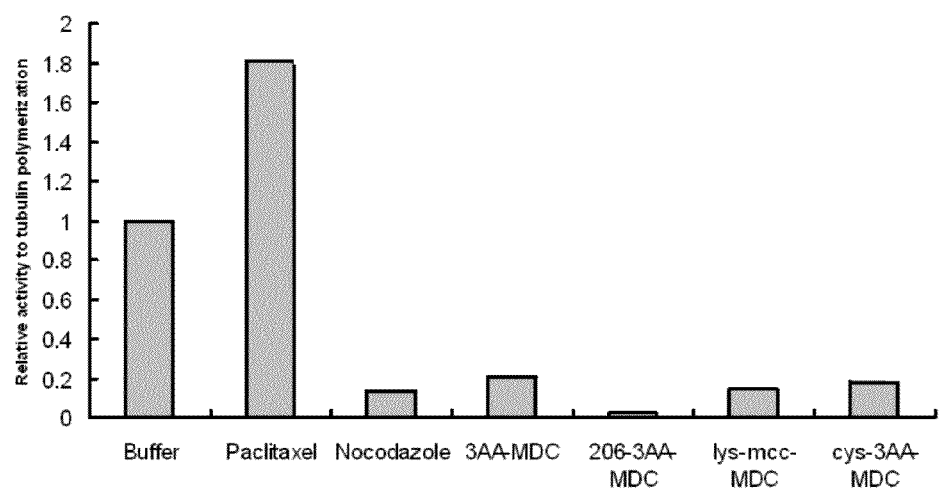
FIG. 6 shows the effects of the metabolites of prodrug antibody maytansinoid conjugates on the tubulin polymerization.

The Effect of the Metabolites of Prodrug Antibody Maytansinoid Conjugates on the Tubulin Polymerization The effect of 3AA-MDC, 206-3AA-MDC and the metabolites (Cys-3AA-MDC and Lys-mcc-MDC) of prodrug antibody maytansinoid conjugates on the tubulin polymerization in vitro was assessed by HTS-Tubulin Polymerization Assay Kit (BK004P, Cytoskeleton, Inc., USA). According to the instruction of kit, pre-warm the 96-well plate to 37° C. for 30 min prior to starting the assay. At the same time, the spectrophotometer (SpectraMax, Molecular Devices, USA) was set as follow: wavelength, 405 nm; temperature, 37° C.; Kinetic, 31 cycles of 1 reading per minute. Make cold G-PEM buffer (990 μL General Tubulin Buffer+10 μL GTP Stock) and keep it on ice. Prepare 4 mg/mL tubulin, 1 μM L-3AA-MDC ($N_2$'-deacetyl-$N_2$'-(6-maleimido-1-oxo-hexyl)maytansine), 1 μM 206-3AA-MDC, 1 μM cys-3AA-MDC, 1 μM lys-mcc-MDC, 100 μM Paclitaxel, and 100 μM Nocodazole. Add 10 μL G-PEM, 3AA-MDC, 206-3AA-MDC, cys-3AA-MDC, lys-mcc-MDC, Paclitaxel, Nocodazole into the wells, and then add 100 μL 4 mg/ml tubulin to each well. Immediately place the plate into the spectrophotometer and start recording using the kinetic setup described above. As show in the FIG. 6, compared with the PBS buffer, 3AA-MDC, Cys-3AA-MDC, Lys-mcc-MDC and 206-3AA-MDC more significantly inhibited the tubulin polymerization (FIG. 6). Nocodazole, the tubulin polymerization inhibitor, was set as a negative control. The metabolite Cys-3AA-MDC was prepared by reaction of 3AA-MDC with cysteine under the base DIEA in $CH_2Cl_2$. LC-MS (M+H$^+$) calc.: 964.5. found: 964.2. Rt: 12.97 min. The metabolite Lys-MCC-MDC was prepared by reaction of SMCC-MDC with lysine under the base DIEA in DMF. LC-MS (M+H$^+$) calc.: 1103.7. found: 1103.2. Rt: 13.00 and 13.18 min.

Example 7

Recombinant Antibody Expression and Purification

The monoclonal antibodies, Bat0206, Bat0606 (trastuzumab), Bat1206 (rituximab), which specifically bind the extracellular domain of EGFR, Her2, CD20 respectively were produced as described in CHO cells essentially as described in Wood et al., J Immunol. 145:3011 (1990). Briefly, each of the antibody genes were constructed with molecular biology techniques (Molecular Cloning: A Laboratory Manual, 3$^{rd}$ edition J. Sambrook et al., Cold spring Harbor Laboratory Press). A derivative of Chinese hamster ovary cell lines CHOK1 was grown in CD-CHO media (GIBCO). Transfections were facilitated using electroporation. Healthy mid-log CHO-K1 cells were pelleted by centrifuge and were resuspended in fresh CD-CHO media to achieve cell densities of approximately 1×10$^7$ cells (600 mL) per cuvette. Suspensions of cells containing 40 μg of linearized plasmid DNA were electroporated, seeding 10$^3$ cells per well in 96-well tissue culture plates containing suitable selection drug. The antibody expression level in the culture supernatant of clones isolated on 96-well tissue culture plates was determined by an enzyme-linked immunosorbent assay (ELISA). On the basis of the antibody titer in the supernatant, clones with high-level expression were transferred to 24-well plate (Corning) containing suitable media. Specific antibody productivity (qAb) and specific growth rate (μ) were further analyzed by seeding cells at 2×10$^5$ cells per well containing 5 ml of medium in six-well tissue culture plates, culturing for 2 and 4 days, and usually 20-30 high-producing clones (parental clones) were transferred to shake flask for successive selection, and 5-8 highest producer clones were chosen to be further subcloned, and tested for expression.

The purification was carried out by centrifuging cell suspension and harvesting the supernatant, which was further

Example 8

Conjugation of Bat0206 with SMCC-MDC

The drug-linker SMCC-MDC was prepared in the following reactions: (1) 3-mercaptopropanoic acid (MPr) was reacted with N-succinimidyl 4-(maleimidomethyl)cyclohexane-1-carboxylate (SMCC) in the presence of DIEA, giving the MPr-SMCC at a yield of over 95%; Secondly, condensation of N-Me-L-Ala-MDC, which was prepared by deprotection of Fmoc-N-Me-Ala-MDC under a base piperidine in $CH_3CN$, with MPr-SMCC under a coupling reagent EDC, giving the desired coupled product SMCC-MDC in 60-70% yield over two steps. Antibody Bat0206 (Abu) was diluted to 2.5 mg/mL in solution A (50 mM potassium phosphate, 50 mM NaCl, and 2 mM EDTA, pH 6.5). SMCC-MDC was added to give a ratio of SMCC-MDC to antibody of 7:1 mole equivalent. Then DMA was added to 15% (v/v) to the reaction and reaction was mixed by stirring for 4 h at ambient temperature. D-Lmcc-Bat0206 conjugate was purified from excess unreacted or hydrolyzed reagent and excess SMCC-MDC using a G25 gel filtration column equilibrated in pH 7.4 phosphate buffer (aqueous). The conjugate was then dialyzed overnight into pH 7.4 phosphate buffer (aqueous) and then filtered through a 0.22 μm filter for final storage. The number of SMCC-MDC molecule per Abu molecule in the final conjugate was measured by determining absorbance of the conjugate at 252 and 280 nm and using known extinction coefficients for SMCC-MDC and antibody at these two wavelengths. A ratio of maytansinoid compound to antibody of 3.5:1.0 was normally obtained.

Example 9

Conjugation of Bat0206 with Batansine

Antibody Bat0206 was diluted to 8.0 mg/mL in solution B (50 mM potassium phosphate, 50 mM NaCl, and 2 mM EDTA, pH 8.0). Partial reduction was carried out with (6 moles equivalent) DTT. After incubation at 37° C. for 60 minutes, the buffer was exchanged by elution through Sephadex G-25 resin with solution B. The thiol-antibody value was determined from the reduced monoclonal antibody (mAb) concentration determined from 280-nm absorbance, and the thiol concentration was determined by reaction with DTNB (5,5'-dithiobis(2-nitrobenzoic acid); Aldrich) and absorbance measured at 412 nm.

The conjugation reaction was carried out with 10% DMA. The batansine (3AA-MDC) was prepared as in Example 4 and 5 above. The volume of batansine solution was calculated to contain 1.5-mol batansine (3AA-MDC) per mol thiol equivalent. Batansine solution was added rapidly with mixing to the cold-reduced antibody solution, and the mixture was stirred at r.t. for 3 hours, and continued for additional 1 h after adding 5 mM cysteine. The reaction mixture was concentrated by centrifugal ultrafiltration and buffer-exchanged by elution through Sephadex G25 equilibrated in PBS. The conjugate was then filtered through a 0.2-μm filter under sterile conditions and stored at –80° C. for analysis and testing. The Batansine-0206 was further analyzed for drug/antibody ratio by measuring unreacted thiols with DTNB, and 3.5:1 ratio of drug/antibody was often obtained. Batansine-0206 was further characterized for concentration by UV absorbance, aggregation by size-exclusion chromatography, and residual free drug by reverse-phase HPLC. All mAbs and ADCs used in these studies exceeded 98% monomeric protein.

Example 10

Characterization of Batansine-0206

Figure 7:
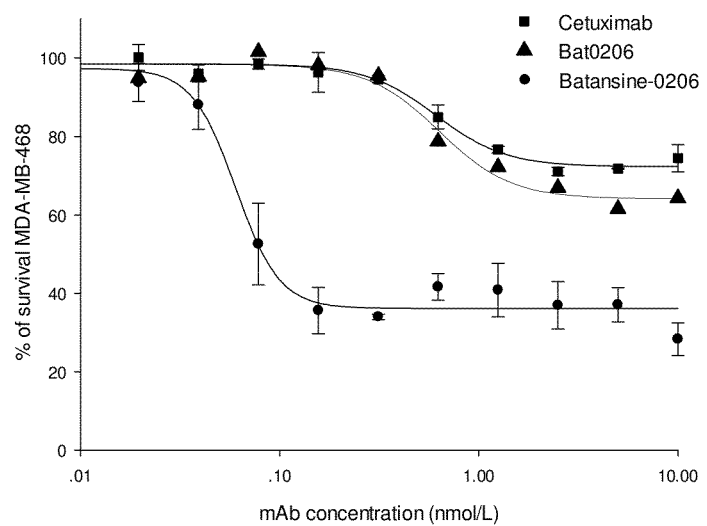
FIG. 7 shows that Bat0206 and Batansine-0206 inhibited tumor cell growth.
Figure 8:
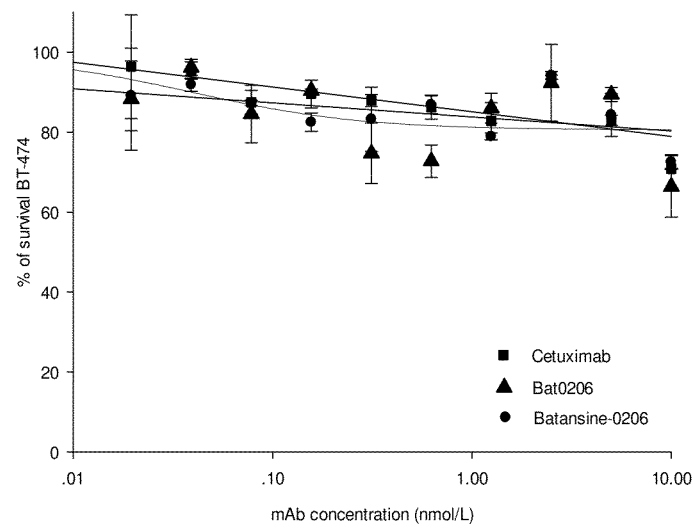
FIG. 8 shows that Bat0206, cetuximab, Batansine-0206 has no inhibitory effect on EGFR negative cells.
Figure 9:
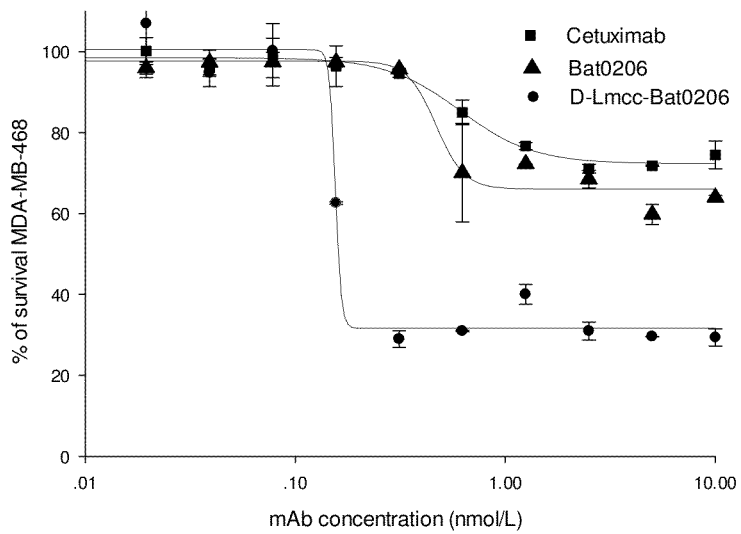
FIG. 9 shows the inhibitory effect of D-Lmcc-Bat0206 towards MDA-MB-468 cells.

The growth inhibitory characteristics of Bat0206 and Batansine-0206 were evaluated using the EGFR positive breast tumor cell line, MDA-MB-468 and EGFR negative cell line BT474 (Shanghai Cell Collections, Ltd. Co., Shanghai, China). Briefly, cells were detached by using 0.25% (vol/vol) trypsin and suspended in complete medium. Aliquots of 100 μL containing 10,000 cells were plated into 96-well microplates. The cells were allowed to adhere overnight at 37° C., and 100 μL of media containing various concentrations of Bat0206 and Batansine-0206 was then added. After 72 hours, plates were washed twice with PBS (pH 7.5), and analyzed for relative cell proliferation with Cell Counting Kit-8 (CCK-8, Dojindo Molec. Technologies, Japan) reagent. Drug conjugate Batansine-0206 significantly inhibited the EGFR positive cell proliferation at much lower concentration than naked Bat0206 and naked Cetuximab (FIG. 7). Neither naked antibodies Bat0206, naked marked antibody Cetuximab, nor drug conjugate Batansine-0206 inhibited the growth of EGFR negative cell line BT474 (FIG. 8).

Example 11

Preparation of Antibody-Drug Conjugates: D-Lmcc-Bat0206

Antibody Bat0206 was diluted to 2.5 mg/mL in solution A (50 mM potassium phosphate, 50 mM NaCl, and 2 mM EDTA, pH 6.5). SMCC-MDC was added to give a ratio of SMCC-MDC to antibody of 7:1 mole equivalent. Then DMA was added to 15% to the reaction and reaction was mixed by stirring for 4 h at ambient temperature. D-Lmcc-Bat0206 conjugate was purified from excess unreacted or hydrolyzed reagent and excess SMCC-MDC using a G25 gel filtration column equilibrated in pH 7.4 phosphate buffer (aqueous). The conjugate was then dialyzed overnight into pH 7.4 phosphate buffer (aqueous) and then filtered through a 0.22 μm filter for final storage. The number of SMCC-MDC molecule per Abu molecule in the final conjugate was measured by determining absorbance of the conjugate at 252 and 280 nm and using known extinction coefficients for SMCC-MDC and antibody at these two wavelengths. A ratio of maytansinoid compound to antibody of 2-5 to 1 was normally obtained.

Figure 10:
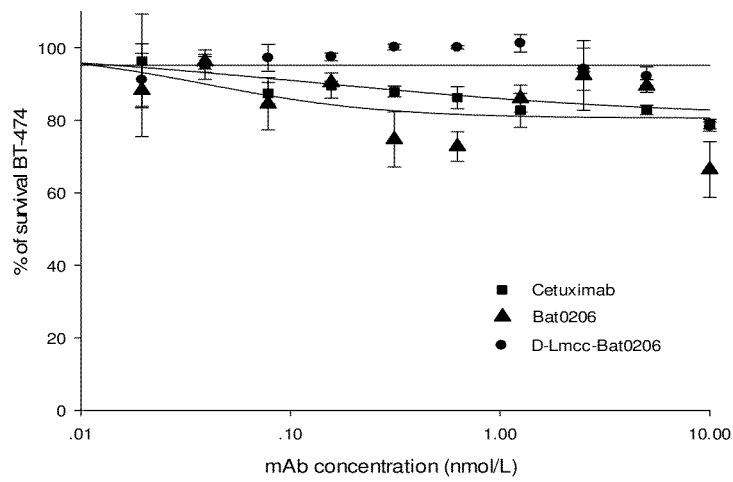
FIG. 10 shows that Bat0206, cetuximab, D-Lmcc-Bat0206 has no inhibitory effect on EGFR negative cells.

The growth inhibitory characteristics of D-Lmcc-Bat0206 were also evaluated using the EGFR positive breast tumor cell line, MDA-MB-468 and EGFR negative cell line BT474. Briefly, cells were detached by using 0.25% (vol/vol) trypsin and suspended in complete medium. Aliquots of 100 μL containing 10,000 cells were plated into 96-well microplates. The cells were allowed to adhere overnight at 37° C., and 100 μL of media containing various concentrations of Bat0206 and D-Lmcc-bat0206 was then added. After 72 hours, plates were washed twice with PBS (pH 7.5), and analyzed for relative cell proliferation with CCK-8 reagent. Drug conjugate D-Lmcc-Bat0206, as in the case of Batansine-0206, significantly inhibited the EGFR positive cell proliferation at much lower concentration than naked Bat0206 and naked Cetuximab (FIG. 10).

Example 12

D-Lmcc-Bat0206 Eradicates Human A431 Tumor Xenografts

Figure 11:
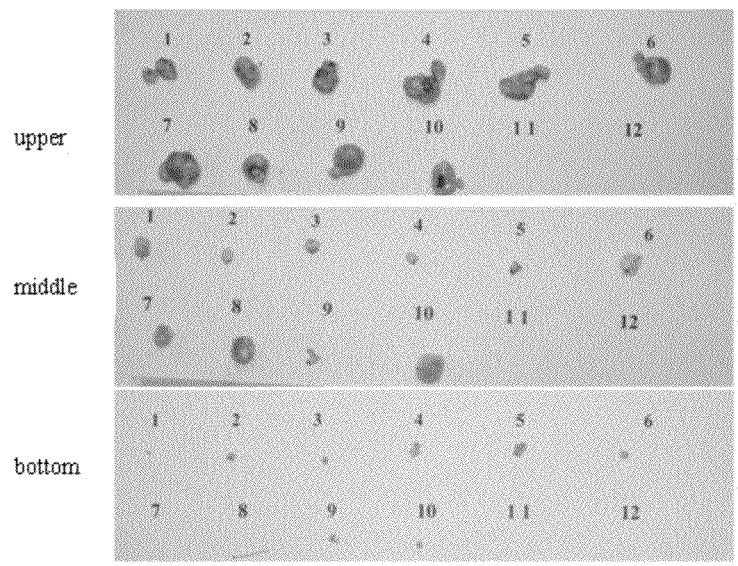
FIGS. 11 and 12 shows that D-Lmcc-Bat0206 eradicated A431 tumor xenographs.
Figure 12:
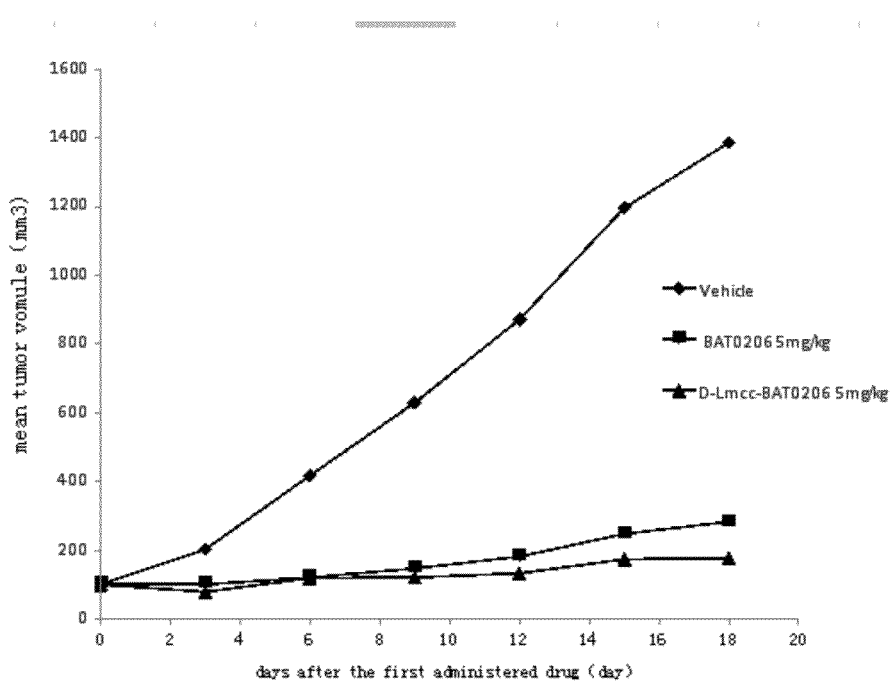

In Vivo Tumor Studies: The effects of D-Lmcc-Bat0206 on the growth of established tumors were examined on human A431 tumor xenografts. Human A431 cells (ATCC, CRL-7907) were cultured in DMEM medium supplemented with 10% fetal bovine serum, 2 mM glutamine and antibiotics. Female BALB/c nude mice, 4-6 weeks old, were injected subcutaneously with $4 \times 10^6$ tumor cells in the dorsal area in a volume of 100 µL. When the tumor xenografts reaches a size of 80-200 mm$^3$ (calculated as 0.5 (length×width$^2$), animals were then treated with Bat0206, D-Lmcc-Bat0206, or a control buffer. Bat0206 and D-Lmcc-Bat0206 were administered at the doses of 5 mg/kg. Animals were dosed every 3 days for a total of 8 doses i.p. in a volume of 100 µL. Each group consisted of 12 mice. Tumor size was determined at 3 days intervals. Twenty four days after tumor cell inoculation, animals were euthanized and tumors were removed and weighed. As shown in FIGS. 11 and 12, at 5 mg/kg dose tested, Bat0206 and D-Lmcc-Bat0206 markedly suppressed tumor growth as assessed by tumor weight measurements 24 days after drug treatment.

Example 13

Preparation of Antibody-Drug Conjugate D-LSPP-Bat0206

Antibody Bat0206 (8 mg/mL) was modified using 8-fold molar excess of N-succinimidyl-4-(2-pyridyldithio) pentanoate (SPP) to introduce dithiopyridyl groups. The reaction was carried out in 95% v/v Buffer A (50 mM potassium phosphate, 50 mM NaCl, 2 mM EDTA, pH 6.5) and 5% v/v DMA for 2 h at room temperature. The slightly turgid reaction mixture was gel-filtered through a Sephadex G25 column (equilibrated in Buffer A). The degree of modification was determined by measuring the absorbance of the antibody and the 2-mercaptopyridine (Spy) released by DTT respectively at 280 and 343 nm. Modified Bat0206 was then conjugated at 2.5 mg/mL using a 1.7-fold molar excess of $N_2$'-deacetyl-$N_2$'-(3-mercapto-1-oxopropyl)-maytansine over SPy. The reaction was carried out with DMA (5% v/v) in Buffer A (see above). The reaction was incubated at room temperature overnight for 17 h. The conjugated antibody was cleared by centrifugation and then further purified through gel-filtration with a Sephadex G25 column equilibrated with PBS pH 6.5. The conjugate was sterile-filtered using a 0.22 µM Millex-GV filter. The number of drug molecules linked per Bat0206 molecule was determined by measuring the absorbance at both 252 nm and 280 nm of the filtered material. The drug to antibody ratio was found to be about 4.5. The conjugated antibody was further biochemically characterized by size exclusion chromogaphy (SEC) and found to be over 96% monomer.

Figure 13:
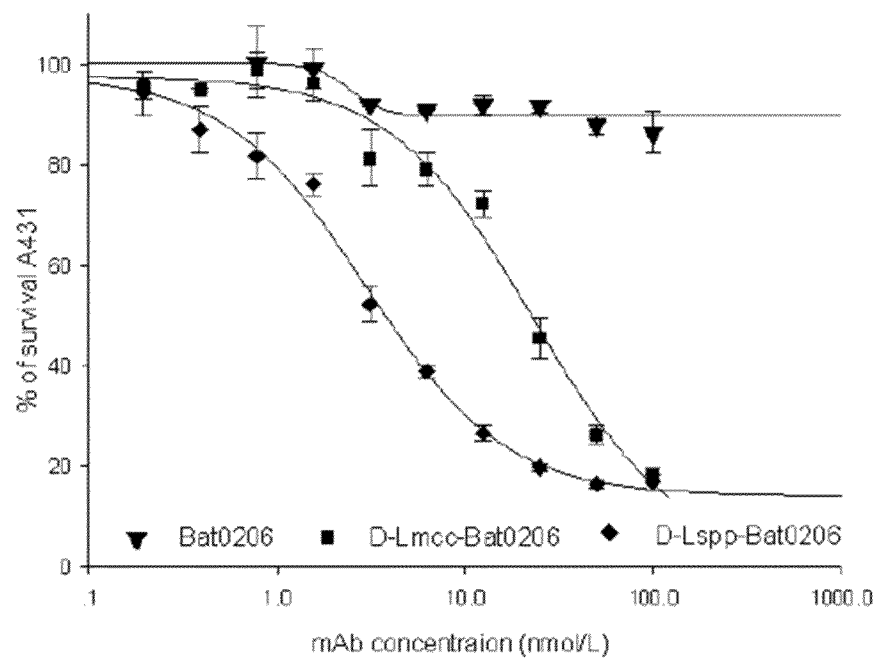
FIG. 13 shows that D-Lmcc-Bat0206 and D-Lspp-Bat0206 inhibited A431 tumor cells.
Figure 14:
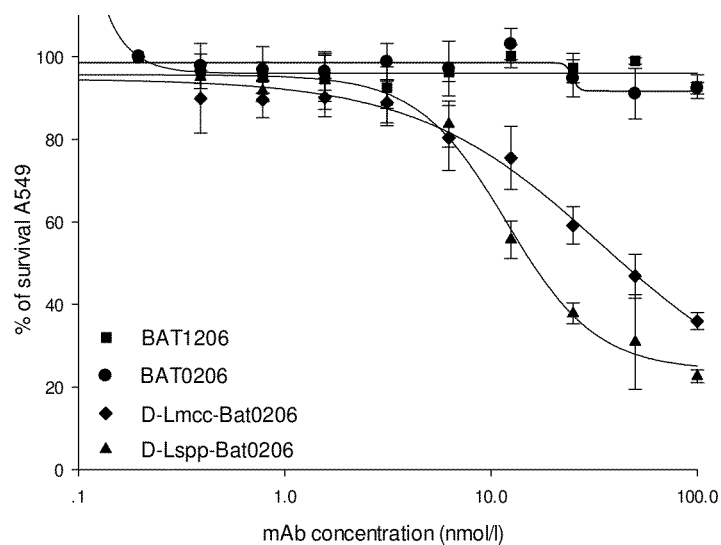
FIG. 14 shows D-Lmcc-Bat0206 and D-Lspp-Bat0206 inhibited A549 tumor cells.
Figure 16:
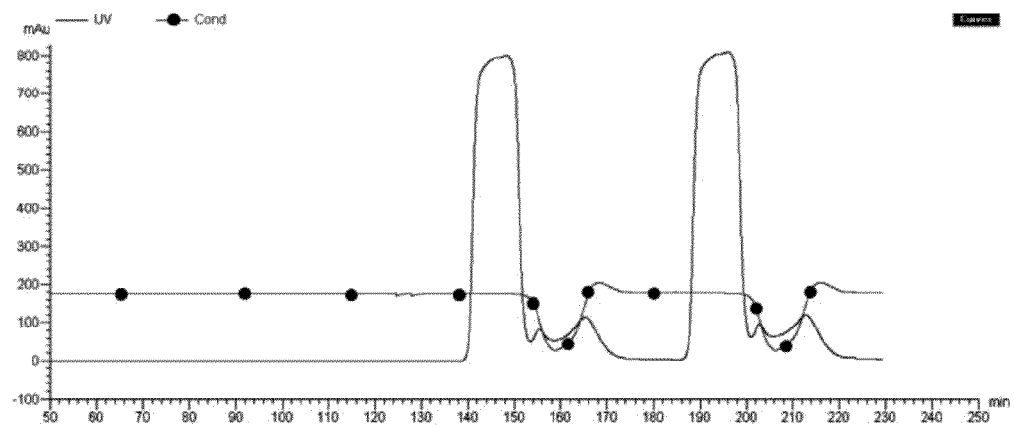
FIGS. 16 and 17 show the processing of D-Lmcc-bat0606 and Batanine-0606 using Sephadex G-25.
Figure 17:
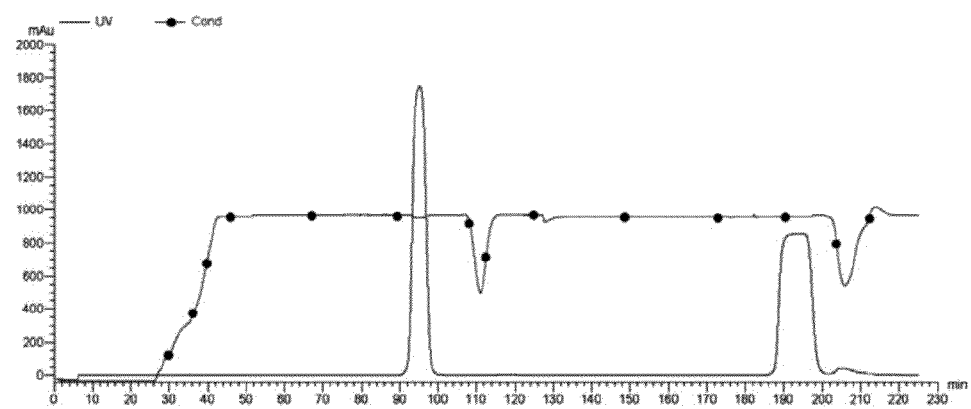
Figure 18:
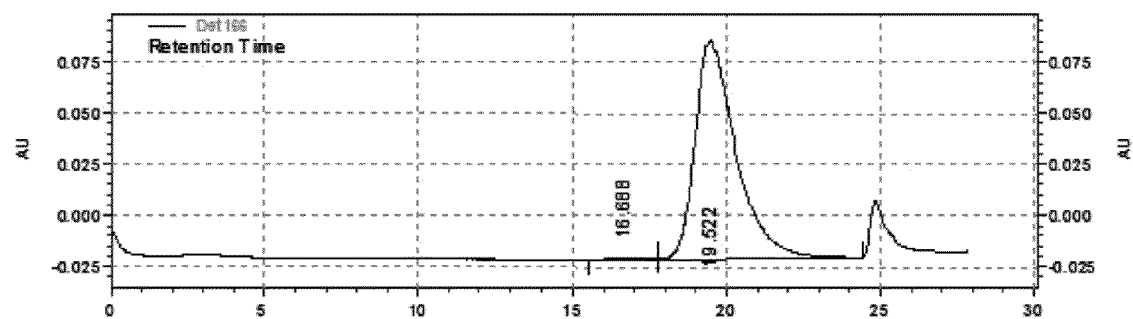
FIGS. 18 and 19 show the size exclusion chromatograph of D-Lmcc-bat0606 and Batanine-0606 respectively.
Figure 19:
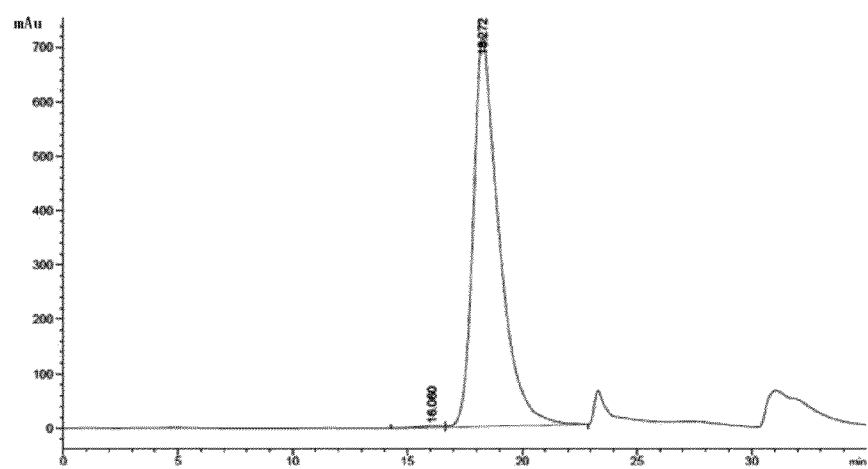

The growth inhibitory characteristics of D-Lspp-Bat0206 were evaluated using the EGFR positive tumor cell line A431 and A549. Briefly, cells were detached by using 0.25% (vol/vol) trypsin and suspended in complete medium. Aliquots of cells were plated into 96-well microdilution plates. The cells were allowed to adhere overnight at 37° C., and 100 µL of media containing various concentrations of Bat0606 and D-Lspp-Bat0206 was then added. After 72 hours, plates were washed twice with PBS (pH 7.5), and analyzed for relative cell proliferation with CCK-8 reagent. Drug conjugate D-Lspp-Bat0206 significantly inhibited the A431 positive cell proliferation at much lower concentration than naked Bat0206 (FIG. 13), and furthermore, D-Lspp-bat0206 effectively inhibited the growth of A549 cells, which is resistant to treatment by naked Bat0206 as a result of Kras mutation (FIG. 14).

The $IC_{50}$ values of certain compounds are presented in Tables 1 and 2. The data in Table 2 are obtained with conjugates having different drug loads and using different experimental conditions.

Batansine-0206 and D-Lmcc-Bat0206 significantly increased the activity of the naked antibody against EGFR positive tumor cell lines. Compared with the di-sulfide comprising drug-linker-antibody D-Lspp-Bat0206, Batansine-0206 and D-Lmcc-Bat0206 exhibited significant improvement in selectivity against EGFR positive tumor cell lines A431 and MDA-MB-468. Surprisingly, Batansine-0206 and D-Lmcc-Bat0206 also exhibited significant improvement in selectivity against EGFR positive tumor cell lines A431 and MDA-MB-468 over the naked antibody.

TABLE 1

| Cell line | $IC_{50}$ Bat0206 | $IC_{50}$ D-Lmcc-Bat0206 | $IC_{50}$ D-Lspp-Bat0206 | $IC_{50}$ Batansine-0206 |
| --- | --- | --- | --- | --- |
| A431 | >100 nM | 22 nM | 2.9 nM | 0.17 nM |
| MDA-MB-468 | 0.46 nM | 0.15 nM | 0.10 nM | 0.06 nM |
| HCT116 | >100 nM | 53.24 nM | 0.96 nM | 44.22 nM |

TABLE 2

| Cell line | $IC_{50}$ Bat0606 | $IC_{50}$ D-Lmcc-Bat0606 | $IC_{50}$ Batansine-0606 |
| --- | --- | --- | --- |
| Her2 positive breast tumor cell line SK-BR-3 | 0.287 nM | 0.099 nM | 0.041 nM |
| EGFR negative Her2-positive breast cancer cells BT474 | 0.791 nM | 0.257 nM | 0.474 nM |
| Her2-overexpressing human gastric cancer cell line NCI-N87 | 0.221 nM | | 0.139 nM |

Example 14

Batansine-0606 Eradicates Human BT474 Tumor Xenografts

Figure 30:
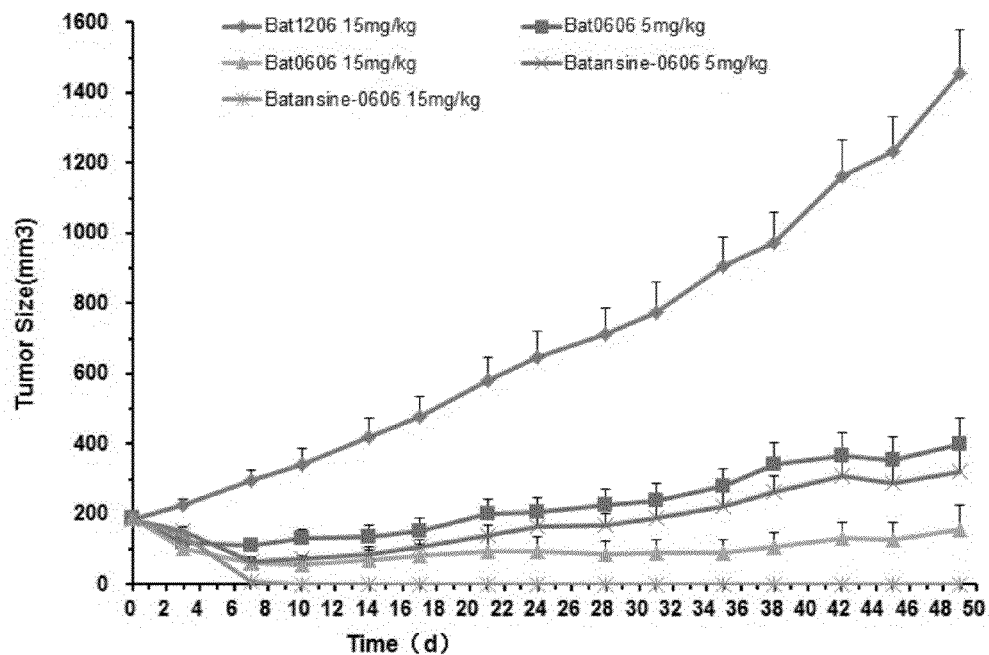
FIG. 30 shows Batansine-0606 eradicated human BT474 tumor in mouse xenografts.
Figure 31:
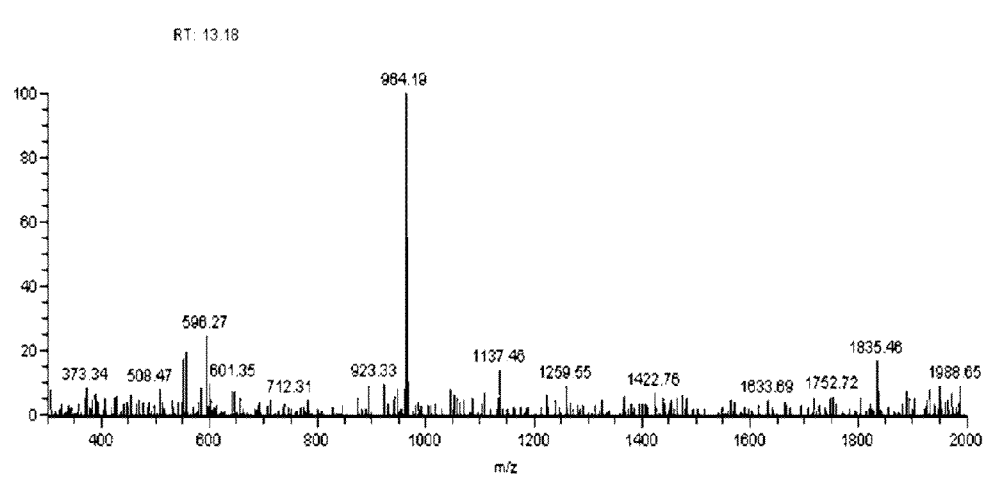
FIG. 31 shows the ESI-MS spectra of the metabolite (Batansine-Cysteine) from the prodrug Batansine-0606.
Figure 32:
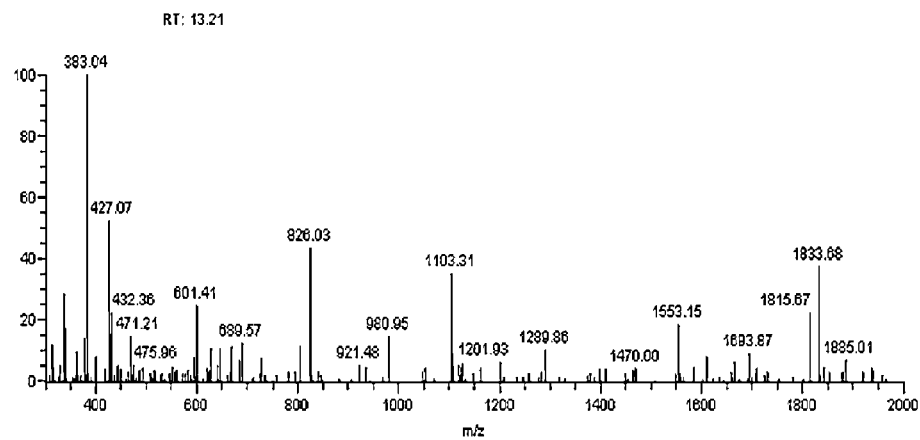
FIG. 32 shows the ESI-MS spectra of the two diastereomeric metabolites (MDC-MCC-Lysine) from the prodrug D-Lmcc-Bat0606.
Figure 32:
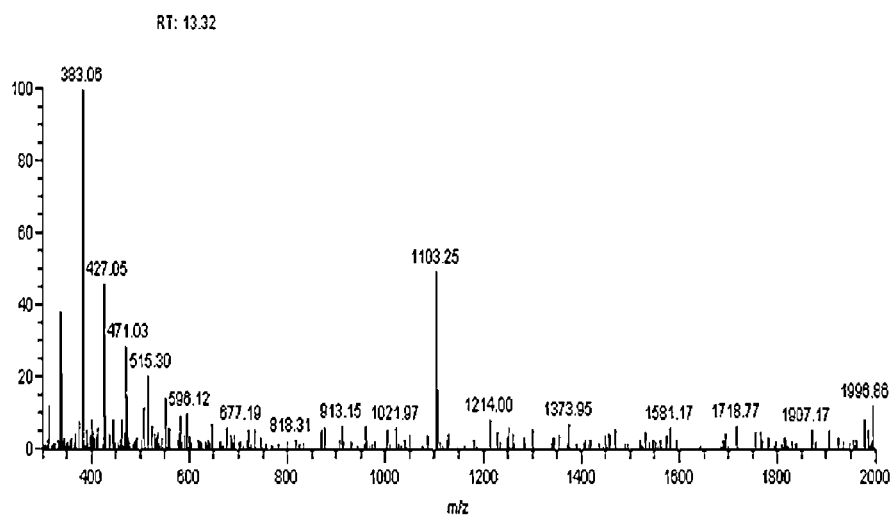

In Vivo Tumor Studies: The effects of batansine-0606 (3AA-MDC-trastuzumab) on the growth of established tumors were examined on human BT474 tumor xenografts. Human BT474 cells (ATCC, HTB-20) were cultured in DMEM medium supplemented with 10% fetal bovine serum, 2 mM glutamine and antibiotics. Female BALB/c nude mice, 8-9 weeks old, were injected subcutaneously with $1 \times 10^7$ tumor cells in the dorsal area in a volume of 100 µL. When the tumor xenografts reaches a size of 150-200 mm$^3$ (calculated as 0.5× (length×width), animals were then treated with Bat0606 (5 or 15 mg/kg), batansine-0606 (5 or 15 mg/kg), or control antibody (Rituximab, 15 mg/kg). Animals were dosed every 3 weeks for a total of 3 doses i.v. in a volume of 100 µL. Each group consisted of 10 mice. Tumor size was determined at 3 days intervals. 49 days after tumor cell inoculation, animals were euthanized and tumors were removed and weighed. As shown in FIG. 30, Rapid tumor shrinkage was seen by batansine-0606 (15 mg/kg) from day 7. From day 10 onwards batansine-0606 (15 mg/kg) treated tumors had shrunken to non-palpable. Compared to the unconjugated Bat0606, batansine-0606 more significantly inhibited the tumor growth as assessed by tumor weight measurements 49 days after drug treatment.

Example 15

Preparation of Antibody-Drug Conjugates: D-Lmcc-Bat0606

Antibody Bat0606 was diluted to 2.5 mg/mL in solution A (50 mM potassium phosphate, 50 mM NaCl, and 2 mM EDTA, pH 6.5). SMCC-MDC was added to give a ratio of SMCC-MDC to antibody of 7:1 mole equivalent. Then DMA was added to 15% to the reaction and reaction was mixed by stirring for 4 h at ambient temperature. D-Lmcc-bat0606 conjugate was purified from excess unreacted or hydrolyzed reagent and excess SMCC-MDC using a G25 gel filtration column equilibrated in pH 7.4 phosphate buffer (aqueous). The conjugate was then dialyzed overnight into pH 7.4 phosphate buffer (aqueous) and then filtered through a 0.22 μm filter for final storage. The number of SMCC-MDC molecule per Abu molecule in the final conjugate was measured by determining absorbance of the conjugate at 252 and 280 nm and using known extinction coefficients for SMCC-MDC and antibody at these two wavelengths. A ratio of maytansinoid compound to antibody of 3.5:1.0 was normally obtained.

Example 16

Preparation of Antibody-Drug Conjugates: Batansine-0606

Antibody Bat0606 was diluted to 8.0 mg/mL in solution B (50 mM potassium phosphate, 50 mM NaCl, and 2 mM EDTA, pH 8.0). Partial reduction was carried out with (6 moles equivalent) DTT. After incubation at 37° C. for 60 minutes, the buffer was exchanged by elution through Sephadex G-25 resin with solution B. The thiol-antibody value was determined from the reduced monoclonal antibody (mAb) concentration determined from 280-nm absorbance, and the thiol concentration was determined by reaction with DTNB (5,5'-dithiobis(2-nitrobenzoic acid); Aldrich) and absorbance measured at 412 nm.

The conjugation reaction was carried out with 10% DMA. The volume of batansine solution was calculated to contain 1.5-mol batansine (3AA-MDC) per mol equivalent of free thiol on the antibody. Batansine solution was added rapidly with mixing to the cold-reduced antibody solution, and the mixture was stirred at r.t. for 3 hours, and continued for additional 1 h after adding 5 mM cysteine. The reaction mixture was concentrated by centrifugal ultrafiltration and buffer-exchanged by elution through Sephadex G25 equilibrated in PBS. The conjugate was then filtered through a 0.2-μm filter under sterile conditions and stored at −80° C. for analysis and testing. The Batansine-0606 was further analyzed for drug/antibody ratio by measuring unreacted thiols with DTNB, and 3.5:1.0 ratio of drug/antibody was often obtained. Batansine-0206 was further characterized for concentration by UV absorbance, aggregation by size-exclusion chromatography, and residual free drug by reverse-phase HPLC. All mAbs and ADCs used in these studies exceeded 98% monomeric protein.

Example 17

Characterization of Anti-ErbB2 Antibody Drug Conjugate Batansine-0606

Figure 20:
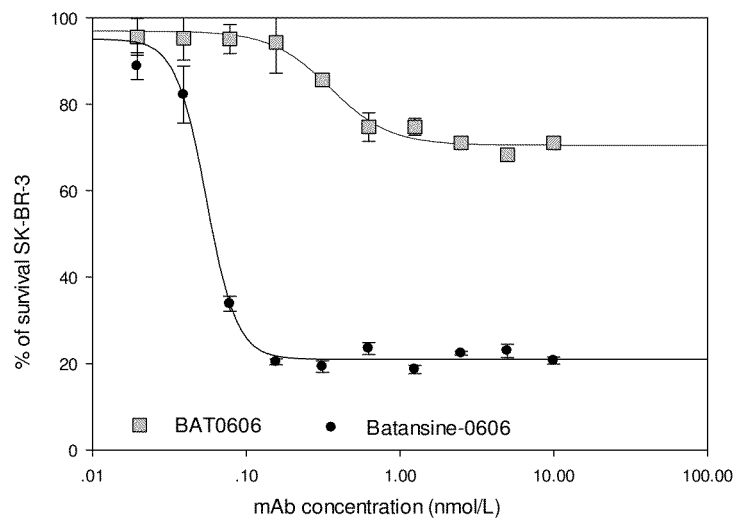
FIG. 20 shows the inhibitory effects of Bat0606 and Batanine-0606 on Her2 (SK-BR-3) cells.
Figure 21:
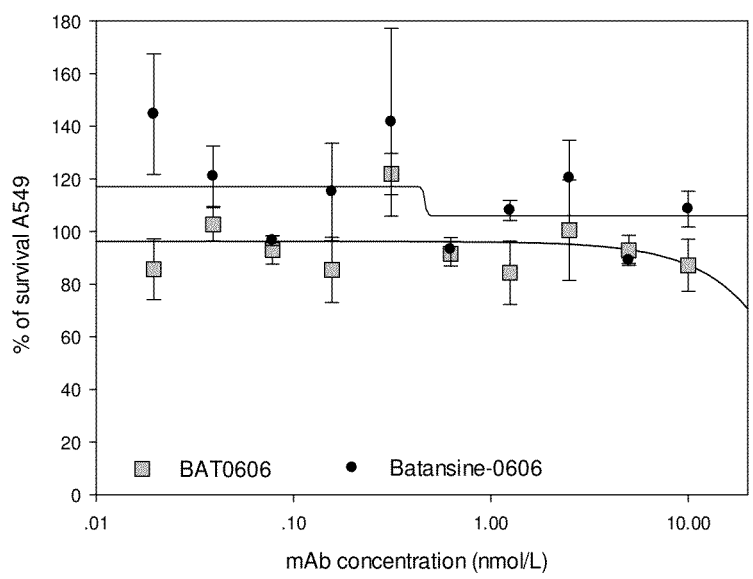
FIG. 21 shows that Bat0606 and Batanine-0606 did not inhibit A549.

The growth inhibitory characteristics of Bat0606 and Batansine-0606 were evaluated using the Her2 positive breast tumor cell line, SK-BR-3 (see Hudziak et al. Molec. Cell. Biol. 9(3):1165 1172 (1989) and Her2 negative cell line A549 [Shanghai Cell Collections, Ltd., Co., Shanghai, China]. Briefly, cells were detached by using 0.25% (vol/vol) trypsin and suspended in complete medium. Aliquots of 100 μL containing 10,000 cells for SK-BR-3 cell line and 8,000 cells for A549 cell line were plated into 96-well microdilution plates. The cells were allowed to adhere overnight at 37° C., and 100 μL of media containing various concentrations of Bat0606 and Batansine-0606 was then added. After 72 hours, plates were washed twice with PBS (pH 7.5), and analyzed for relative cell proliferation with CCK-8 reagent. Drug conjugate Batansine-0606 more significantly inhibited the Her2 positive cell proliferation than naked Bat0606 (FIG. 20). Neither naked antibody Bat0606 nor drug conjugate Batansine-0606 inhibited the growth of Her2 negative cell line A549 (FIG. 21).

Example 18

Characterization of Anti-ErbB2 Antibody Drug Conjugate D-Lmcc-Bat0606

Figure 22:
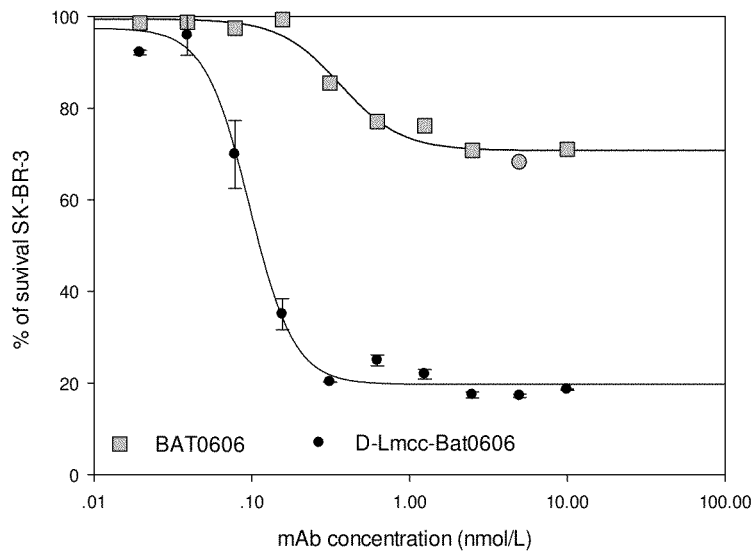
FIG. 22 shows the inhibitory effect of D-Lmcc-Bat0606 on SK-BR-3.
Figure 23:
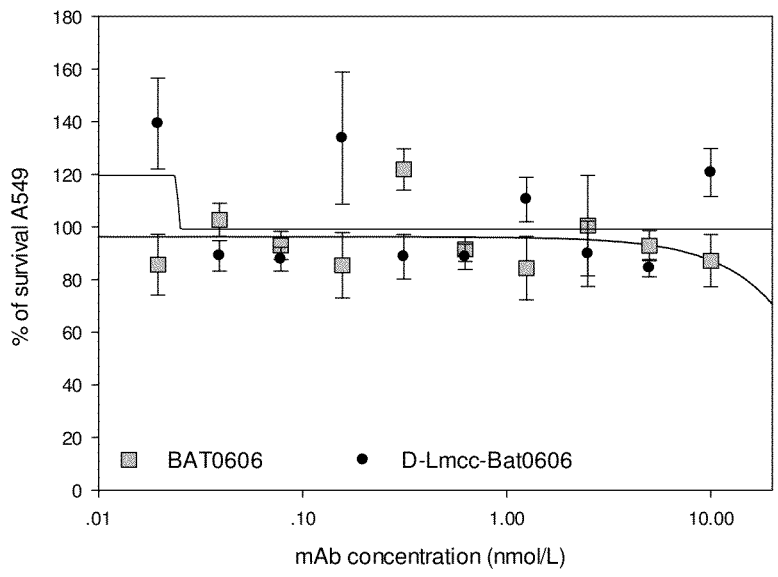
FIG. 23 shows that Bat0606 and D-Lmcc-Bat0606 did not inhibit A549 cells.
Figure 24:
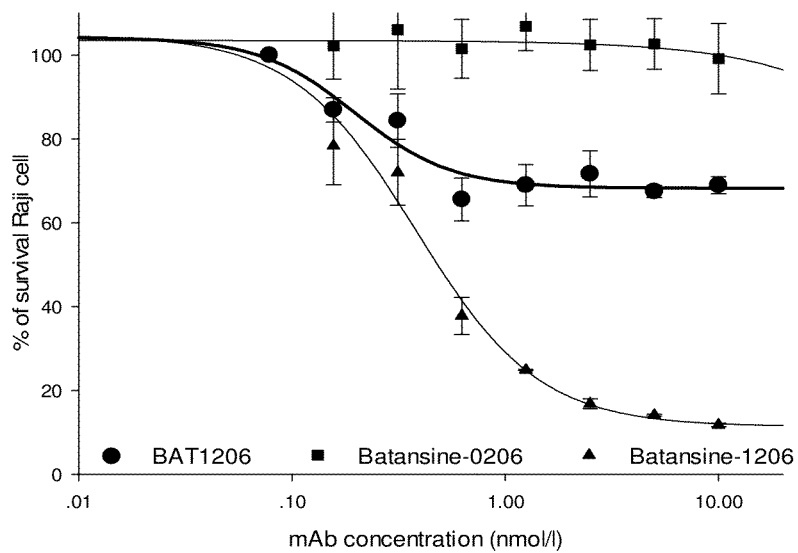
FIG. 24 shows the inhibitory effects of Bat1206 and Batansine-1206 on Raji cells.
Figure 25:
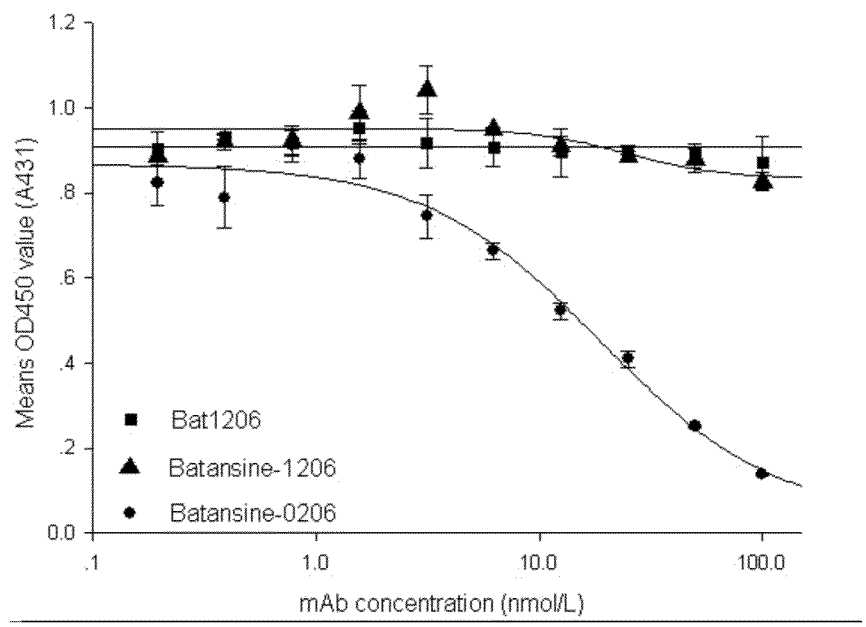
FIG. 25 shows that Bat1206 and Batansine-1206 had no effects on A431 cells.

The growth inhibitory characteristics of D-Lmcc-bat0606 were evaluated using the Her2 positive breast tumor cell line, SK-BR-3 (see Hudziak et al. Molec. Cell. Biol. 9(3):1165 1172 (1989) and Her2 negative cell line A549. Briefly, cells were detached by using 0.25% (vol/vol) trypsin and suspended in complete medium. Aliquots of 100 μL containing 10,000 cells for SK-BR-3 cell line and 8,000 cells for A549 cell line were plated into 96-well microdilution plates. The cells were allowed to adhere overnight at 37° C., and 100 μL of media containing various concentrations of Bat0606 and D-Lmcc-Bat0606 was then added. After 72 hours, plates were washed twice with PBS (pH 7.5), and analyzed for relative cell proliferation with CCK-8 reagent. Drug conjugate D-Lmcc-Bat0606 strongly inhibited the Her2 positive cell proliferation (FIG. 22). Neither naked antibody Bat0606 nor drug conjugate D-Lmcc-Bat0606 inhibited the growth of Her2 negative cell line A549 (FIG. 23).

Example 19

The stability studies of Batansine-0606 were evaluated in Sprague-Dawley rats. Sprague-Dawley rats were administered 10 mg/kg Batansine-0606 (based on the antibody component) by tail vein injection. Blood samples were collected from each mouse via the saphenous vein at 0 h, 10 min, 30 min, 1 h, 2 h, 4 h, 8 h, 24 h, 36 h, day 2, day 3, day 4, day 7, day 14, day 21, day 28 after injection. Blood was collected into heparin coated tubes followed by centrifugation (14, 000×g, 3 minutes) to isolate plasma. Plasma concentrations of total Anti-Erb B/neu and antibody-drug conjugates were measured by ELISA. Total antibody concentration in the serum samples was measured as follows: 96-well ELISA plates were coated with HER2 ECD in 2 μg/mL carbonate/bicarbonate buffer (pH 9.6) at 4° C. overnight. After removal of the coat solution, nonspecific binding sites were blocked by incubating with blocking solution (PBS, 1% BSA, 0.05% Tween 20) at room temperature for 1 hour. The plates were then washed with wash buffer (0.05% Tween in PBS), and standards or samples diluted in PBS were added. After a 2 h incubation, plates were washed and mouse anti-human IgG-horseradish peroxidase conjugate (Sigma, St. Louis, Mo.) was added for an additional 2 h. Plates were then washed again. Subsequently, 100 μL of 3,3,5,5-tetramethylbenzidine (Sigma, St. Louis, Mo.) were added to each well, and upon color development, the reaction was stopped with 100 μL of 1 N sulfuric acid. Absorbance was measured using a VMax Kinetic Microplate reader (Molecular Devices, Sunnyvale, Calif.) at 490 nm. For measurement of antibody-drug conjugates concentration, wells were coated with HER2 ECD and serum samples added as above. After the 2-h sample incubation, the plates were washed, rabbit anti-maytansine antibody was added to each well, and the plates were incubated for 1 h. Plates were then washed, and HRP-conjugated goat anti-rabbit IgG (Sigma) was added for an additional 1 h incubation. Color detection and measurement were performed as described above. Noncompartmental pharmacokinetic parameters were calculated with WinNonlin (Pharsight, Mountain View, Calif.). The time-concentration curves of antibody component of Batansine-0606 and the drug component of Batansine-0606 appeared to follow bi-exponential declines. The terminal half-life of antibody component of Batansine-0606 was 571.07, and the terminal half-life of drug component of Batansine-0606 was 88.36 hours.

Example 20

Batansine-0606 Eradicates Human NCI-N87 Tumor Xenografts

Figure 29:
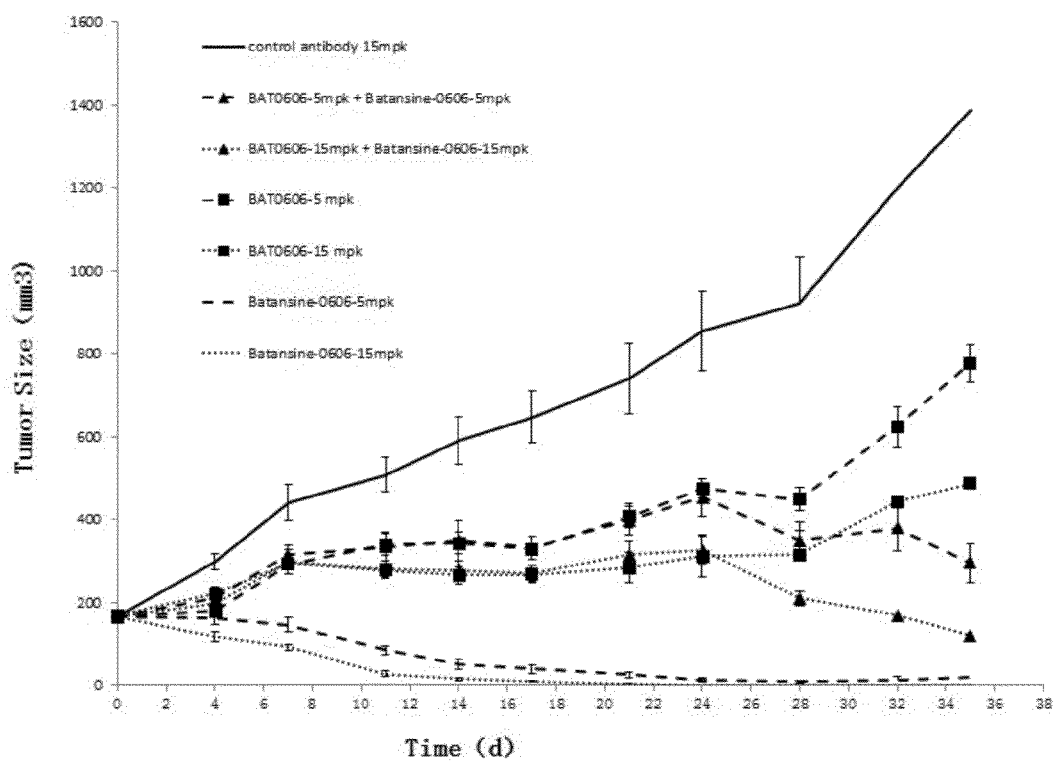
FIG. 29 shows Batansine-0606 eradicated human NCI-N87 tumor in mouse xenografts.

In Vivo Tumor Studies: The effects of batansine-0606 (3AA-MDC-trastuzumab) on the growth of established tumors were examined on human NCI-N87 tumor xenografts. Human NCI-N87 cells (ATCC, CRL-5822) were cultured in DMEM medium supplemented with 10% fetal bovine serum, 2 mM glutamine and antibiotics. Female BALB/c nude mice, 4-8 weeks old, were injected subcutaneously with $5 \times 10^6$ tumor cells in the dorsal area in a volume of 100 μL. When the tumor xenografts reaches a size of 100-200 mm$^3$ (calculated as 0.5× (length×width)), animals were then treated with Bat0606 (5 or 15 mg/kg, i.v), batansine-0606 (5 or 15 mg/kg, i.v), or control antibody (Rituximab, 15 mg/kg, i.v). Animals were dosed once per week for a total of 5 doses i.v. in a volume of 100 μL. Bat0606 treatment of NCI-N87 xenografts was discontinued on day 15 and switched to batansine-0606 (5 or 15 mg/kg, i.v.) from the day 21 onwards. Each group consisted of 10 mice. Tumor size was determined at 3 days intervals. 42 days after tumor cell inoculation, animals were upon euthanized and tumors were removed and weighed. As shown in FIG. 29, rapid tumor shrinkage was seen by batansine-0606 (5 or 15 mg/kg) from day 11. From day 32 onwards batansine-0606 (5 or 15 mg/kg) treated tumors had shrunken to non-palpable. Compared to the unconjugated Bat0606, at 5 or 15 mg/kg dose tested, batansine-0606 more significantly inhibited the tumor growth as assessed by tumor weight measurements 35 days after drug treatment.

Example 21

Preparation of Antibody-Drug Conjugates: D-Lmcc-Bat1206

Antibody Bat1206 was diluted to 2.5 mg/mL in solution A (50 mM potassium phosphate, 50 mM NaCl, and 2 mM EDTA, pH 6.5). SMCC-MDC was added to give a ratio of SMCC-MDC to antibody of 7:1 mole equivalent. Then DMA was added to 15% to the reaction and reaction was mixed by stirring for 4 h at ambient temperature. D-Lmcc-Bat1206 conjugate was purified from excess unreacted or hydrolyzed reagent and excess SMCC-MDC using a G25 gel filtration column equilibrated in pH 7.4 phosphate buffer (aqueous). The conjugate was then dialyzed overnight into pH 7.4 phosphate buffer (aqueous) and then filtered through a 0.22 μm filter for final storage. The number of SMCC-MDC molecule per Abu molecule in the final conjugate was measured by determining absorbance of the conjugate at 252 and 280 nm and using known extinction coefficients for SMCC-MDC and antibody at these two wavelengths. A ratio of maytansinoid compound to antibody of 2-5 to 1 was normally obtained.

Example 22

Preparation of Anti-CD20 Antibody Drug Conjugate Batansine-1206

Antibody Bat1206 was diluted to 8.0 mg/mL in solution B (50 mM potassium phosphate, 50 mM NaCl, and 2 mM EDTA, pH 8.0). Partial reduction was carried out with (6 moles equivalent) DTT. After incubation at 37° C. for 60 minutes, the buffer was exchanged by elution through Sephadex G-25 resin with solution B. The thiol-antibody value was determined from the reduced monoclonal antibody (mAb) concentration determined from 280-nm absorbance, and the thiol concentration was determined by reaction with DTNB (5,5'-dithiobis(2-nitrobenzoic acid); Aldrich) and absorbance measured at 412 nm. The conjugation reaction was carried out with 10% DMA. The volume of batansine solution was calculated to contain 1.5-mol batansine (3AA-MDC) per mol equivalent of free thiol on the antibody. Batansine solution was added rapidly with mixing to the cold-reduced antibody solution, and the mixture was stirred at r.t. for 3 hours, and continued for additional 1 h after adding 5 mM cysteine. The reaction mixture was concentrated by centrifugal ultrafiltration and buffer-exchanged by elution through Sephadex G25 equilibrated in PBS. The conjugate was then filtered through a 0.2-μm filter under sterile conditions and stored at −80° C. for analysis and testing. The Batansine-1206 was further analyzed for drug/antibody ratio by measuring unreacted thiols with DTNB, and 3.5:1 ratio of drug/antibody was often obtained. Batansine-1206 was further characterized for concentration by UV absorbance, aggregation by size-exclusion chromatography, and residual free drug by reverse-phase HPLC.

Example 23

Study on the Effect of Bat1206 and D-Lmcc-Bat1206 on the Growth of Raji Cells

Figure 26:
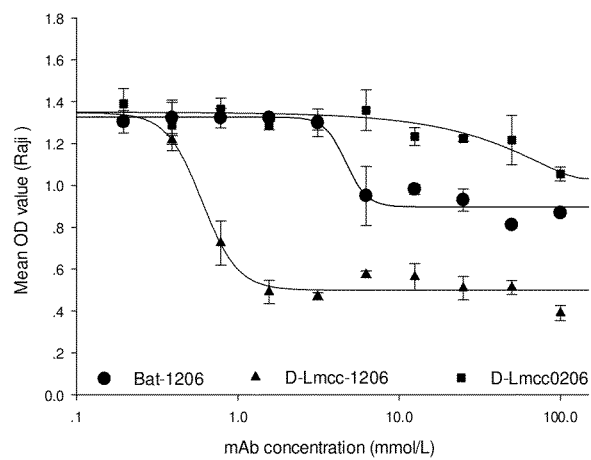
FIG. 26 shows that D-Lmcc-Bat1206 inhibited Raji cell growth.
Figure 27:
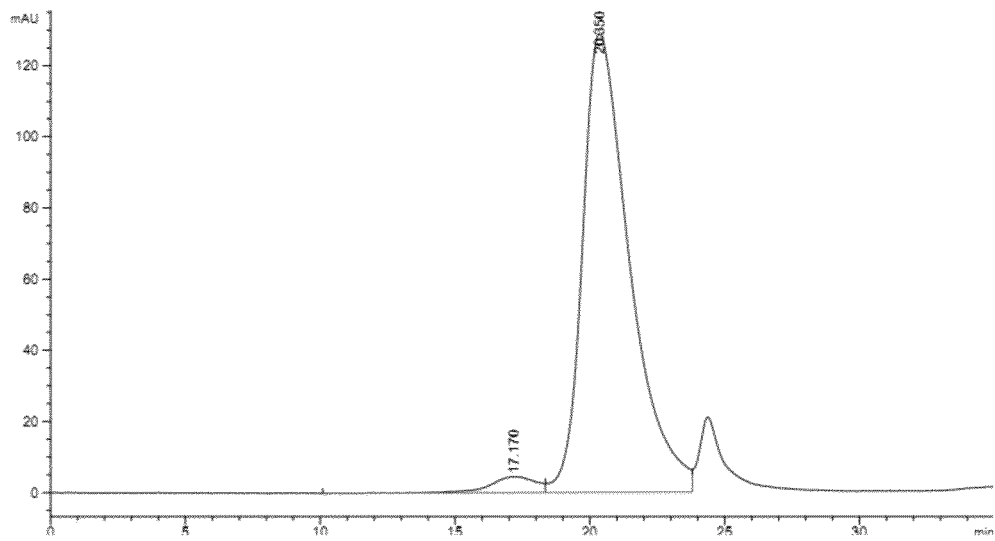
FIG. 27 shows the purification of Batansine-1206 on SEC-HPLC.
Figure 28:
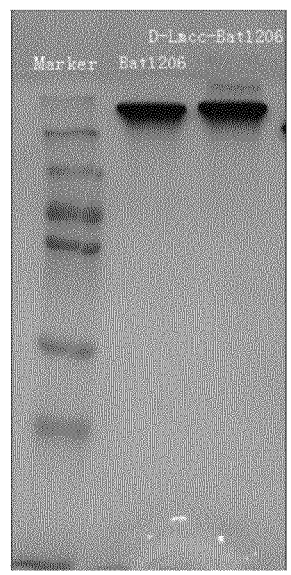
FIG. 28 shows the non-reduced SDS-PAGE of Bat1206 and D-Lmcc-Bat1206.

The effect of Bat1206 and D-Lmcc-Bat1206 on the growth of Raji cell (Shanghai Cell Collection. Ltd., Co. Shanghai, China) was determined using the method described by Ishiyama et al. (Biol. Pharmacol. Bull., 19: 1518-1520, 1996). Briefly, 10 thousands cells in 100 μL of DMEM:F12 (GBICO, CA) culture medium without serum were seeded into each well of a 96-well plate. Twice-fold serial dilutions of antibodies or conjugated form were prepared and each diluted antibodies were added in triplicate to the wells and the cultures were incubated at 37° C. for 3 days. The controls consisted of either medium alone or medium containing of Raji cell. After incubation, CCK-8 was added to each well and the absorbance at 450 nm of each well was determined in a Spectra Max spectrophotometer (Molecular Devices, Sunnyvale, Calif.). As shown in FIG. 26, D-Lmcc-Bat1206 more effectively inhibited CD20 positive cell growth than non conjugated anti-CD20 antibody Bat1206.

Example 24

Cellular Metabolites of Batansine-0206 and D-Lmcc-Bat0206

Cellular metabolites of Batansine-0206 and D-Lmcc-Bat0206 were assayed as described in Erickson, et al. Cancer Res 66:4426-4433 (2006). Briefly, A431 cells ($6\times10^6$) suspended in 3 mL culture medium containing Batansine-0206 at a concentration of $10$-$7$ mol/L of conjugated antibody were incubated at 37° C. for 3 to 30 hours. The cells and the medium were then separated by centrifugation (2,000 g, 5 minutes). The supernatant (3 mL) was chilled on ice, mixed with 4 mL ice-cold acetone, and kept at −80° C. for at least 1 hour or until further processing. Precipitated protein was removed by centrifugation at 2,500 g and the supernatants were acidified with 5% acetic acid and evaporated to dryness. The samples were dissolved in 0.12 mL of 20% aqueous $CH_3CN$ containing 0.025% trifluoroacetic acid (TFA), aliquots of 0.1 mL were submitted to LC-MS. The metabolite of Batansine-0206: LC-MS $(M+H^+)$ calc.: 964.5. found: 964.2. The metabolite of D-Lmcc-Bat0206: LC-MS $(M+H^+)$ calc.: 1103.7. found: 1103.3.

What is claimed is:

1. A compound of Formula I or I-1:

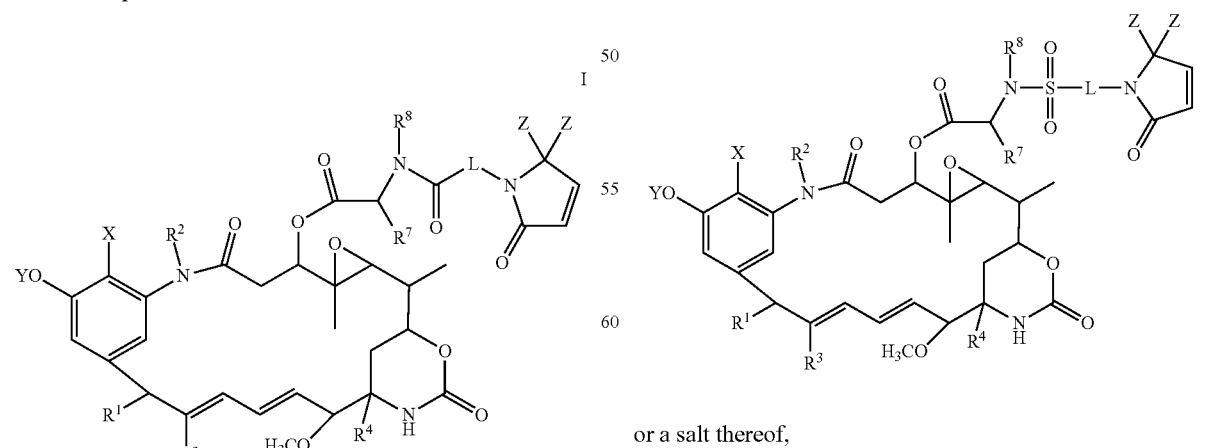

or a salt thereof,
wherein
X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —$CH_2OH$, or —$CH_2C$(=O)$R^6$;

$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_1$-$C_6$ alkyl;

each Z is independently hydrogen or $C_1$-$C_4$ alkyl, or the two Z with the carbon atom to which they are attached form a C=O; and in Formula I, L is selected from substituted $C_1$-$C_{20}$ alkylene, $C_3$-$C_8$ cycloalkylene substituted $C_1$-$C_{20}$ alkylene wherein one or more of the —$CH_2$— groups are independently replaced with $C_3$-$C_8$ cycloalkylene, —S—, —$NR^8C$(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CONR$^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

in Formula I-1, L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8C$(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo.

2. The compound of claim 1, which is:

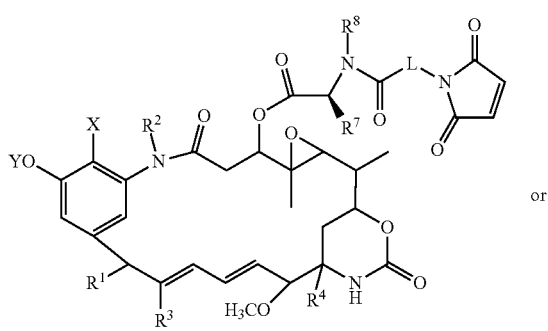

or

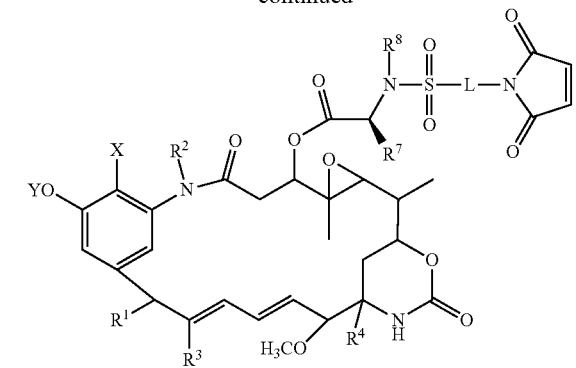

or a salt thereof.

3. The compound of claim 1, which is a compound of Formula III or III-1:

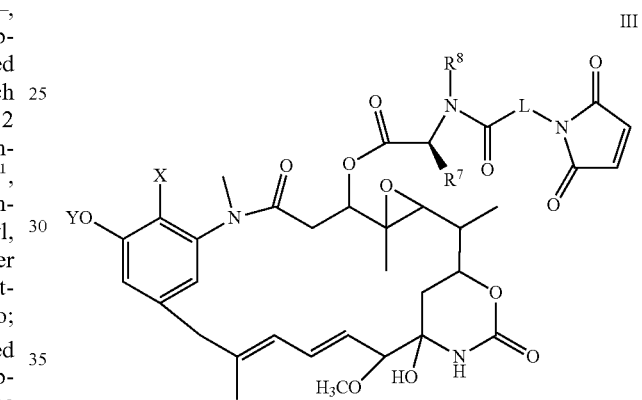

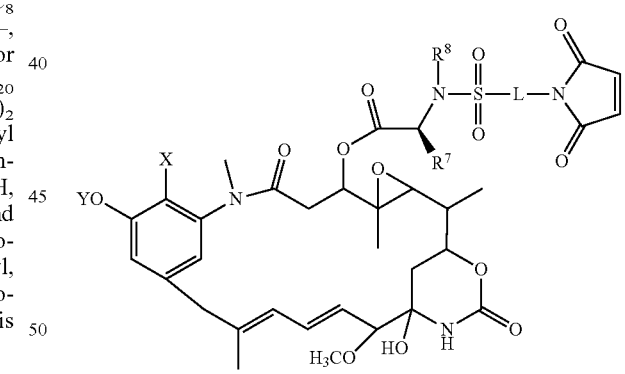

or a salt thereof,
wherein
X is H or Cl;
Y is H or methyl;
$R^7$ is hydrogen, $C_1$-$C_6$ alkyl or an amino acid side chain;
$R^8$ is hydrogen or $C_1$-$C_6$ alkyl; and
in Formula III, L is selected from substituted $C_1$-$C_{20}$ alkylene, $C_3$-$C_8$ cycloalkylene substituted $C_1$-$C_{20}$ alkylene wherein one or more of the —$CH_2$— groups are independently replaced with $C_3$-$C_8$ cycloalkylene, —S—, —$NR^8C$(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each R$^{11}$ is independently hydrogen, alkyl, aryl, cycloalkyl, cycloalkenyl, heteroaryl, and heterocyclic, or the two R$^{11}$ together with the nitrogen form a heterocyclic, wherein the heterocyclic is optionally substituted with one or two oxo;

in Formula III-1, L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —NR$^8$—, —C(O)—, —C(=O)NR$^8$—, —NR$^8$C(=O)—, —SO$_2$NR$^8$—, or —NR$^8$SO$_2$—; substituted $C_1$-$C_{20}$ alkylene is $C_1$-$C_{20}$ alkylene substituted with 1 to 4 —SO$_3$H, —P(O)(OH)$_2$ or R$^{23}$, wherein each R$^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each R$^{11}$ is independently hydrogen, alkyl, aryl, cycloalkyl, cycloalkenyl, heteroaryl, and heterocyclic, or the two R$^{11}$ together with the nitrogen form a heterocyclic, wherein the heterocyclic is optionally substituted with one or two oxo.

4. The compound of claim 1, which is a compound of Formula IV-1:

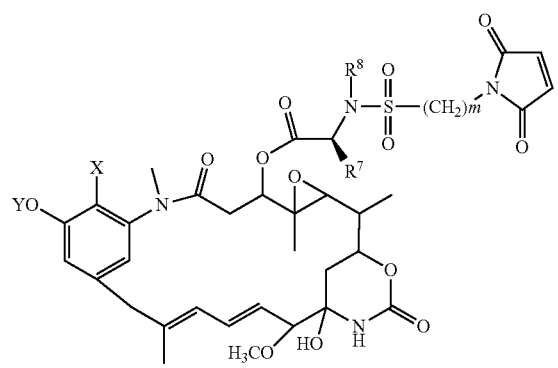

or a salt thereof,
wherein
X is H or Cl;
Y is H or methyl;
R$^7$ is hydrogen, $C_1$-$C_6$ alkyl or an amino acid side chain;
R$^8$ is hydrogen or $C_1$-$C_6$ alkyl; and
m is an integer of 1 to 20.

5. The compound of claim 1, selected from the group consisting of

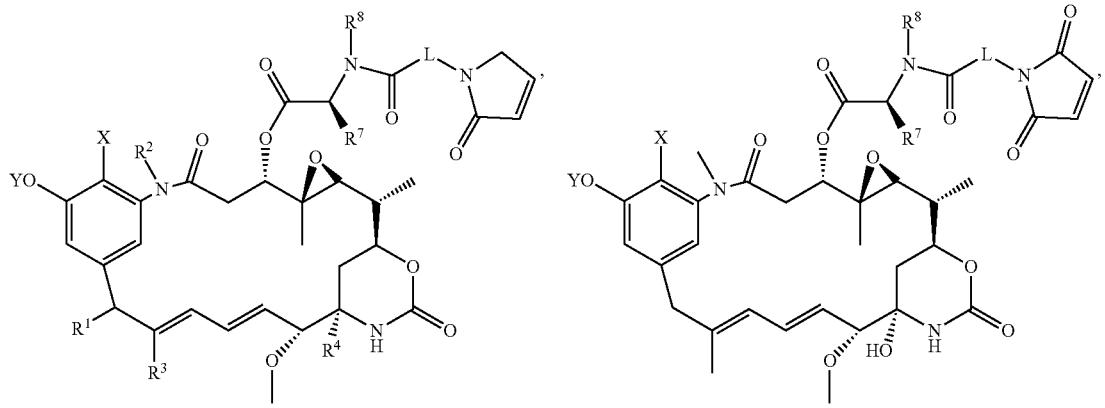

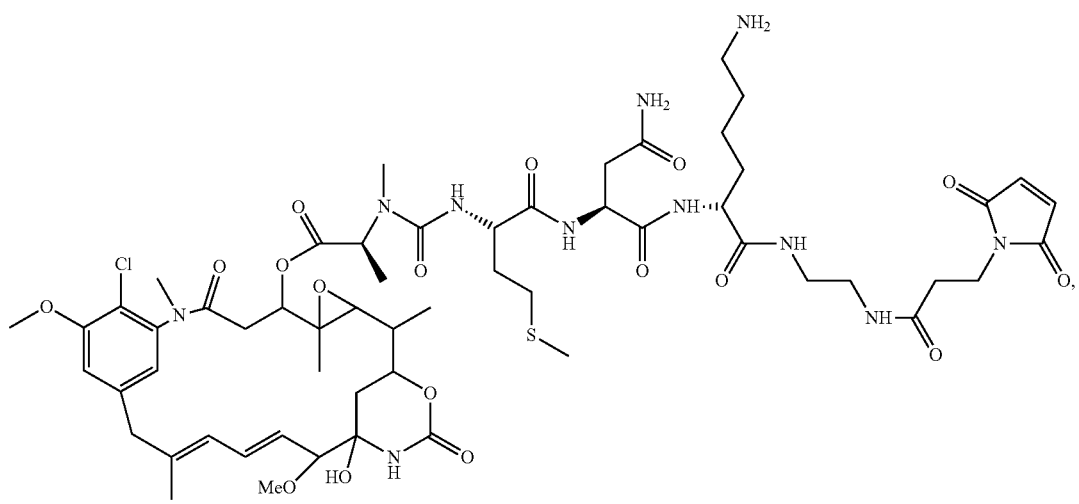

-continued
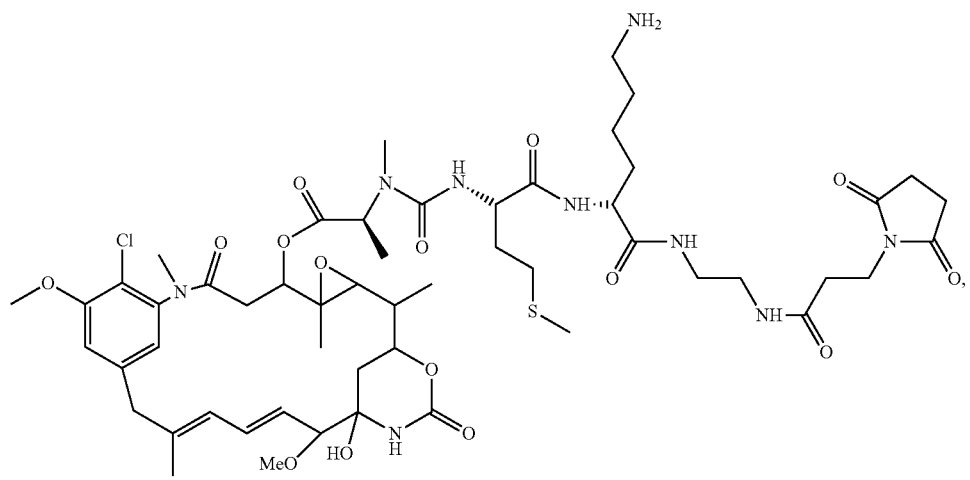
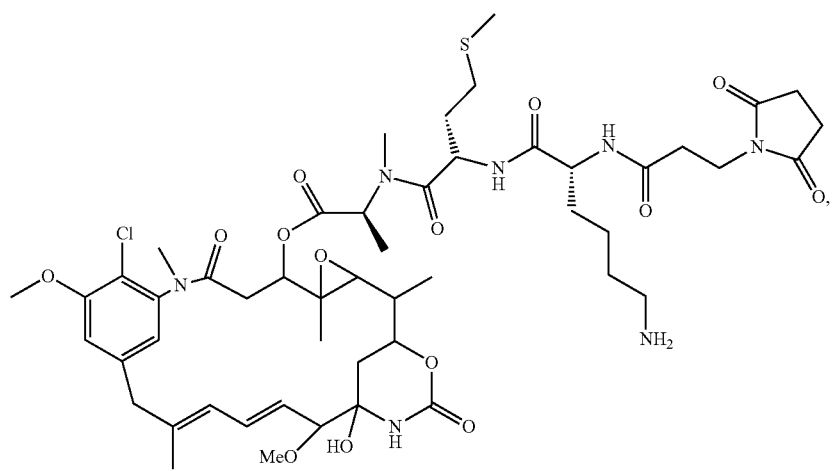
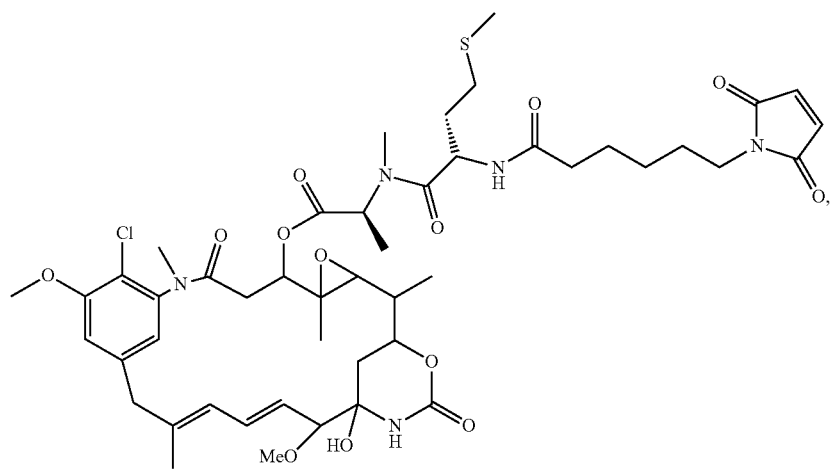

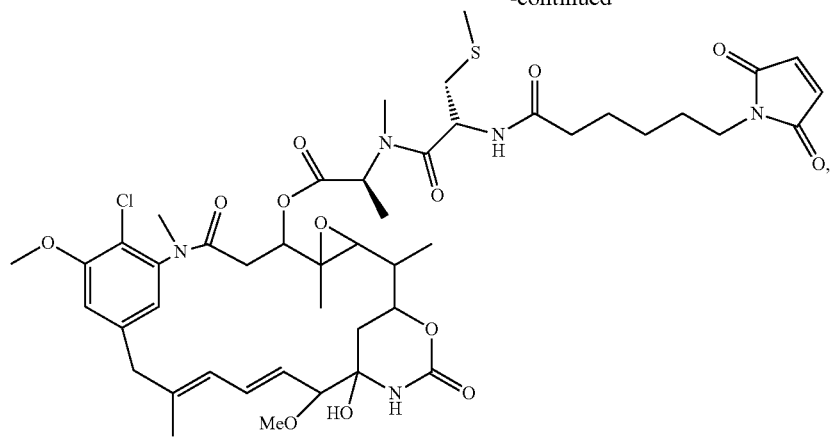
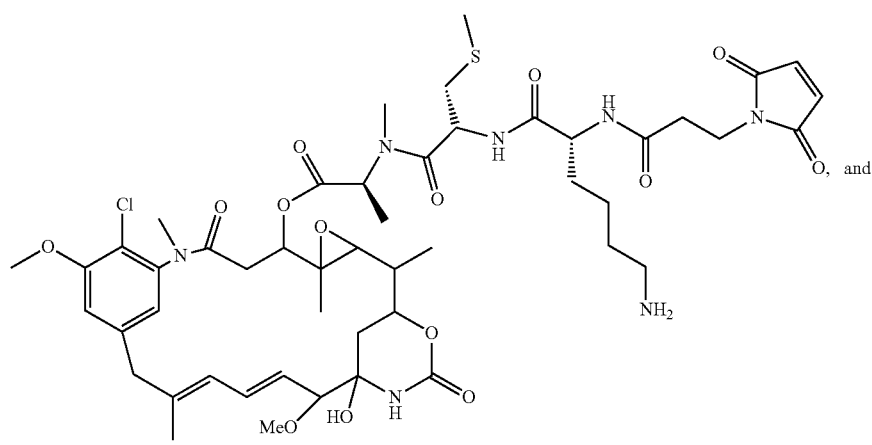
, and
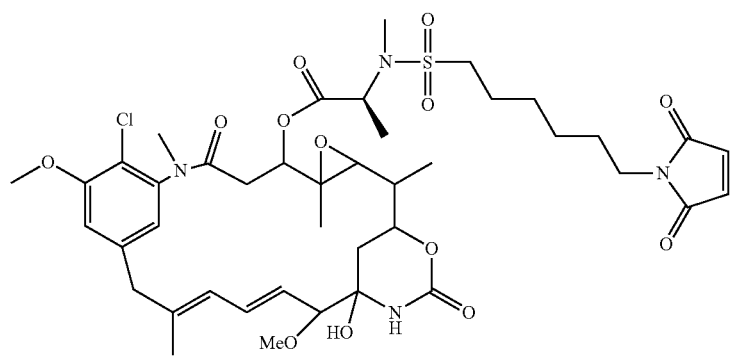
or a salt thereof.

6. The compound of claim 1, selected from the group consisting of
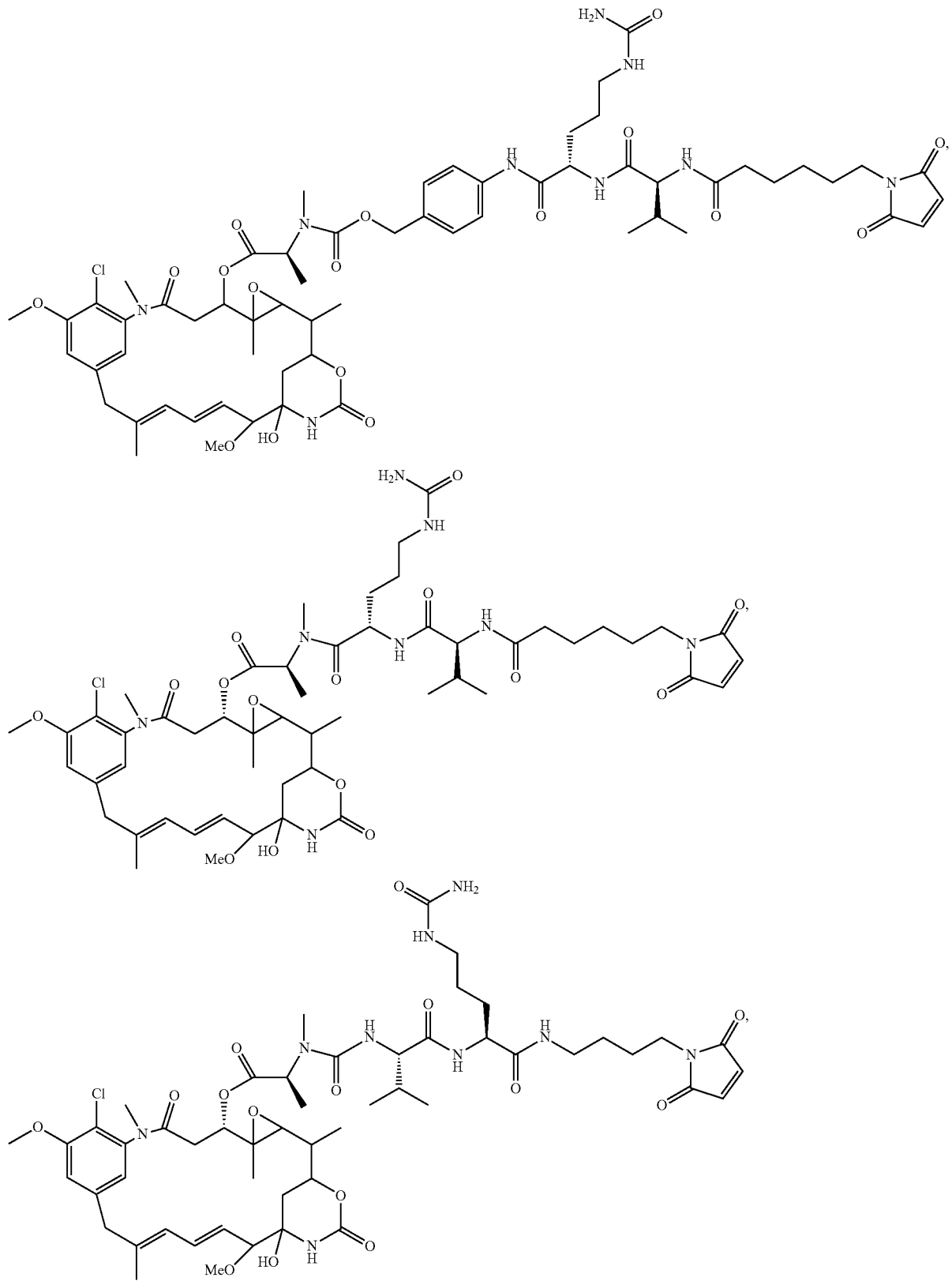

-continued
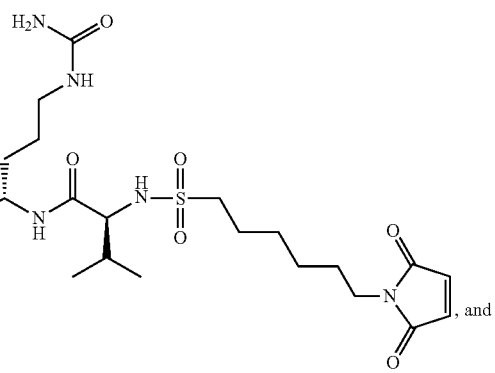
, and
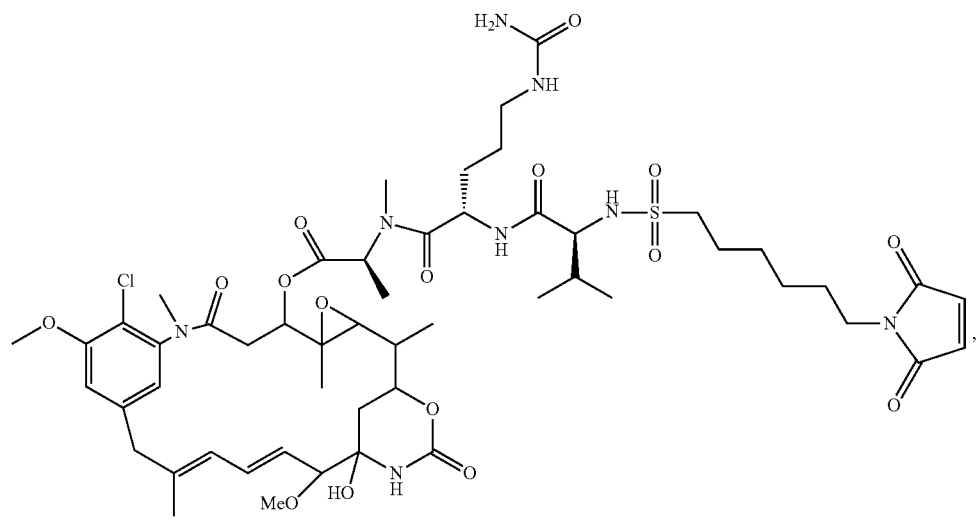
,
or a salt thereof.
7. The compound of claim 1, which is a compound of Formula V-1:
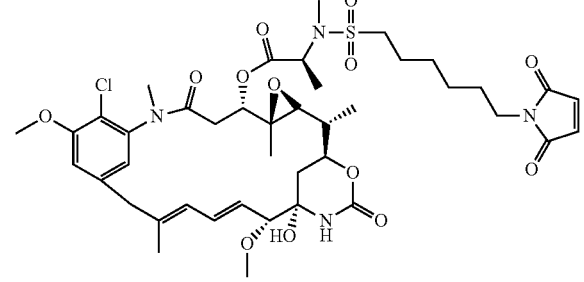
or a salt thereof.
8. A compound of Formula II or II-1:
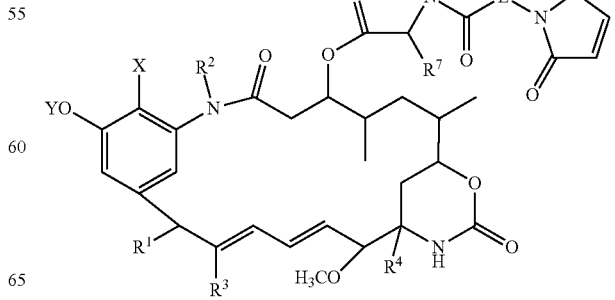

-continued

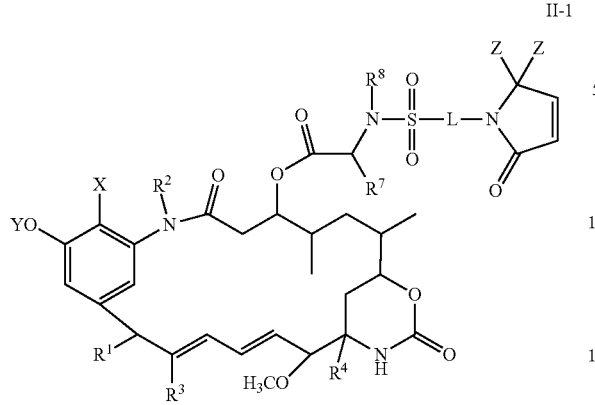

II-1 or a salt thereof, wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —CH$_2$OH, or —CH$_2$C(=O)$R^6$;

$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_{1-6}$ alkyl;

each Z is independently hydrogen or $C_1$-$C_4$ alkyl, or the two Z with the carbon atom to which they are attached form a C=O; and L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— group is independently replaced with $C_3$-$C_8$ cycloalkylene, —O—, —S—, —N$R^8$—, —C(O)—, —C(=O)N$R^8$—, —N$R^8$C(=O)—, —SO$_2$N$R^8$—, or —N$R^8$SO$_2$—;

substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CON$R^{11}R^{11}$, —CO$_2$H, and —N$R^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo.

9. The compound of claim 8, which is:

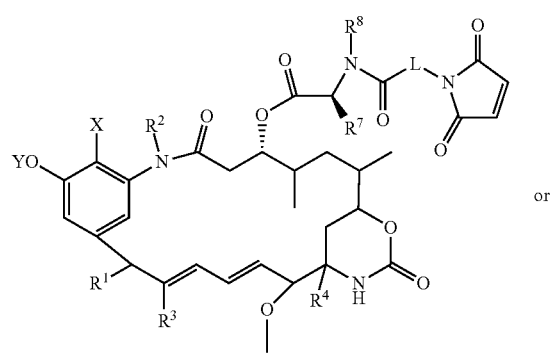

or

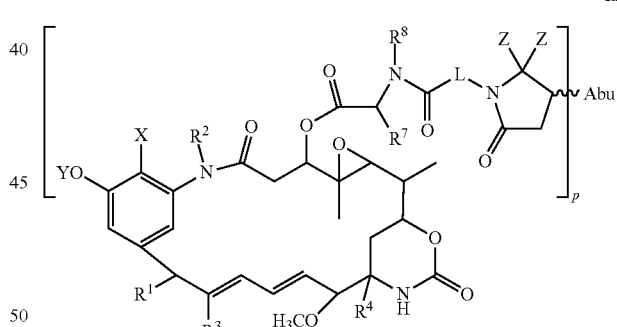

or a salt thereof.

10. A compound of Formula Ia or Ia-1:

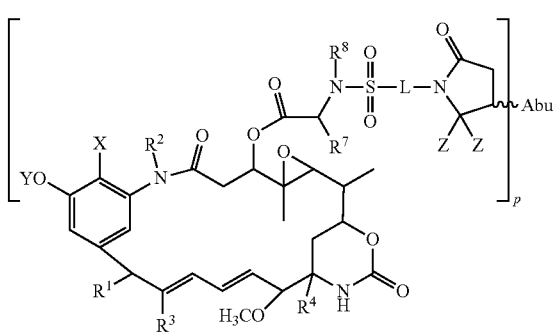

or a pharmaceutically acceptable salt or solvate thereof, wherein
- X is hydrogen or halo;
- Y is selected from the group consisting of hydrogen, $C_1$-$C_6$ alkyl, $C_3$-$C_6$ cycloalkyl, and —C(=O)$R^5$;
- $R^1$ is selected from the group consisting of hydrogen, —OH, —OC(=O)$R^5$ and —O$R^5$;
- $R^2$ is hydrogen or $C_1$-$C_6$ alkyl;
- $R^3$ is methyl, —CH$_2$OH, or —CH$_2$C(=O)$R^6$;
- $R^4$ is —OH or —SH;
- $R^5$ is $C_1$-$C_6$ alkyl or benzyl;
- $R^6$ is $C_1$-$C_6$ alkyl, phenyl or benzyl;
- $R^7$ is hydrogen, $C_1$-$C_6$ alkyl or an amino acid side chain;
- $R^8$ is hydrogen or $C_{1-6}$ alkyl;
- each Z is independently hydrogen or $C_1$-$C_4$ alkyl, or the two Z with the carbon atom to which they are attached form a C=O;
- p is selected from 1, 2, 3, 4, 5, 6, 7, 8, 9, and 10;
- in Formula Ia, L is selected from substituted $C_1$-$C_{20}$ alkylene, $C_3$-$C_8$ cycloalkylene, substituted $C_1$-$C_{20}$ alkylene wherein one or more of the —CH$_2$— groups are independently replaced with $C_3$-$C_8$ cycloalkylene, —S—, —NR$^8$C(=O)—, —SO$_2$NR$^8$—, or —NR$^8$SO$_2$—; substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;
- in Formula Ia-1, L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —NR$^8$—, —C(O)—, —C(=O)NR$^8$—, —NR$^8$C(=O)—, —SO$_2$NR$^8$—, or —NR$^8$SO$_2$—; substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and
- Abu is an antigen binding unit.

11. The compound of claim 10 which is:

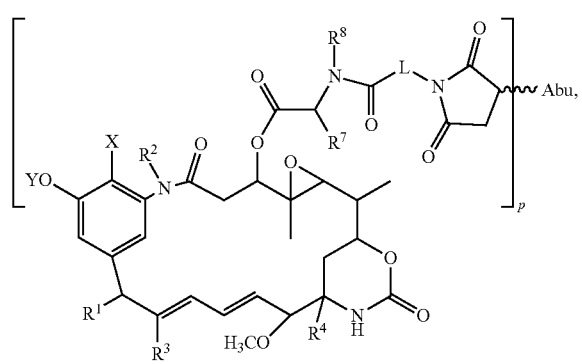

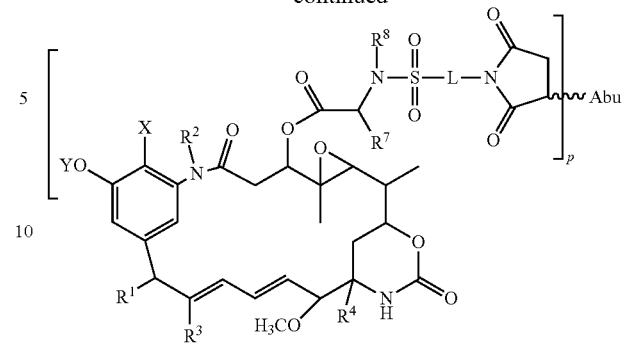

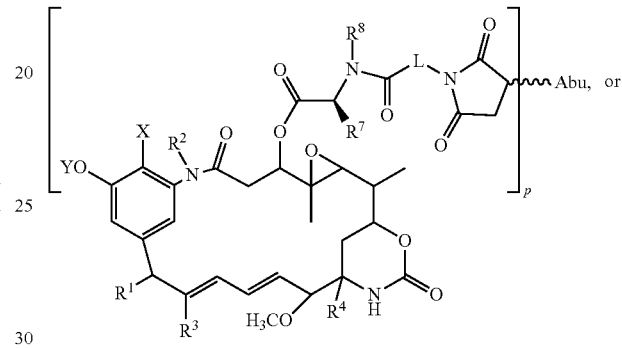

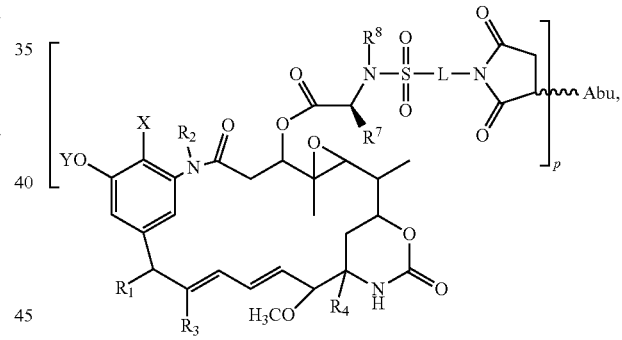

or a salt thereof.

12. The compound of claim 10, which is of Formula IIIa or IIIa-1:

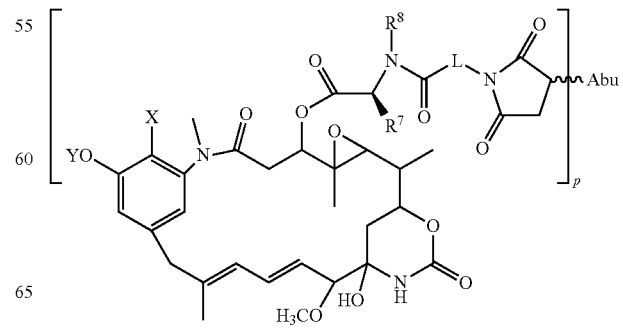

-continued

IIIa-1

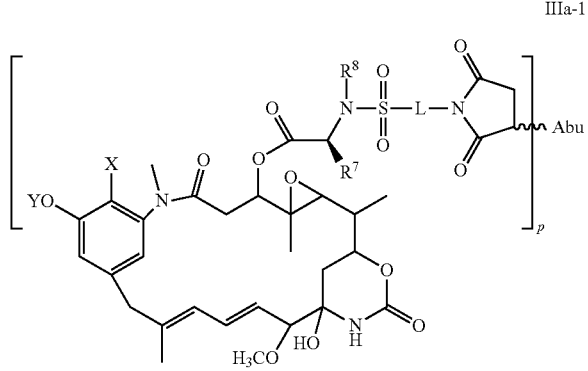

or a pharmaceutically acceptable salt or solvate thereof, wherein

X is H or Cl;
Y is H or methyl;
$R^7$ is hydrogen, $C_1$-$C_6$ alkyl or an amino acid side chain;
$R^8$ is hydrogen or $C_1$-$C_6$ alkyl;
p is selected from 1, 2, 3, 4, 5, 6, 7, 8, 9, and 10;
in Formula IIIa, L is selected from substituted $C_1$-$C_{20}$ alkylene, $C_3$-$C_8$ cycloalkylene, substituted $C_1$-$C_{20}$ alkylene wherein one or more of the —$CH_2$— groups are independently replaced with $C_3$-$C_8$ cycloalkylene, —S—, —$NR^8C(=O)$—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —$P(O)(OH)_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and
in Formula IIIa-1, L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —$C(=O)NR^8$—, —$NR^8C(=O)$—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —$P(O)(OH)_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and Abu is an antigen binding unit.

13. The compound of claim 10, which is of Formula IVa-1:

IVa-1

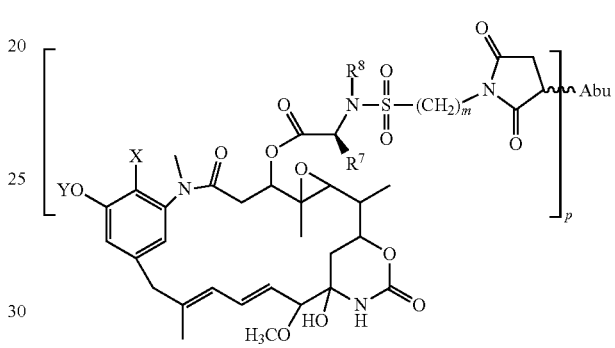

or a pharmaceutically acceptable salt or solvate thereof, wherein

X is H or Cl;
Y is H or methyl;
$R^7$ is hydrogen, $C_1$-$C_6$ alkyl or an amino acid side chain;
$R^8$ is hydrogen or $C_1$-$C_6$ alkyl;
p is selected from 1, 2, 3, 4, 5, 6, 7, 8, 9, and 10;
m is selected from an integer of 1 to 20; and
Abu is an antigen binding unit.

14. The compound of claim 10, selected from the group consisting of

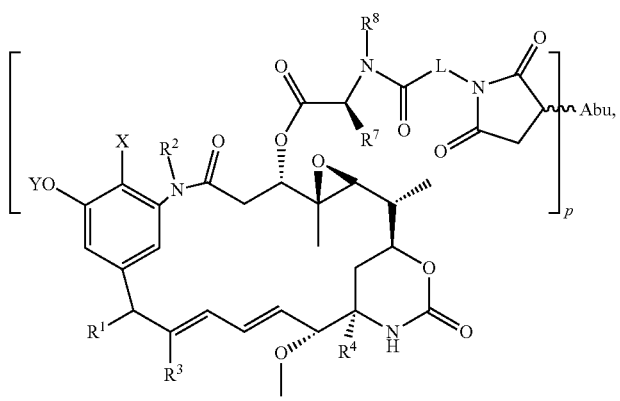

-continued
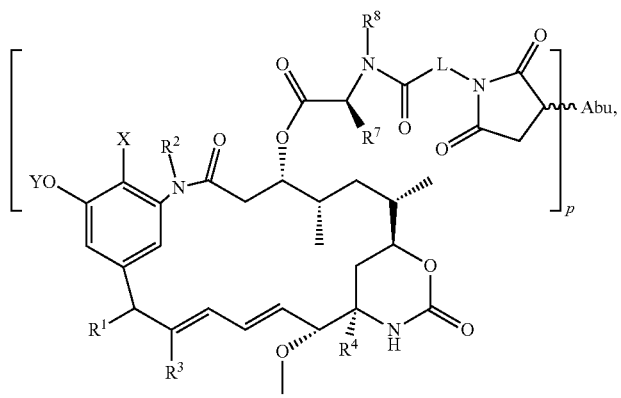
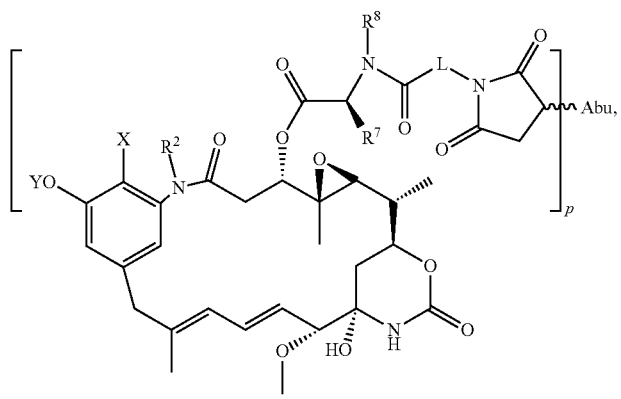
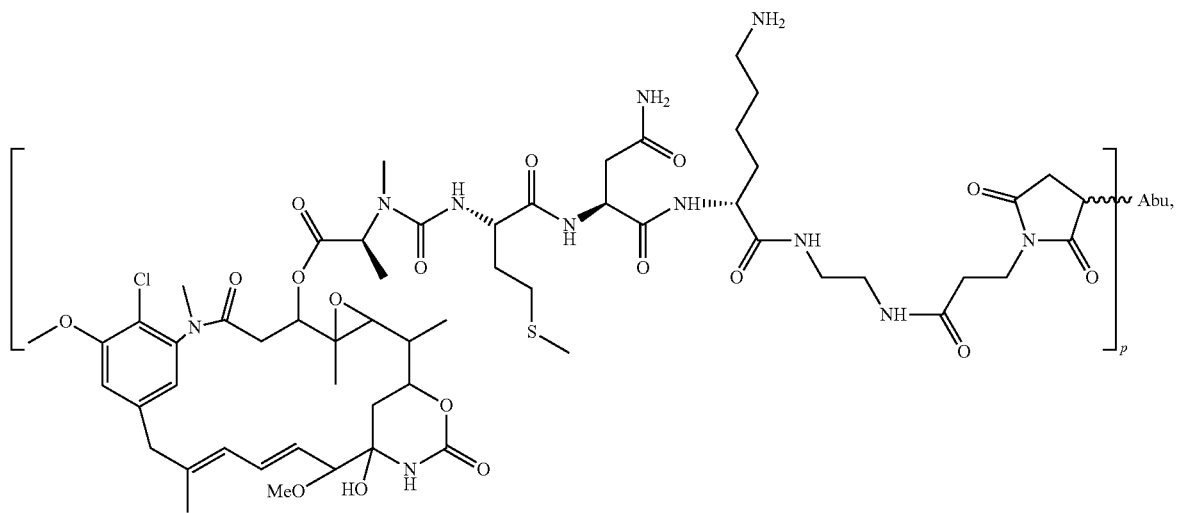

-continued
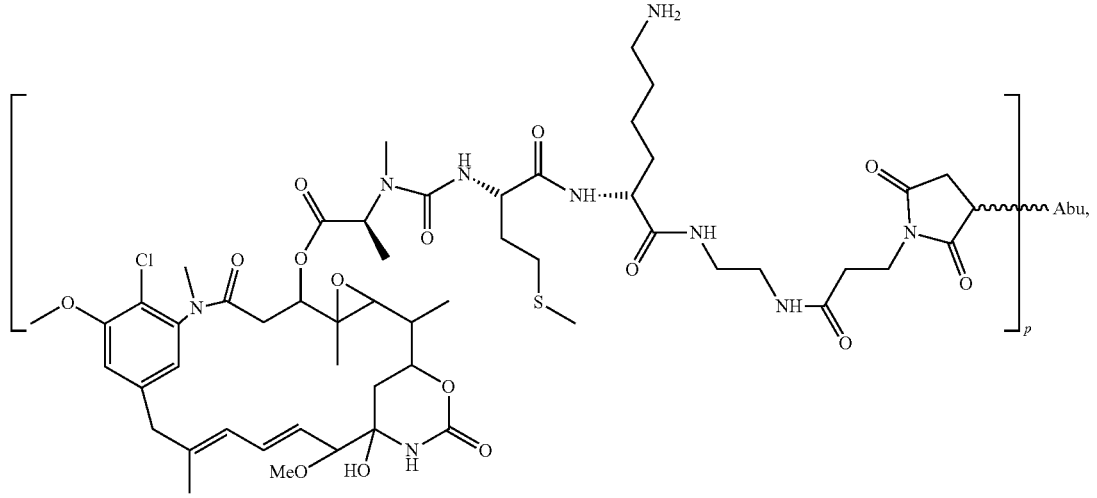
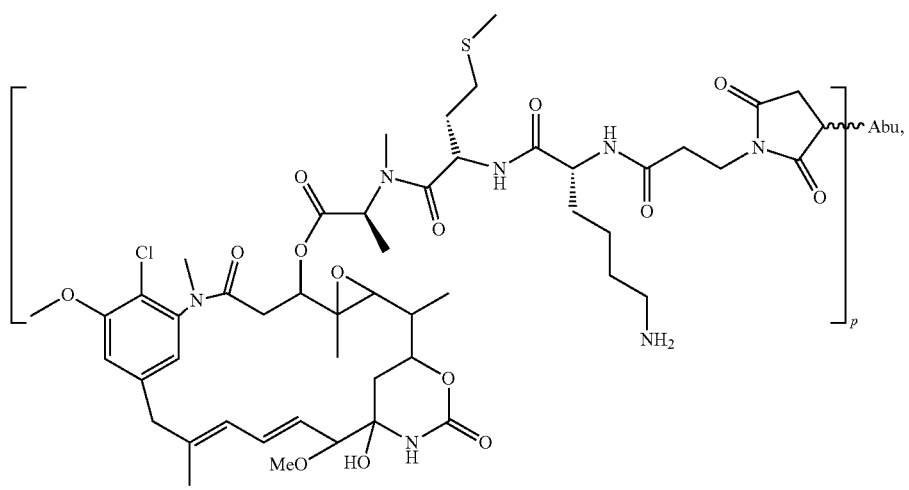
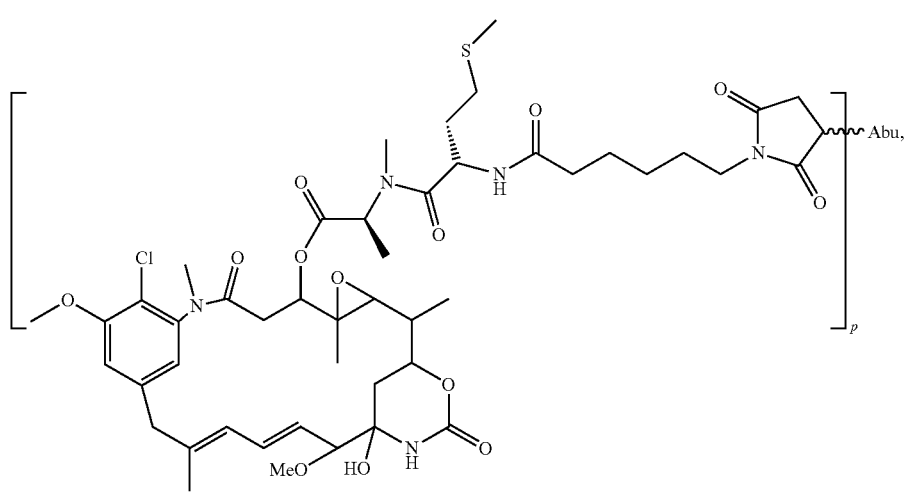

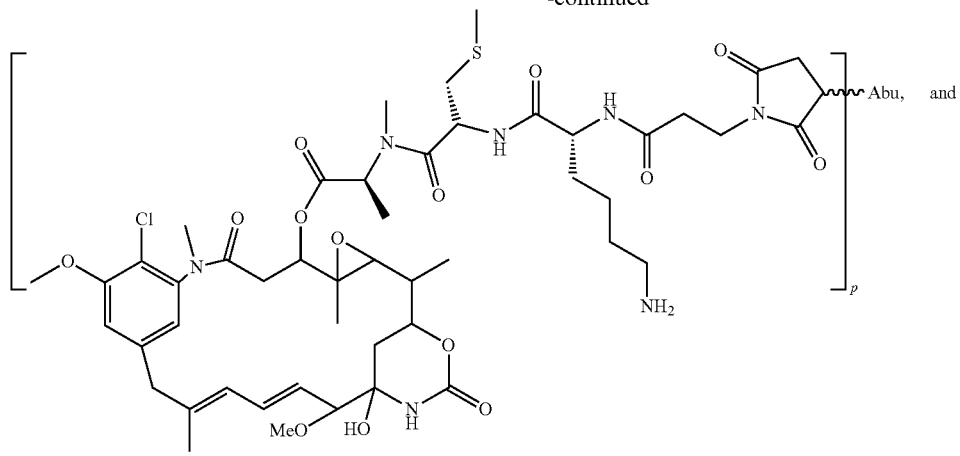
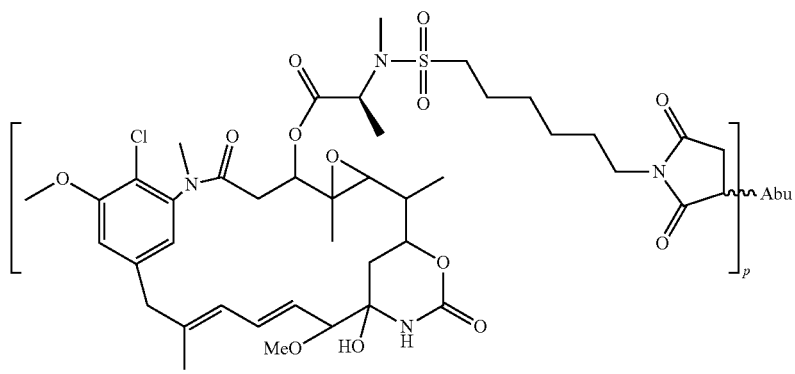
or a pharmaceutically acceptable salt thereof.
15. The compound of claim 10, selected from the group consisting of
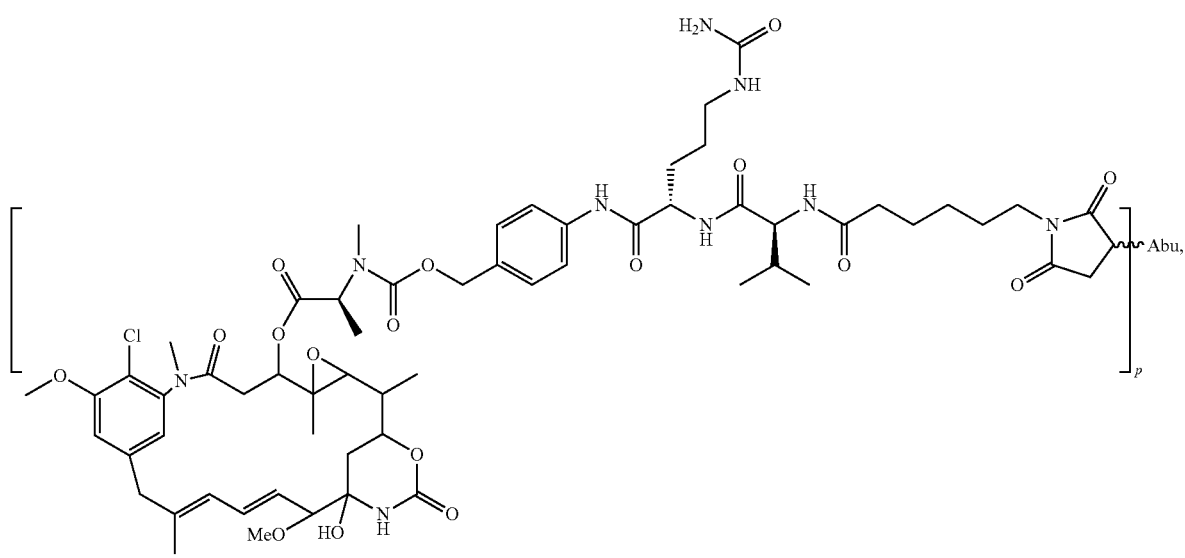
XVa XVIa
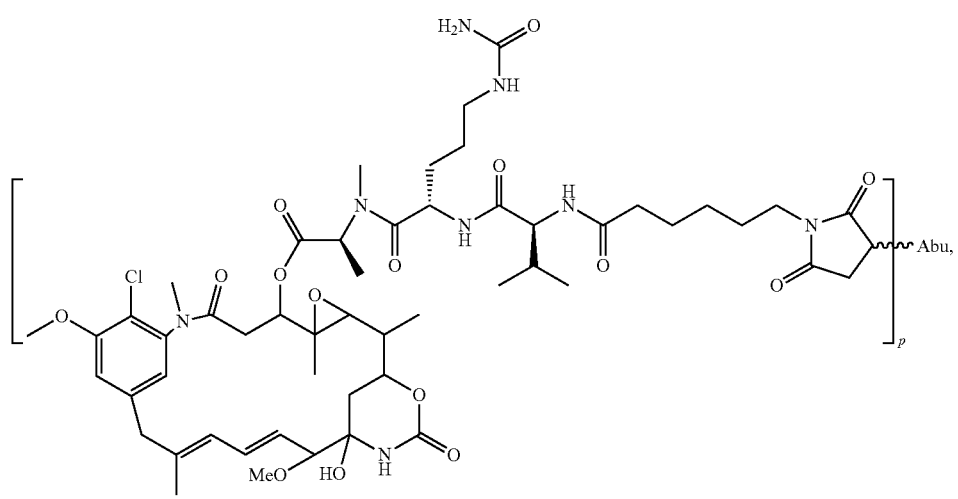
XVIIa
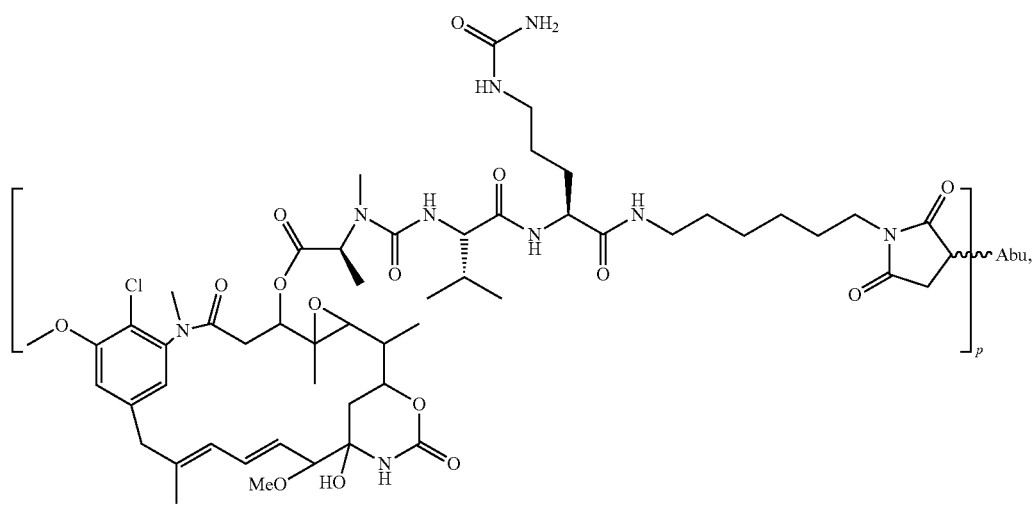
XVIIIa
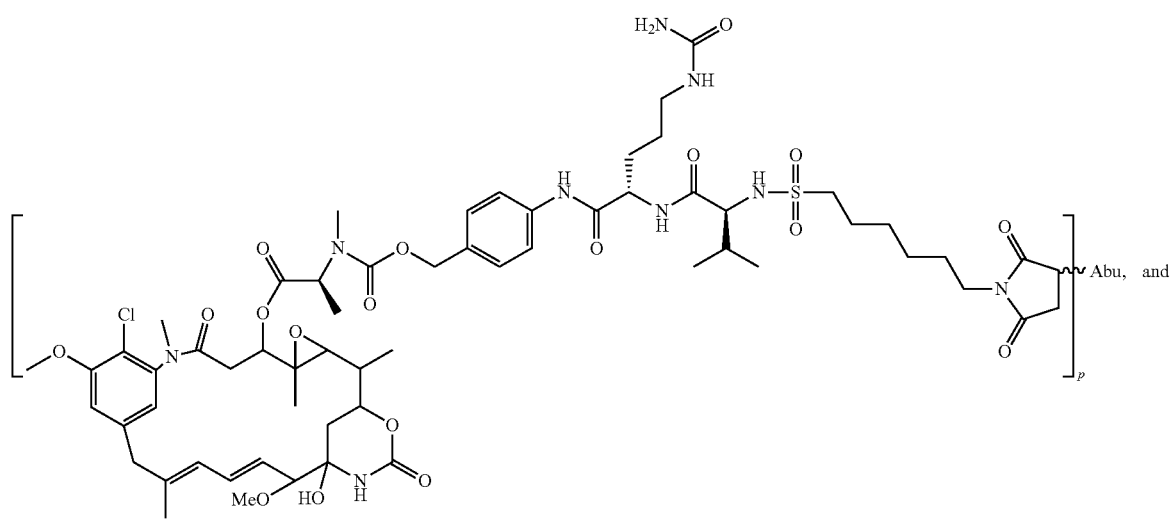

-continued

XIXa

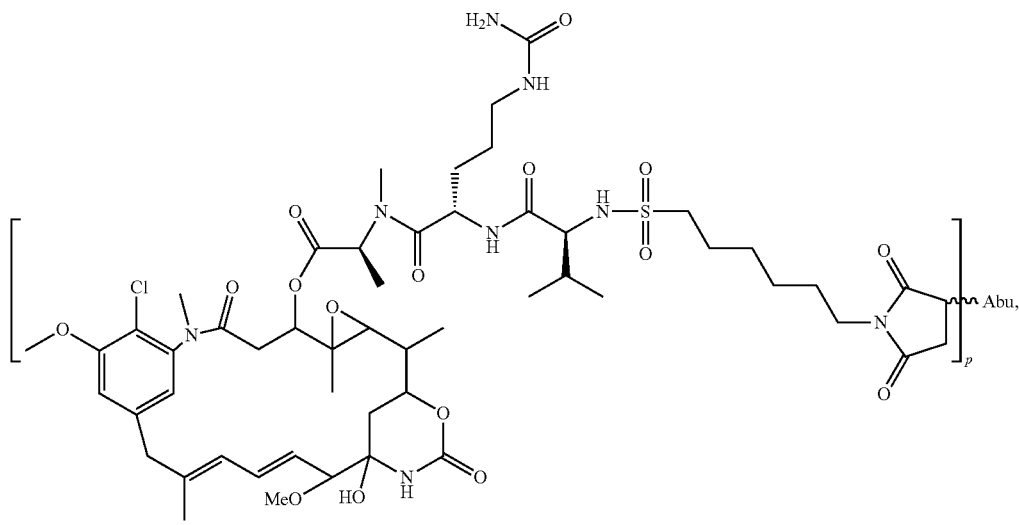

or a pharmaceutically acceptable salt thereof.

16. A compound of Formula IIa or IIa-1:

IIa

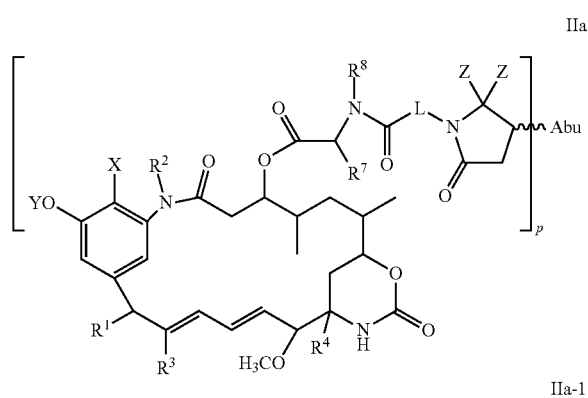

IIa-1

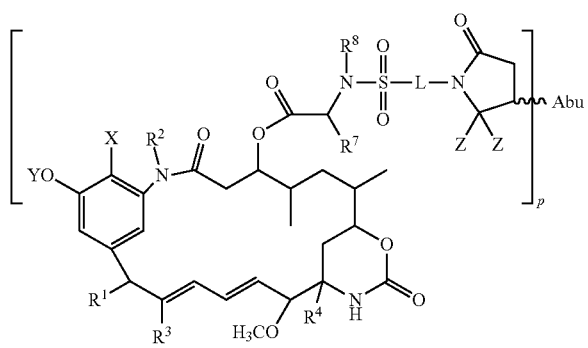

or a pharmaceutically acceptable salt or solvate thereof, wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —CH$_2$OH, or —CH$_2$C(=O)$R^6$;

$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_{1-6}$ alkyl;

p is selected from 1, 2, 3, 4, 5, 6, 7, 8, 9, and 10;

each Z is independently hydrogen or $C_1$-$C_4$ alkyl, or the two Z with the carbon atom to which they are attached form a C=O;

in Formula IIa, L is selected from substituted $C_1$-$C_{20}$ alkylene, $C_3$-$C_8$ cycloalkylene, substituted $C_1$-$C_{20}$ alkylene wherein one or more of the —CH$_2$— groups are independently replaced with $C_3$-$C_8$ cycloalkylene, —S—, —NR$^8$C(=O)—, —SO$_2$NR$^8$—, or —NR$^8$SO$_2$—; substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

in Formula IIa-1, L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —NR$^8$—, —C(O)—, —C(=O)NR$^8$—, —NR$^8$C(=O)—, —SO$_2$NR$^8$—, or —NR$^8$SO$_2$—; substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and Abu is an antigen binding unit.

17. The compound of claim 16, which is:

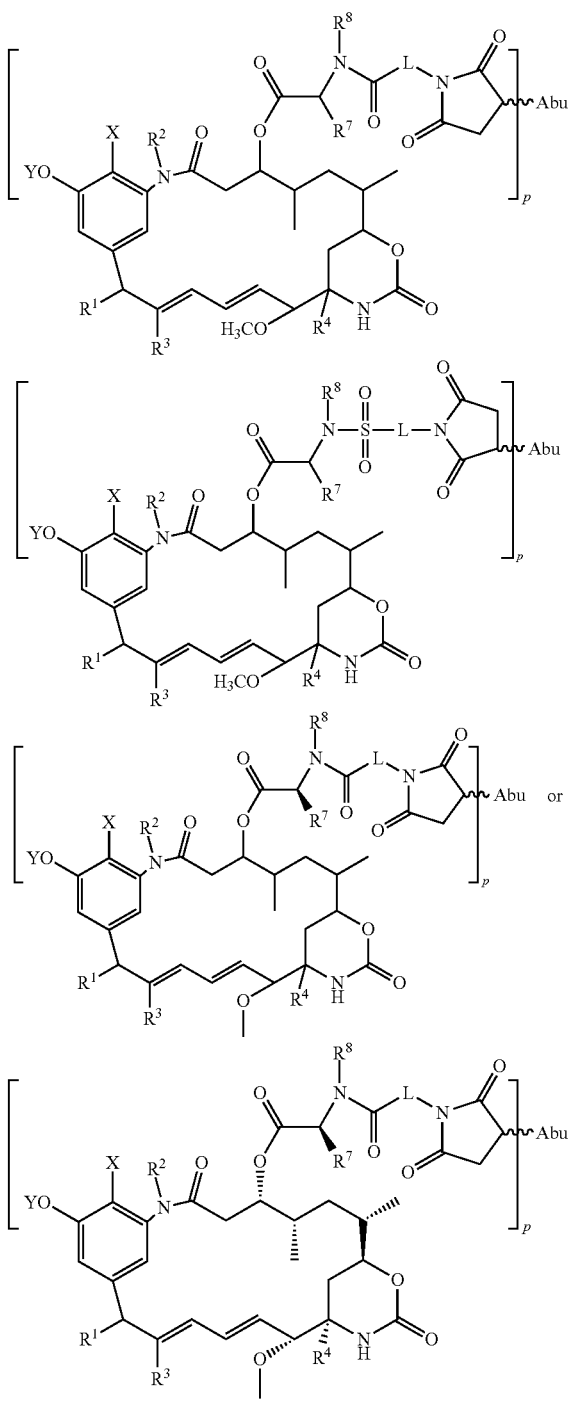

or a pharmaceutically acceptable salt or solvate thereof.

18. The compound of claim 10, wherein Abu is an antigen binding unit with binding specificity to human EGFR.

19. The compound of claim 10, wherein Abu is an antigen binding unit with binding specificity to human CD20.

20. The compound of claim 10, wherein Abu is an antigen binding unit with binding specificity to human Her2.

21. The compound of claim 18, wherein Abu is an antibody, antibody fragment, or cell specific ligands.

22. The compound of claim 10, wherein Abu is an antibody comprising SEQ ID 1 and 2, or SEQ ID 3 and 4, or SEQ ID 5 and 6, or SEQ ID 7 and 8, or SEQ ID 9 and 10, SEQ ID 11 and 12, or SEQ ID 13 and 14.

23. The compound of claim 10, wherein Abu is an antibody comprising Bat0202 (SEQ ID NO: 1) and/or Bat0204 (SEQ ID NO: 2).

24. The compound of claim 10, wherein Abu is Bat0206.

25. The compound of claim 10, wherein Abu is selected from C225, EGF-ABX, EGF-ABX, NIMO, Matu, rituxamab, Cetuximab, trastuzumab and Pertuzumab.

26. A drug-linker-antigen binding unit conjugate wherein the drug is a maytansinoid and the antigen binding unit is Bat0206.

27. A compound of Formula Id or IId:

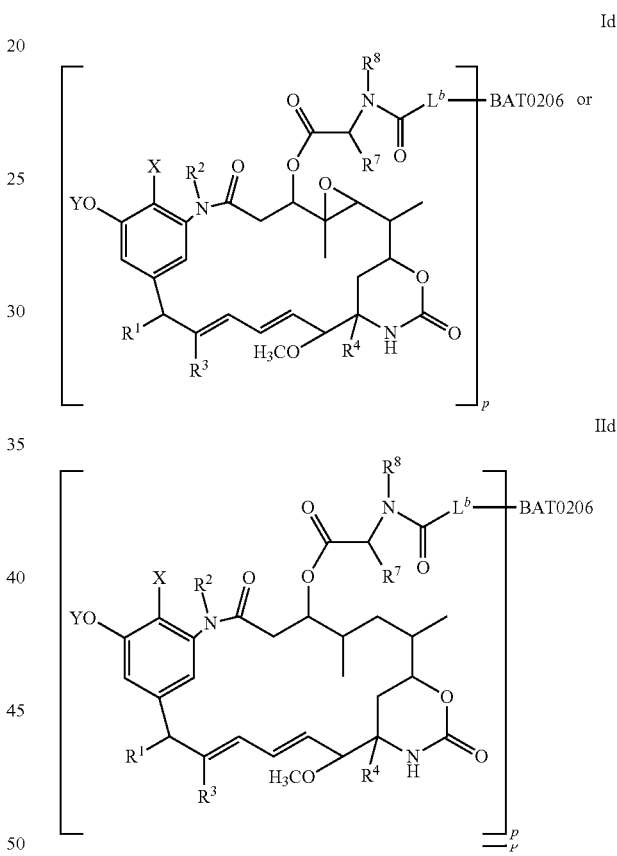

or a pharmaceutically acceptable salt or solvate thereof, wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —CH$_2$OH, or —CH$_2$C(=O)$R^6$;

$R^4$ is —OH or —SH; and $R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;
$R^8$ is hydrogen or $C_{1-6}$ alkyl;
p is selected from 1, 2, 3, 4, 5, 6, 7, 8, 9, and 10; and
in Formula Id, $L^b$ is selected from $C_1$-$C_{20}$ alkylene optionally substituted with $C_1$-$C_4$ alkyl, —$SO_3H$ or —$P(O)(OH)_2$, $C_3$-$C_8$ cycloalkylene optionally substituted with $C_1$-$C_4$ alkyl, and $C_1$-$C_{20}$ alkylene which is optionally substituted with $C_1$-$C_4$ alkyl, —$SO_3H$ or —$P(O)(OH)_2$ and wherein one or more of the —$CH_2$— groups are independently replaced with $C_3$-$C_8$ cycloalkylene, —S—, —S—S—, —$SO_2NR^8$—, or —$NR^6SO_2$;

in Formula IId, $L^b$ is selected from $C_1$-$C_{20}$ alkylene optionally substituted with $C_1$-$C_4$ alkyl, —$SO_3H$ or —$P(O)(OH)_2$, $C_3$-$C_8$ cycloalkylene optionally substituted with $C_1$-$C_4$ alkyl, and $C_1$-$C_{20}$ alkylene which is optionally substituted with $C_1$-$C_4$ alkyl, —$SO_3H$ or —$P(O)(OH)_2$ and wherein one or more of the —$CH_2$— groups are independently replaced with $C_3$-$C_8$ cycloalkylene, 3-8 membered heterocycloalkylene optionally substituted with one or more $C_1$-$C_4$ alkyl or oxo, —O—, —S—, —S—S—, —$NR^8$—, —C(=O)$NR^8$—, —$NR^8C(=O)$—, —$SO_2NR^8$—, or —$NR^8SO_2$;

BAT0206 is an Anti-EGFR antibody.

28. The compound of claim 27, wherein, in Formula Id, $L^b$ is $C_1$-$C_{20}$ alkylene which is substituted with $C_1$-$C_4$ alkyl, —$SO_3H$ or —$P(O)(OH)_2$ and wherein one or more of the —$CH_2$— groups are independently replaced with —S—, —S—S—,

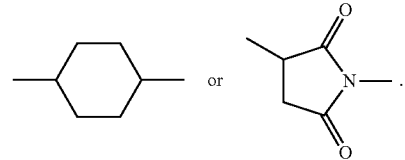

29. The compound of claim 27, selected from the group consisting of

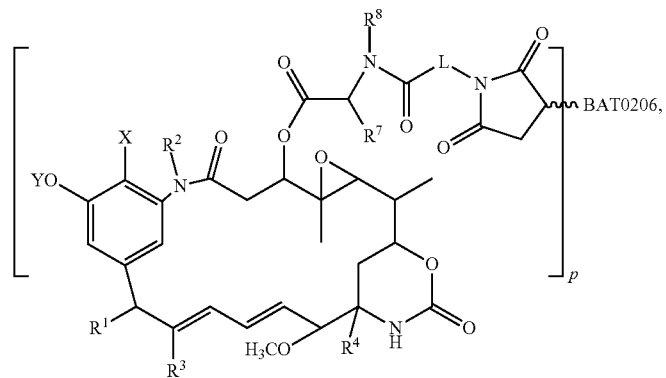

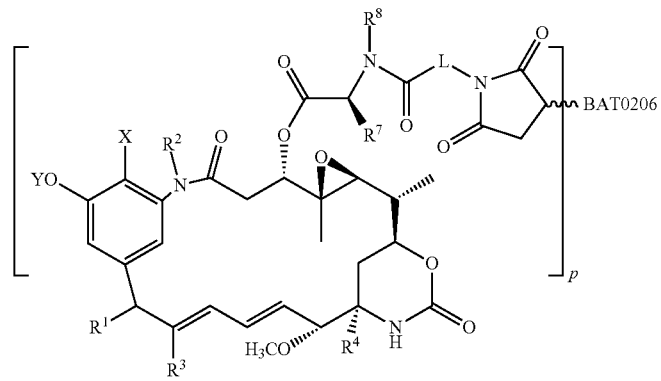

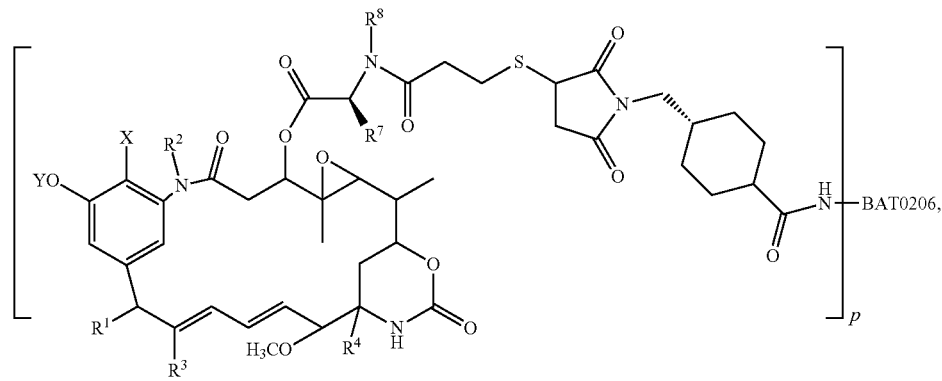

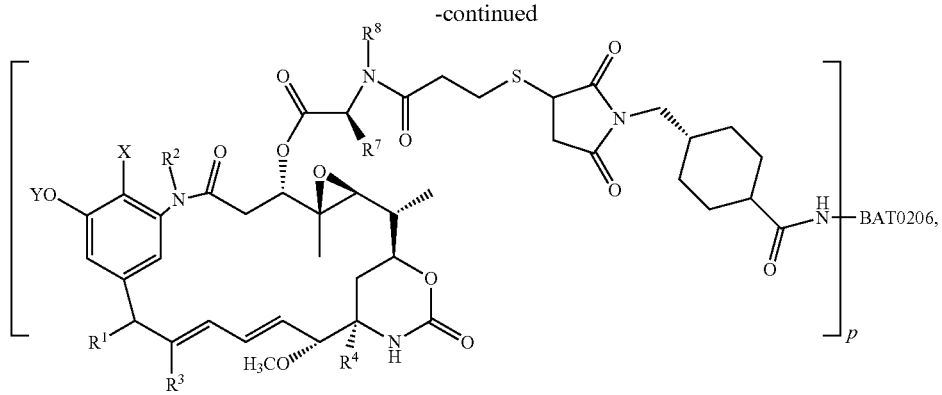

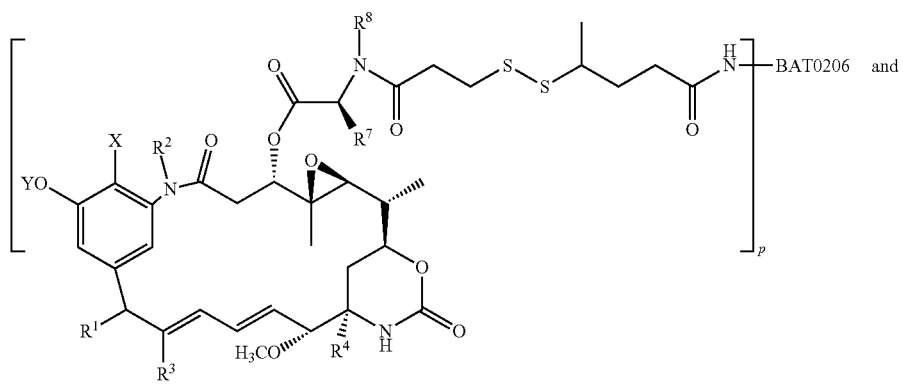

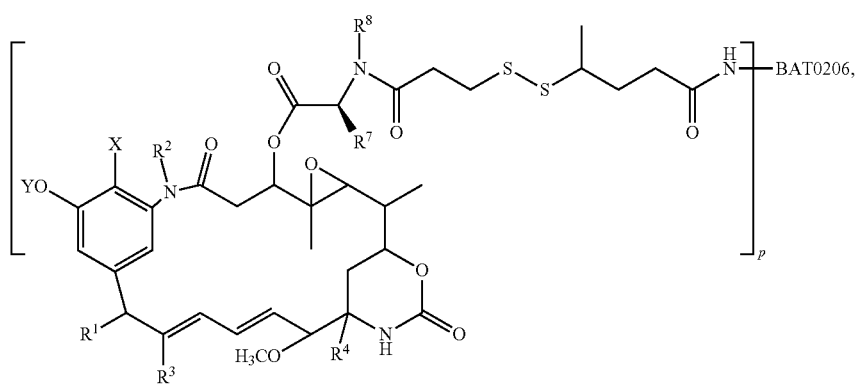

or a pharmaceutically acceptable salt or solvate thereof, wherein

X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl
$R^7$ is hydrogen, $C_1$-$C_6$ alkyl or an amino acid side chain;
$R^8$ is hydrogen or $C_{1-6}$ alkyl;
p is selected from 1, 2, 3, 4, 5, 6, 7, 8, 9, and 10; and
L is selected from substituted $C_1$-$C_{20}$ alkylene, $C_3$-$C_8$ cycloalkylene substituted $C_1$-$C_{20}$ alkylene wherein one or more of the —CH$_2$— groups are independently replaced with $C_3$-$C_8$ cycloalkylene, —S—, —NR$^8$C(=O)—, —SO$_2$NR$^8$—, or —NR$^8$SO$_2$—;

substituted $C_1$-$C_{20}$ alkylene is $C_1$-$C_{20}$ alkylene substituted with 1 to 4 —$SO_3H$, —$P(O)(OH)_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and BAT0206 is an Anti-EGFR antibody.

30. The compound of claim 27, selected from the group consisting of

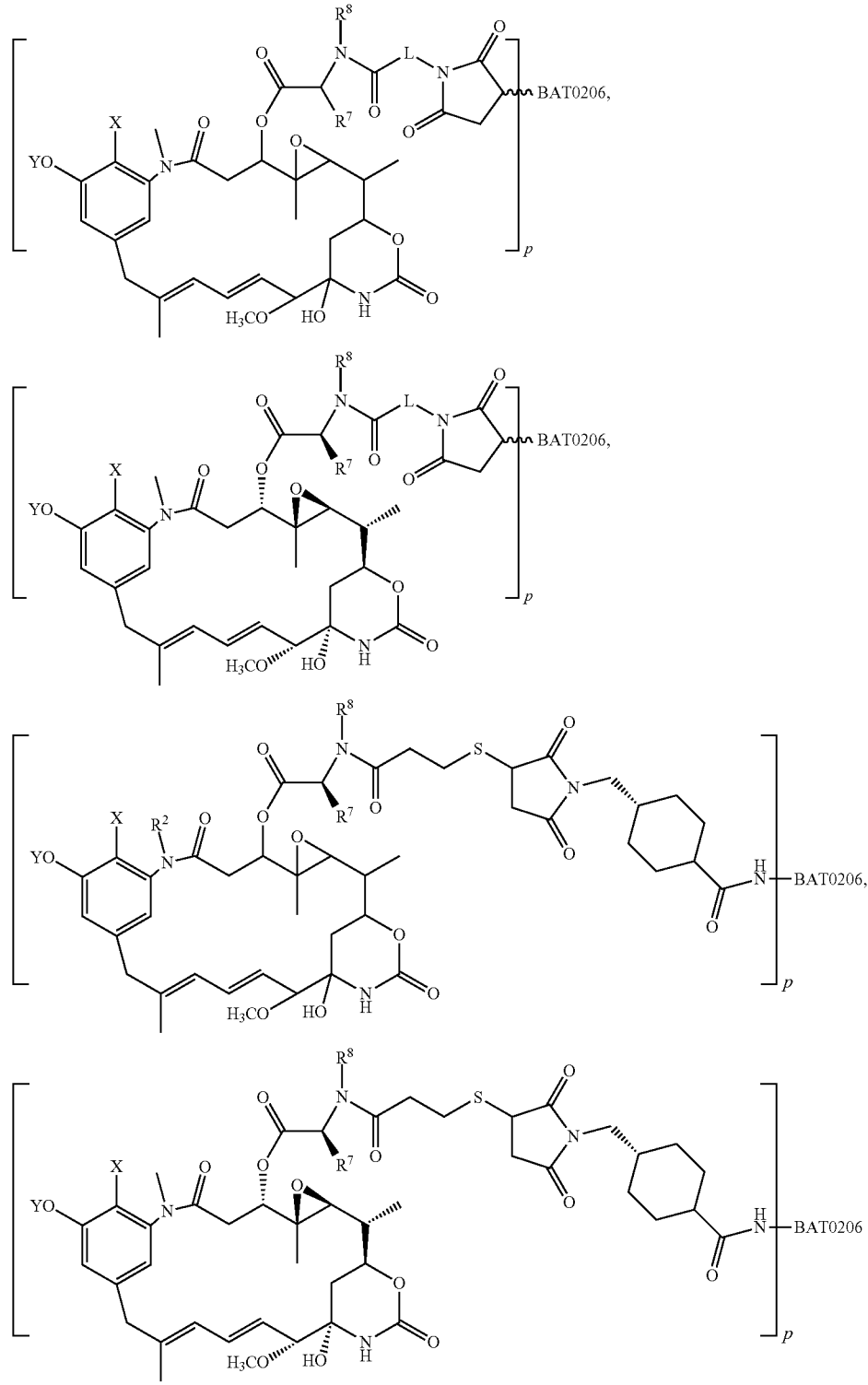

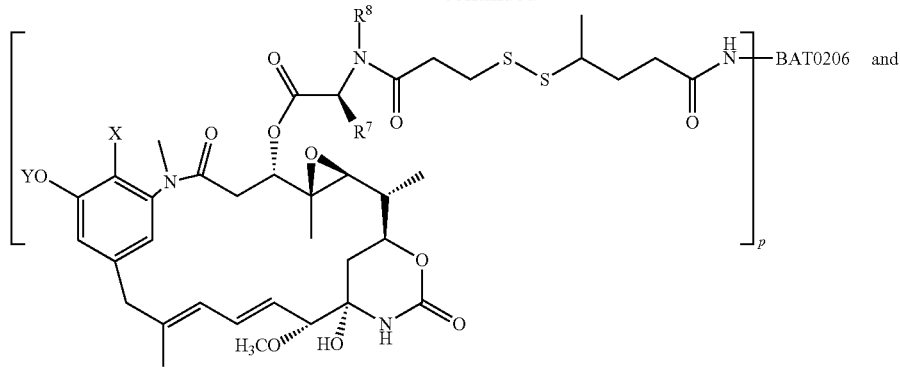
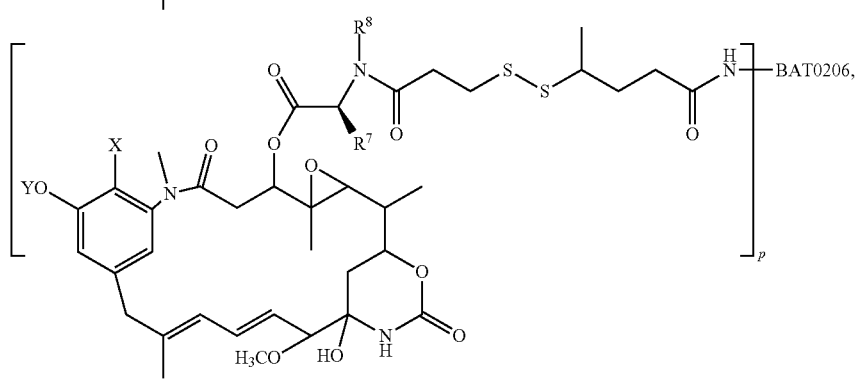
or a pharmaceutically acceptable salt or solvate thereof, wherein
X is H or Cl;
Y is H or methyl;
R$^7$ is hydrogen, C$_1$-C$_6$ alkyl or an amino acid side chain;
R$^8$ is hydrogen or C$_1$-C$_6$ alkyl;
p is selected from 1, 2, 3, 4, 5, 6, 7, 8, 9, and 10; and
BAT0206 is an Anti-EGFR antibody.
31. The compound of claim 27, selected from the group consisting of
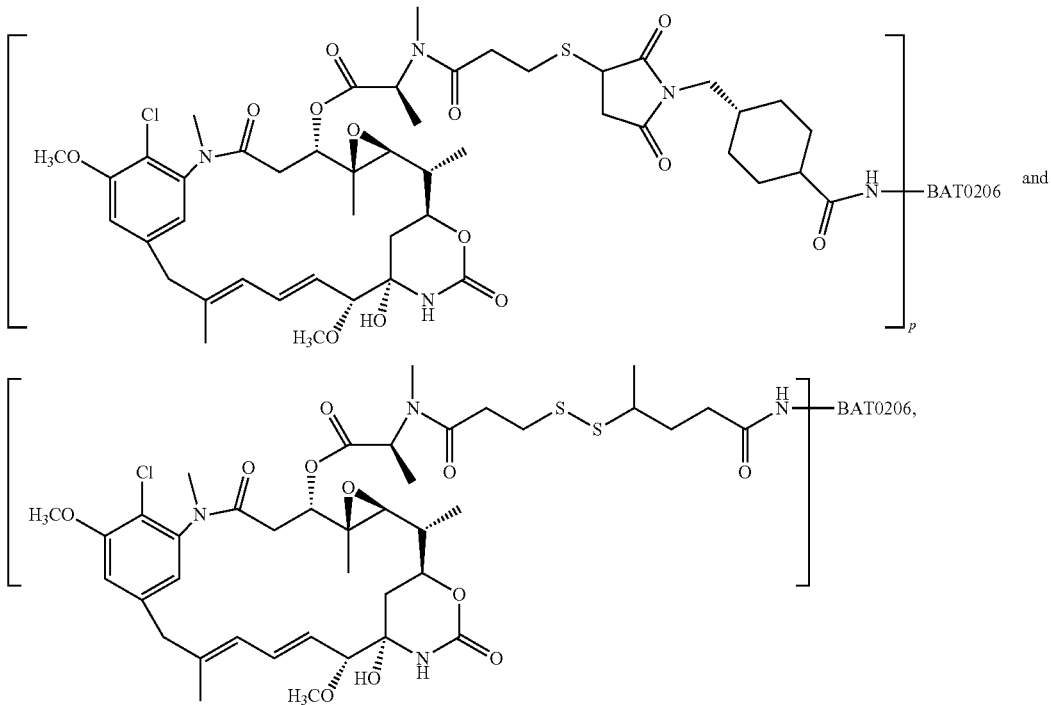

or a pharmaceutically acceptable salt or solvate thereof, wherein

BAT0206 is an Anti-EGFR antibody.

32. A compound of Formula Ib or Ib-1:

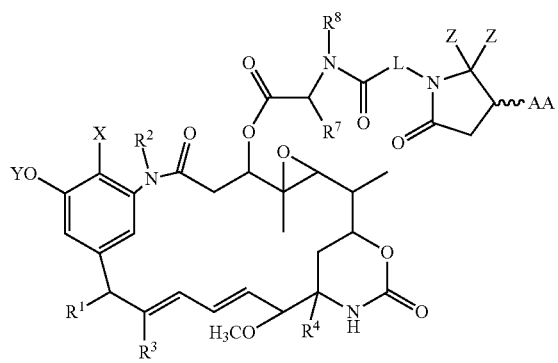

Ib

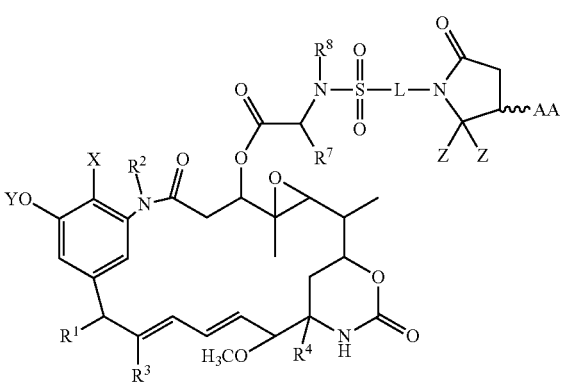

Ib-1 or a salt thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
each Z is independently hydrogen or $C_1$-$C_4$ alkyl, or the two Z with the carbon atom to which they are attached form a C=O;
in Formula Ib, L is selected from substituted $C_1$-$C_{20}$ alkylene, $C_3$-$C_8$ cycloalkylene, substituted $C_1$-$C_{20}$ alkylene wherein one or more of the —$CH_2$— groups are independently replaced with $C_3$-$C_8$ cycloalkylene, —S—, —$NR^8$C(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3$H, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CONR$^{11}R^{11}$, —$CO_2$H, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

in Formula Ib-1, L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8$C(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}R^{11}$, —$CO_2$H, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and AA is an amino acid or thiolated amino acid.

33. The compound of claim 30, which is selected from the group consisting of

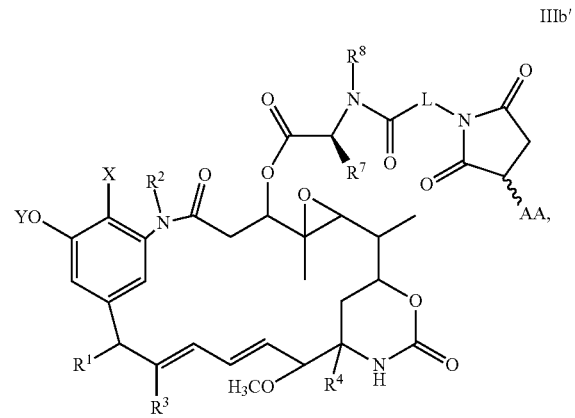

IIIb'

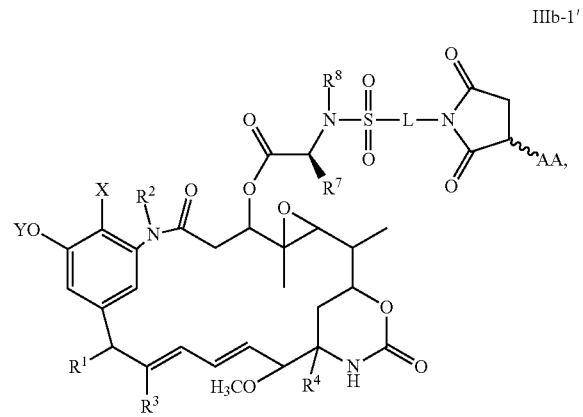

IIIb-1'

IIIb

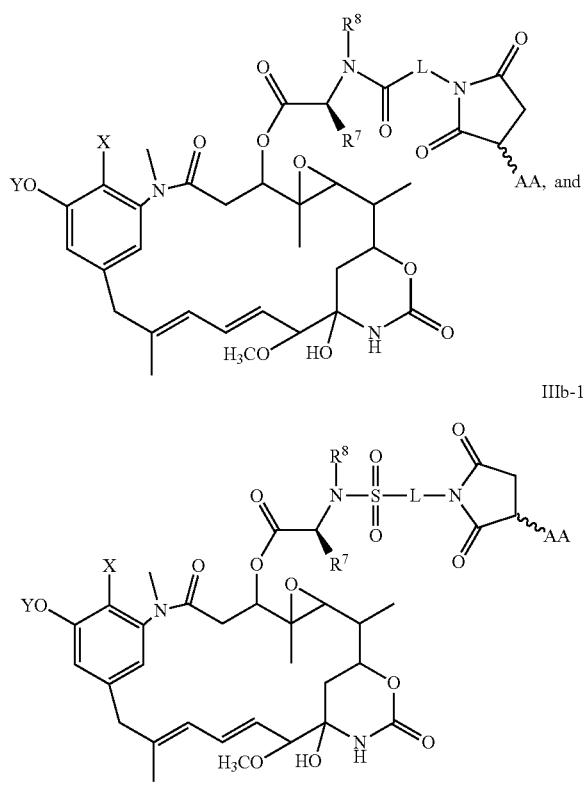

IIIb-1 or a salt thereof,
wherein
X is H or Cl;
Y is H or methyl;
$R^7$ is hydrogen, $C_1$-$C_6$ alkyl or an amino acid side chain;
$R^8$ is hydrogen or $C_1$-$C_6$ alkyl;
in Formulae IIIb' and IIIb, L is selected from substituted $C_1$-$C_{20}$ alkylene, $C_3$-$C_8$ cycloalkylene, substituted $C_1$-$C_{20}$ alkylene wherein one or more of the —$CH_2$— groups are independently replaced with $C_3$-$C_8$ cycloalkylene, —S—, —$NR^8C(=O)$—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —$P(O)(OH)_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —$CONR^{11}R^{11}$, —$CO_2H$, and wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;
in Formulae IIIb'-1 and IIIb-1, L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —$C(O)$—, —$C(=O)NR^8$—, —$NR^8C(=O)$—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —$P(O)(OH)_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —$CONR^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and AA is an amino acid or thiolated amino acid.

34. The compound of claim 32, which is of Formula IVb-1:

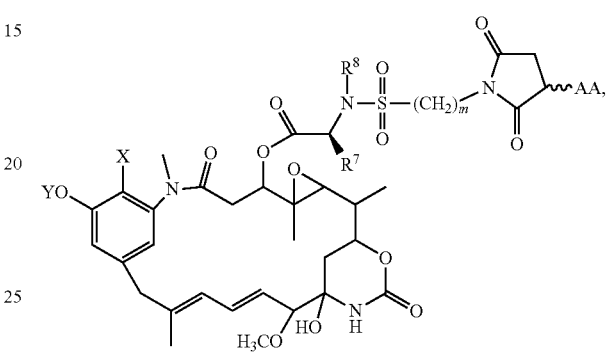

IVb-1 or a salt thereof,
wherein
X is H or Cl;
Y is H or methyl;
$R^7$ is hydrogen, $C_1$-$C_6$ alkyl or an amino acid side chain;
$R^8$ is hydrogen or $C_1$-$C_6$ alkyl;
m is selected from an integer of 1 to 20; and
AA is an amino acid or thiolated amino acid.

35. The compound of claim 32, wherein AA is

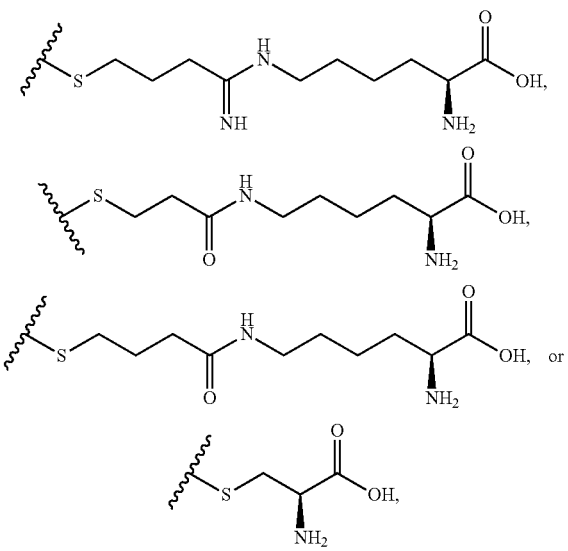

wherein ⁓ represents point of connection to the rest of the molecule.

36. The compound of claim 32, selected from the group consisting of

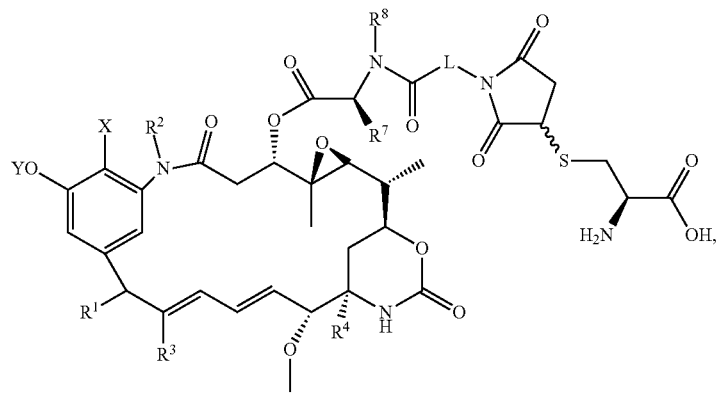

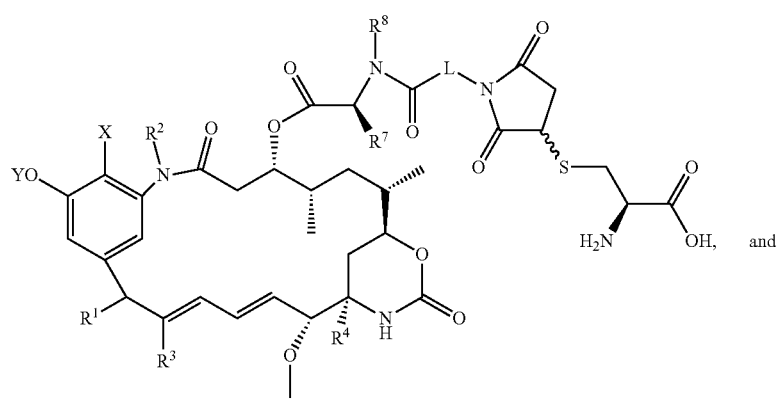

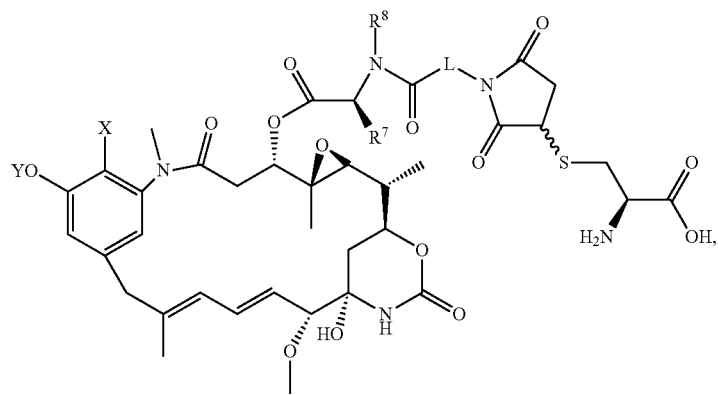

or a salt thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl
$R^7$ is hydrogen, $C_1$-$C_6$ alkyl or an amino acid side chain;
$R^8$ is hydrogen or $C_{1-6}$ alkyl;
L is selected from substituted $C_1$-$C_{20}$ alkylene, $C_3$-$C_8$ cycloalkylene, substituted $C_1$-$C_{20}$ alkylene wherein one or more of the —$CH_2$— groups are independently replaced with $C_3$-$C_8$ cycloalkylene, —S—, —$NR^8$C(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3$H, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CON$R^{11}R^{11}$, —$CO_2$H, and —NR¹¹R¹¹, wherein each R¹¹ is independently hydrogen, alkyl, aryl, cycloalkyl, cycloalkenyl, heteroaryl, and heterocyclic, or the two R¹¹ together with the nitrogen form a heterocyclic, wherein the heterocyclic is optionally substituted with one or two oxo; and m is selected from an integer of 1 to 20.

37. A compound selected from the group consisting of:

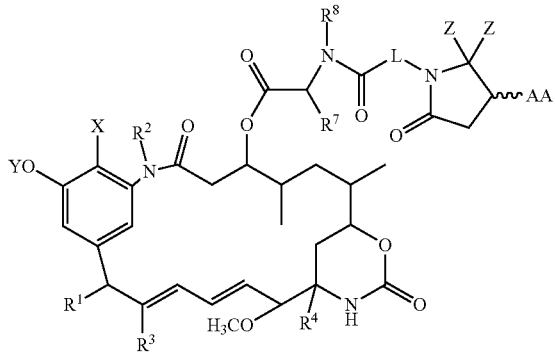

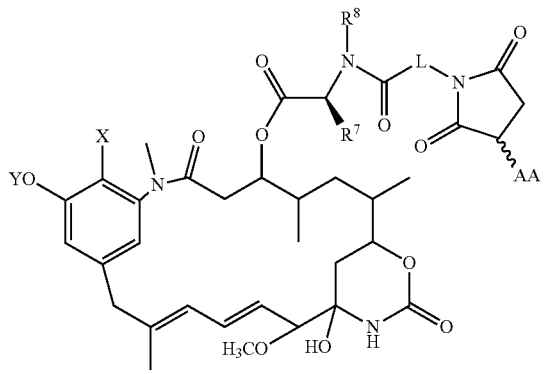

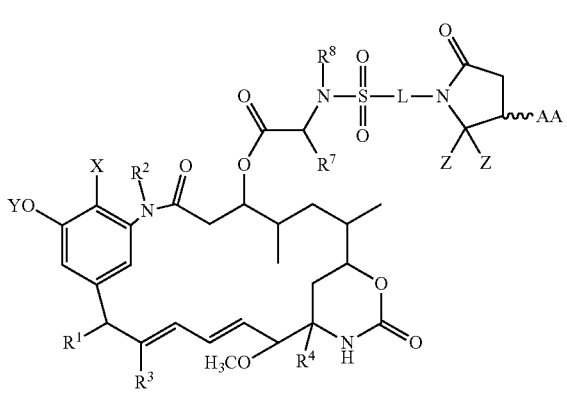

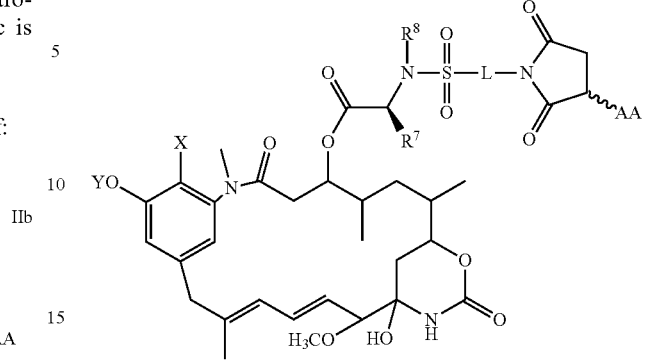

or a salt thereof, wherein

X is hydrogen or halo;

Y is selected from the group consisting of hydrogen, $C_1$-$C_6$ alkyl, $C_3$-$C_6$ cycloalkyl, and —C(=O)R⁵;

R¹ is selected from the group consisting of hydrogen, —OH, —OC(=O)R⁵ and —OR⁵;

R² is hydrogen or $C_1$-$C_6$ alkyl;

R³ is methyl, —CH₂OH, or —CH₂C(=O)R⁶;

R⁴ is —OH or —SH;

R⁵ is $C_1$-$C_6$ alkyl or benzyl;

R⁶ is $C_1$-$C_6$ alkyl, phenyl or benzyl;

R⁷ is hydrogen, $C_1$-$C_6$ alkyl or an amino acid side chain;

R⁸ is hydrogen or $C_{1-6}$ alkyl;

each Z is independently hydrogen or $C_1$-$C_4$ alkyl, or the two Z with the carbon atom to which they are attached form a C=O;

L is selected from optionally substituted $C_1$-$C_{20}$ alkylene, $C_3$-$C_8$ cycloalkylene, optionally substituted $C_1$-$C_{20}$ alkylene wherein one or more of the —CH₂— groups are independently replaced with $C_3$-$C_8$ cycloalkylene, —O—, —S—, —NR⁸—, —C(O)—, —C(=O)NR⁸—, —NR⁸C(=O)—, —SO₂NR⁸—, or —NR⁸SO₂—; substituted $C_1$-$C_{20}$ alkylene is $C_1$-$C_{20}$ alkylene substituted with 1 to 4 —SO₃H, —P(O)(OH)₂ or R²³, wherein each R²³ is independently $C_{1-6}$ alkyl optionally substituted with 1 or 2 substituents independently selected from the group consisting of —SH, —S—$C_{1-4}$ alkyl, —CONR¹¹R¹¹, —CO₂H, and —NR¹¹R¹¹, wherein each R¹¹ is independently hydrogen, alkyl, aryl, cycloalkyl, cycloalkenyl, heteroaryl, and heterocyclic, or the two R¹¹ together with the nitrogen form a heterocyclic, wherein the heterocyclic is optionally substituted with one or two oxo; and AA is an amino acid or thiolated amino acid.

38. A pharmaceutical composition comprising a compound of claim 10.

39. A method of treating a proliferative, inflammatory or immunologic disease or condition in a patient in need thereof comprising administering an effective amount of a compound of claim 10.

40. A method of treating a proliferative, inflammatory or immunologic disease or condition in a patient in need thereof comprising administering an effective amount of a compound of Formula Ib or Ib-1,

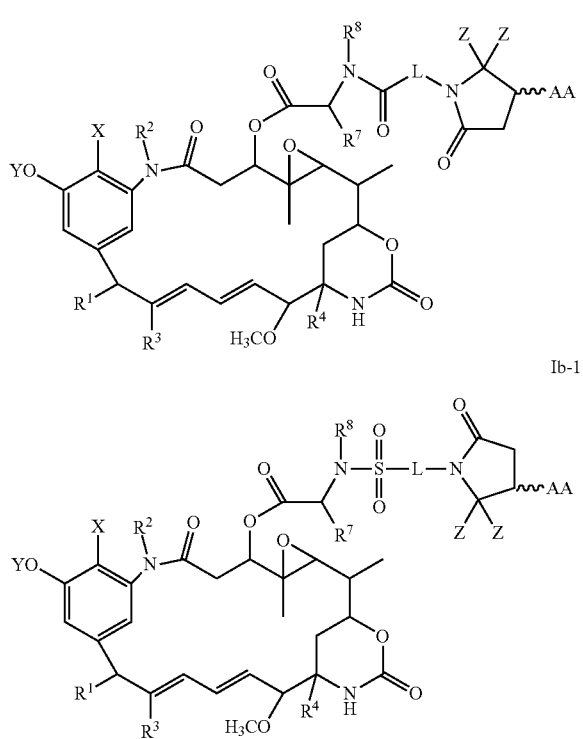

Ib

Ib-1 wherein the compound of Formula Ib or Ib-1 is generated as a result of a metabolic chemical reaction following administration of a compound of claim 9 to the patient.

wherein

X is hydrogen or halo;

Y is selected from the group consisting of hydrogen, $C_1$-$C_6$ alkyl, $C_3$-$C_6$ cycloalkyl, and —C(=O)$R^5$;

$R^1$ is selected from the group consisting of hydrogen, —OH, —OC(=O)$R^5$ and —O$R^5$;

$R^2$ is hydrogen or $C_1$-$C_6$ alkyl;

$R^3$ is methyl, —CH$_2$OH, or —CH$_2$C(=O)$R^6$;

$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_{1-6}$ alkyl;

each Z is independently hydrogen or $C_1$-$C_4$ alkyl, or the two Z with the carbon atom to which they are attached form a C=O;

in Formula Ib, L is selected from substituted $C_1$-$C_{20}$ alkylene, $C_3$-$C_8$ cycloalkylene, substituted $C_1$-$C_{20}$ alkylene wherein one or more of the —CH$_2$— groups are independently replaced with $C_3$-$C_8$ cycloalkylene, —S—, —NR$^8$C(=O)—, —SO$_2$NR$^8$—, or —NR$^8$SO$_2$—; substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;

in Formula Ib-1, L is selected from optionally substituted $C_1$-$C_{20}$ alkylene, $C_3$-$C_8$ cycloalkylene, optionally substituted $C_1$-$C_{20}$ alkylene wherein one or more of the —CH$_2$— groups are independently replaced with $C_3$-$C_8$ cycloalkylene, —O—, —S—, —NR$^8$—, —C(O)—, —C(=O)NR$^8$—, —NR$^8$C(=O)—, —SO$_2$NR$^8$—, or —NR$^8$SO$_2$—; substituted $C_1$-$C_{20}$ alkylene is $C_1$-$C_{20}$ alkylene substituted with 1 to 4 —SO$_3$H, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CONR$^{11}$R$^{11}$, —CO$_2$H, and —NR$^{11}$R$^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo; and AA is an amino acid or thiolated amino acid.

41. The method of claim 40, wherein the compound of Formula Ib or Ib-1 is

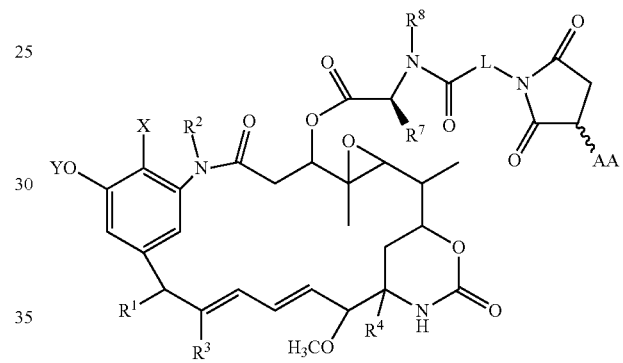

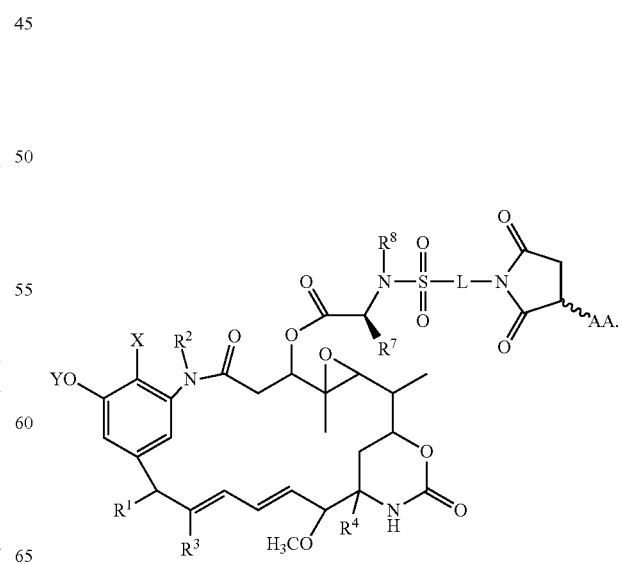

42. A method of treating a proliferative, inflammatory or immunologic disease or condition in a patient in need thereof comprising administering an effective amount of a compound of Formula IIb or IIb-1,

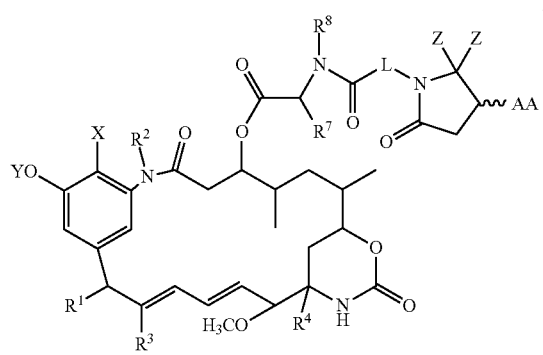

IIb

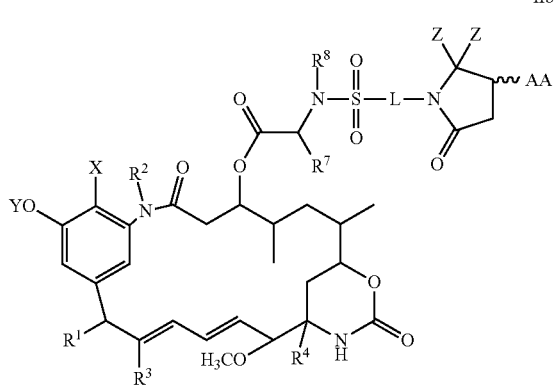

IIb-1 wherein the compound of Formula IIb or IIb-1 is generated as a result of a metabolic chemical reaction following administration of a compound of claim 14 to the patient.

43. The method of claim 40, wherein the antigen binding unit is an antibody comprising SEQ ID 1 and 2, or SEQ ID 3 and 4, or SEQ ID 5 and 6, or SEQ ID 7 and 8, or SEQ ID 9 and 10, SEQ ID 11 and 12, or SEQ ID 13 and 14, or an equivalent thereof.

44. A method of preparing a compound of claim 10 or a pharmaceutically acceptable salt thereof, comprising contacting an antigen binding unit with a compound of Formula I or I-1:

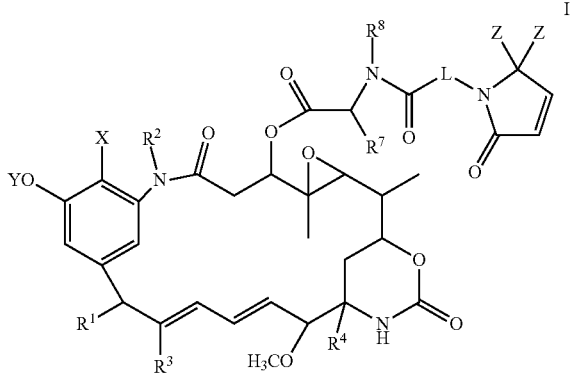

I

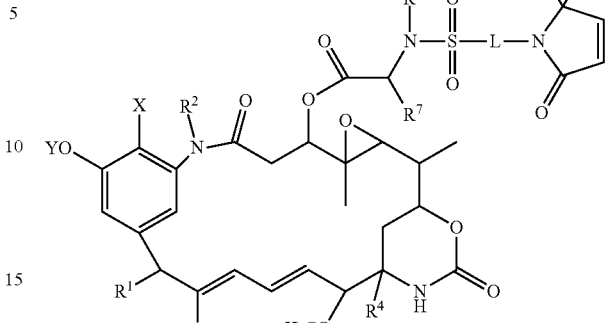

I-1 or a salt thereof,
wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
each Z is independently hydrogen or $C_1$-$C_4$ alkyl, or the two Z with the carbon atom to which they are attached form a C=O; and
in Formula I, L is selected from substituted $C_1$-$C_{20}$ alkylene, $C_3$-$C_8$ cycloalkylene, substituted $C_1$-$C_{20}$ alkylene wherein one or more of the —$CH_2$— groups are independently replaced with $C_3$-$C_8$ cycloalkylene, —S—, —$NR^8$C(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl substituted with 1 or 2 substituents independently selected from the group consisting of —SH, —S—$C_{1-4}$ alkyl, —CON$R^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo;
in Formula I-1, L is selected from optionally substituted $C_1$-$C_{20}$ alkylene, $C_3$-$C_8$ cycloalkylene, optionally substituted $C_1$-$C_{20}$ alkylene wherein one or more of the —$CH_2$— groups are independently replaced with $C_3$-$C_8$ cycloalkylene, —O—, —S—, —$NR^8$—, —C(O)—, —C(=O)$NR^8$—, —$NR^8$C(=O)—, —$SO_2NR^8$—, or —$NR^8SO_2$—; substituted $C_1$-$C_{20}$ alkylene is $C_1$-$C_{20}$ alkylene substituted with 1 to 4 —$SO_3H$, —P(O)(OH)$_2$ or $R^{23}$, wherein each $R^{23}$ is independently $C_{1-6}$ alkyl optionally substituted with 1 or 2 substituents independently selected from the group consisting of —SH, —S—$C_{1-4}$ alkyl, —CON$R^{11}R^{11}$, —$CO_2H$, and —$NR^{11}R^{11}$, wherein each $R^{11}$ is independently hydrogen, alkyl, aryl, cycloalkyl, cycloalkenyl, heteroaryl, and heterocyclic, or the two $R^{11}$ together with the nitrogen form a heterocyclic, wherein the heterocyclic is optionally substituted with one or two oxo.

45. A method of preparing a compound of Formula Va-1:

$$\text{Va-1}$$

or a pharmaceutically acceptable salt thereof, comprising contacting an antigen binding unit with a compound of Formula V-1:

$$\text{V-1}$$

or a salt thereof.

46. The method of claim 44, wherein the antigen binding unit is an antibody comprising SEQ ID 1 and 2, or SEQ ID 3 and 4, or SEQ ID 5 and 6, or SEQ ID 7 and 8, or SEQ ID 9 and 10, SEQ ID 11 and 12, or SEQ ID 13 and 14.

* * * * *